US010621686B2

(12) United States Patent
Mazar et al.

(10) Patent No.: US 10,621,686 B2
(45) Date of Patent: Apr. 14, 2020

(54) PATIENT CARE AND HEALTH INFORMATION MANAGEMENT SYSTEM

(71) Applicant: Vios Medical, Inc., St. Paul, MN (US)

(72) Inventors: Scott Mazar, Woodbury, MN (US); Amit Patel, Woodbury, MN (US)

(73) Assignee: Vios Medical, Inc., Woodbury, MN (US)

( * ) Notice: Subject to any disclaimer, the term of this patent is extended or adjusted under 35 U.S.C. 154(b) by 685 days.

(21) Appl. No.: 14/681,385

(22) Filed: Apr. 8, 2015

(65) Prior Publication Data

US 2015/0302150 A1    Oct. 22, 2015

Related U.S. Application Data

(60) Provisional application No. 62/113,691, filed on Feb. 9, 2015, provisional application No. 61/980,347, filed on Apr. 16, 2014.

(51) Int. Cl.
*G06Q 50/22* (2018.01)
*G16H 40/20* (2018.01)
(Continued)

(52) U.S. Cl.
CPC .............. *G06Q 50/22* (2013.01); *G06Q 10/10* (2013.01); *G06Q 50/24* (2013.01); *G08B 21/02* (2013.01);
(Continued)

(58) Field of Classification Search
CPC ...... G06F 19/327; G06Q 50/22; G16H 40/20; A61B 5/002
(Continued)

(56) References Cited

U.S. PATENT DOCUMENTS

| 4,531,527 A | 7/1985 | Reinhold, Jr. et al. |
| 6,032,119 A | 2/2000 | Brown et al. |

(Continued)

FOREIGN PATENT DOCUMENTS

| EP | 2658440 | 11/2013 |
| KR | 10-2013-0125792 | 11/2013 |

(Continued)

OTHER PUBLICATIONS

European Search Report in Application No. 15780236.4, dated Sep. 22, 2017, 11 pages.
(Continued)

*Primary Examiner* — Hiep V Nguyen
(74) *Attorney, Agent, or Firm* — Fish & Richardson P.C.

(57) ABSTRACT

Streamlined and integrated patient care and health information management systems and methods for reducing the need for costly, near constant patient monitoring by providing system components that allow healthcare professionals to view the most important data for a number of patients in varying physical locations in a seamless manner are disclosed. Various components of the system can be used to monitor patients; measure, record, and track vital signs; and coordinate patient care in an automated fashion. Patients that have a achieved a relatively stable condition during a recovery process, but who still require or would benefit from near constant, or frequent vital sign monitoring can be provided with one or more body worn vital sign sensors. These patient worn sensors can track vital sign and other information about patients, including patient movement, activity, and sleep patterns.

20 Claims, 19 Drawing Sheets

(51) Int. Cl.
  *G08B 21/02* (2006.01)
  *G06Q 10/10* (2012.01)
  *G06Q 50/24* (2012.01)

(52) U.S. Cl.
  CPC ......... *G08B 21/0211* (2013.01); *G16H 40/20* (2018.01)

(58) Field of Classification Search
  USPC .......................................................... 705/2
  See application file for complete search history.

(56) References Cited

U.S. PATENT DOCUMENTS

| | | |
|---|---|---|
| 7,249,036 B2 | 7/2007 | Bayne |
| 7,716,065 B1 | 5/2010 | Maxwell, Jr. et al. |
| 7,739,126 B1 | 6/2010 | Cave et al. |
| 7,786,874 B2 | 8/2010 | Rodgers |
| 8,000,978 B2 | 8/2011 | Wager et al. |
| 8,117,046 B2 | 2/2012 | Bayne |
| 8,285,356 B2 | 10/2012 | Bly et al. |
| 8,311,603 B2 | 11/2012 | Faersnes et al. |
| 8,340,981 B1 | 12/2012 | Cave |
| 8,412,317 B2 | 4/2013 | Mazar |
| 8,460,189 B2 | 6/2013 | Libbus et al. |
| 8,504,291 B2 | 8/2013 | Bayne |
| 8,591,411 B2 | 11/2013 | Bonet et al. |
| 8,639,528 B1 | 1/2014 | Cave |
| 8,751,160 B2 | 6/2014 | Bayne |
| 8,768,726 B1 | 7/2014 | Cave |
| 8,786,402 B2 | 7/2014 | Barnes |
| 2003/0078810 A1 | 4/2003 | Douglas |
| 2004/0111291 A1 | 6/2004 | Dust et al. |
| 2004/0122702 A1 | 6/2004 | Sabol et al. |
| 2004/0172283 A1 | 9/2004 | Vanderveen et al. |
| 2005/0146431 A1 | 7/2005 | Hastings et al. |
| 2005/0151640 A1 | 7/2005 | Hastings |
| 2007/0116036 A1 | 5/2007 | Moore |
| 2007/0123755 A1 | 5/2007 | Rice |
| 2007/0208233 A1 | 9/2007 | Kovacs |
| 2008/0015903 A1 | 1/2008 | Rodgers |
| 2009/0054735 A1* | 2/2009 | Higgins ............... A61B 5/0006 600/300 |
| 2009/0119126 A1 | 5/2009 | Johnson et al. |
| 2009/0177702 A1* | 7/2009 | Stahmann .......... A61B 5/02405 |
| 2009/0204434 A1 | 8/2009 | Breazeale |
| 2009/0216558 A1 | 8/2009 | Reisman et al. |
| 2009/0264792 A1 | 10/2009 | Mazar |
| 2009/0273467 A1 | 11/2009 | Elixmann et al. |
| 2010/0001838 A1 | 1/2010 | Miodownik et al. |
| 2011/0054946 A1* | 3/2011 | Coulter .................. G06Q 10/06 705/3 |
| 2011/0218410 A1 | 9/2011 | Buisman et al. |
| 2011/0224498 A1 | 9/2011 | Banet et al. |
| 2011/0224564 A1* | 9/2011 | Moon ..................... A61B 5/00 600/509 |
| 2012/0072238 A1 | 3/2012 | Collins et al. |
| 2012/0108917 A1 | 5/2012 | Libbus et al. |
| 2012/0129139 A1 | 5/2012 | Partovi |
| 2012/0316911 A1 | 6/2012 | Schwarz |
| 2013/0030825 A1 | 1/2013 | Bagwandeen et al. |
| 2013/0035946 A1 | 2/2013 | Ratan et al. |
| 2013/0073299 A1 | 3/2013 | Warman |
| 2013/0150912 A1 | 6/2013 | Perschbacher et al. |
| 2013/0197942 A1 | 8/2013 | Chiu et al. |
| 2013/0214850 A1 | 8/2013 | Aga et al. |
| 2013/0297350 A1 | 11/2013 | Gross et al. |
| 2013/0332197 A1 | 12/2013 | Hinkel |
| 2014/0288961 A1 | 9/2014 | Bayne |
| 2014/0337055 A1 | 11/2014 | Barnes |
| 2015/0310173 A1 | 10/2015 | Coney |
| 2015/0332011 A1 | 11/2015 | Ting et al. |
| 2016/0239626 A1 | 8/2016 | Buckley et al. |
| 2016/0253457 A1 | 9/2016 | Anumolu et al. |
| 2016/0314277 A1 | 10/2016 | Korhonen et al. |
| 2017/0017767 A1 | 1/2017 | Flower et al. |

FOREIGN PATENT DOCUMENTS

| | | |
|---|---|---|
| WO | WO 00/41613 | 7/2000 |
| WO | WO 2013/188838 | 12/2013 |

OTHER PUBLICATIONS

Labrador et al., "Location-Based Information Systems: Developing Real-Time Tracking Applications," Chapman and Hall/CRC, Oct. 2010, 11-12.
Vermesan et al., "Internet of Things: Converging Technologies for Smart Environments and Integrated Ecosystems," River Publishers, Jul. 2013, 54-57.
'zephyranywhere.com' [online]. "ZephyrLIFE—Home," 2015, [retrieved on Jul. 9, 2015]. Retrieved from the Internet: URL<http://zephyranywhere.com/healthcare/zephyrlife-home/>.
"Patient Centric Monitoring Throughout the Continuum of Clinical Care," Zephyr, 2012, 5 pages.
"Nuvant Mobile Cardiac Telemetry System Quick Start Guide," Coreventis, © 2009-2013, 2 pages.
International Search Report and Written Opinion in International Application No. PCT/US2015/025265, dated Sep. 15, 2015, 13 pages.
Distributed Systems: Concepts and Design, 5th Edition, Addison-Wesley, 2011, Chapters 1-4, 6, and 19, 389 pages.
EP Office Action in EP Appln. No. 15780236.4, dated Jan. 3, 2019, 12 pages.
Internet of Things: Converging Technologies for Smart Environments and Integrated, River Publishers, 2013, Chapter 7, 35 pages.
Location-Based Information Systems: Developing Real-Time Tracking Applications, 2010, Chapman and Hail/CRC, Chapters 1-2, 55 pages.
Metadata-driven Software Systems in Biomedicine: Designing Systems that can adapt to Changing Knowledge, Springer, 2011, Chapters 1, 4-6, and 8-12, 211 pages.
M-Health: Emerging Mobile Health Systems, Springer, 2006, Chapters 5 and 8-19, 218 pages.
Wikipedia.com [online] "mHealth", [retrieved on Dec. 17, 2018], retrieved from: URL <https://en.wikipedia.org/w/index.php?title=MHealth&oldid=603796636>, 15 pages.
Wikipedia: "Body area network", [retrieved on Dec. 17, 2018] retrieved from: URL <https://en.wikipedia.org/w/index.php?title=Body_area_network&oldid=601414459>, 5 pages.

* cited by examiner

US 10,621,686 B2

PATIENT CARE AND HEALTH INFORMATION MANAGEMENT SYSTEM

CROSS-REFERENCE TO RELATED APPLICATION(S)

This application claims priority to U.S. Provisional Application No. 62/113,691, filed on Feb. 9, 2015 and to U.S. Provisional Application No. 61/980,347, filed on Apr. 16, 2014. The disclosure of these prior applications is considered part of and is incorporated by reference in the disclosure of this application.

BACKGROUND

Patient treatment experiences within hospitals and other healthcare facilities can vary in numerous ways, including differences in initial interaction between a patient and caregivers, diagnosis, progression of treatment, physical movement of a patient within a facility, length of stay, recovery, and rehabilitation. For example, in some cases, a patient initiates interaction with a hospital by arriving at an emergency room to have an immediate need (such as an injury, heart failure, sudden pain, or other sudden health emergency) addressed by the hospital staff. From there, the patient may be rushed into surgery, scheduled for surgery at a later time, given one or more medications, scheduled for a later diagnostic consultation, treated and released, removed to an intensive care unit, moved to a recovery ward, or any other myriad actions could be taken with respect to the patient. As another example, in some cases, a patient initiates interaction with a hospital by scheduling a surgical procedure. In such a scenario, the patient may, for example, arrive at the hospital, be prepped for surgery, undergo the surgical procedure, spend an amount of time in a recovery ward, and then be moved to a general hospital ward before being released from the hospital and sent home.

In many cases, one or more surgical procedures make up part of a treatment plan for a patient. There are multiple environments that patients can be transitioned through after a surgical procedure. Immediately after a procedure, patients are gradually brought back to a stable condition, after which they are discharged to the home or a long-term care setting. The initial recovery process starts in the Intensive Care Unit (ICU) for patients requiring 24/7 clinician oversight. An ICU has the necessary equipment to monitor patient status and high staffing ratios to aid patient recovery. This environment can be very expensive for patients, as it is often the highest per-day cost out of any room in the hospital—leaving this environment as soon as possible is beneficial as it minimizes overall cost. For hospitals that are built around critical-care, ICU patient throughput is a highly scrutinized metric for the efficiency of their overall operations—it is the hospital's most expensive environment to staff and resource, and keeping patients there longer than necessary means another patient must wait for a bed to become available prior to receiving treatment. The transition of patients out of the ICU is therefore preferred for both hospitals and patients, but the risks associated with premature discharge often prevents early release of a patient.

While a patient is located in the ICU, basic vital sign data needed to determine patient stability are measured, recorded, tracked, and trended, a process which can often be clinical staff dependent, and which can restrict a clinician to a particular physical location where they can monitor patients and review vital signs and other data in person (e.g., by viewing a bedside ECG display that utilizes sensors connected to a patient). Patient vital signs that are collected can include: blood pressure, body temperature, respiratory rate, blood oxygenation, heart rhythm (via ECG), and heart rate. Along with this, there are soft metrics also used such as patient responsiveness and visual assessment.

In some cases, the recovery process can include moving a patient to a recovery room, either directly after surgery, or after a period of time spent in an ICU. As with ICUs, patient monitoring within a recovery room environment also includes a heavy reliance on clinician interpretation of any data that is generated, and this data may or may not be easily available to the original physician overseeing the patient's recovery.

From an ICU or recovery room, a patient can often be moved to a general ward. General wards often include lower caregiver to patient staffing ratios and less or no vital sign monitoring. In many cases, vital signs are often not monitored on a near constant basis, but rather nurses will make rounds to measure key vital signs. Additionally, such vital sign measurement can often be limited to a few basic parameters such as body temperature and blood pressure. After the general ward, the next phase in patient recovery progression is often discharge of the patient. It is generally considered best for patients to reach home and recover in this more comfortable environment as soon as possible. Being released from a hospital to continue recovery at home can minimize the risk of contracting unrelated in-hospital complications, and can better allow family members to aid with recovery, at lower-cost to the patient.

During the management of patients in multiple in-hospital and out-of-hospital environments, various stakeholders (human and non-human) are interested in consuming data and metrics associated with patient status and the care received. These metrics and data are often resident in disparate human and non-human sources, and are communicated to stakeholders through various modalities. Furthermore, coordinating care in a patient-centric manner is difficult as many stakeholders are continuously changing.

SUMMARY

The present disclosure is directed toward a real-time platform for complete patient-centric exchange, consumption, aggregation, distribution, archival, and management of critical information and relationships between human or non-human parties or entities that interact with patient or patient-related data. This platform can facilitate comprehensive interactivity with critical patient-oriented data between parties or entities that interact with patients or patient data throughout the care continuum.

A streamlined and integrated patient care and health information management system can be utilized to reduce the need for costly, near constant patient monitoring by providing system components that allow healthcare professionals to view the most important data for a number of patients in varying physical locations in a seamless manner. Various components of the system can be used to monitor patients; measure, record, and track vital signs; and coordinate patient care among numerous different healthcare professionals and caregivers. Patients that have a achieved a relatively stable condition during a recovery process, but who still require or would benefit from near constant, or frequent vital sign monitoring can be provided with one or more body worn vital sign sensors. These patient worn sensors can track vital sign information such as blood pressure, body temperature, respiratory rate, blood oxygenation, heart rhythm (via ECG), heart rate, blood glucose level, and hydration levels. The sensors can also track and record additional information about patients, including patient movement, activity, and sleep patterns.

The information recorded by the sensors can be transmitted to a display device to allow caregivers to observe the information and make adjustments to patient care for the patient based on the information. The information can also be transmitted to a central information repository to allow historical vital sign and other information for the patient to be logged. This can allow caregivers to access the information to identify trends for the patient, assist with diagnosis, track the progress of patient recovery, or potentially identify previously unnoticed issues or anomalies. Both real time and historical vital sign and other information for a patient can be accessed by caregivers who are not at the same physical location as the patient. This can allow for increased monitoring of patients while allowing doctors and other caregivers to observe and care for a larger number of patients spread across various different locations. Such patient monitoring and tracking can allow for a quicker transition of a patient from a relatively high cost and labor intensive environment such as an ICU to a lower cost environment that requires a lower health care staff to patient ratio, such as a general ward. Such systems can even allow for quicker discharge of a patient from a hospital (e.g., quicker transition to a home environment) by providing the patient with one or more sensors that can be worn by the patient outside of the hospital environment (such as at home) which can provide a necessary level of patient monitoring by transmitting vital sign and other information to caregivers located at a remote healthcare facility.

Additionally, the system can allow various caregivers to more efficiently coordinate patient care and more seamlessly transition a patient from one location to another, from one environment to another, or from one set of caregivers to another. For example, caregivers can use the system to make notes regarding patient care which can be stored along with patient vital sign and other information. For example, a nurse can make a note about a patient's eating habits, or a physical therapist can make notes regarding a patient's progress during therapy sessions or current physical abilities. The notes can then be viewed by other caregivers when the caregivers access information about the patient to allow the other caregivers to adjust one or more aspects of the patient's treatment plan. In some instances, a note or message can be addressed to the attention of one or more other caregivers. For example, a nurse can make a note that a patient had a particular reaction after taking medication and set the note to the attention of a pharmacist responsible for care of the patient. The pharmacist can receive an alert that a new note has been addressed to his attention, review the note, and review other information associated with the patient to best determine if a change to the patient's medication schedule needs to be made.

The system can also be configured to provide alerts regarding a current status of a patient to one or more caregivers. For example, a patient worn sensor can monitor ECG readings and heart rate for a patient and analyze this information to determine if the ECG readings and heart rate are within a specified acceptable range for the patient. If the readings are outside of an acceptable range for the patient, the monitor can send an alert to one or more caregivers to inform the caregivers that an emergency situation associated with the patient (such as, for example, cardiac arrest) is occurring. Various settings can be adjusted to classify various sensor detected patient events by severity or type, or to specify which caregivers should be notified for different patient events.

In general, one innovative aspect of the subject matter described in this specification can be embodied in methods that include the actions of receiving, by a computer system and from a patient-worn mobile sensor associated with a patient, vital sign information associated with the patient; receiving, by the computer system, user input provided by a first caregiver indicating care information for the patient; determining, by the computer system and based on the received vital sign information and received user input, a predicted future location for the patient; determining, by the computer system and based on the received vital sign information and received user input, a predicted time window for arrival of the patient at the predicted future location; identifying, by the computer system, a second caregiver based on the predicted future location; and sending, by the computer system, an alert message to the second caregiver, the alert message including an identifier for the patient and an indication of the predicted time window.

These and other embodiments can each optionally include one or more of the following features. The vital sign information and the user input can be received by the computer system while the patient is located in a first section of a healthcare facility, wherein the predicted future location is a second section of the healthcare facility different than the first section, and the second caregiver is a clinician scheduled to work in the second section of the healthcare facility during the predicted time window. The vital sign information and the user input can be received by the computer system while the patient is located in a healthcare facility, wherein the predicted future location is a location outside of the healthcare facility. Determining the predicted future location for the patient can include determining that the patient is to be discharged from the healthcare facility during the predicted time window. The alert message can include an indication that the patient is to be discharged during the predicted time window.

The methods can further include actions of determining, by the computer system and based on the received vital sign information and received user input, a predicted future medical occurrence for the patient; wherein determining the predicted future location for the patient includes accessing location information for the predicted future location, the location information including attributes for the predicted future location, and determining that the attributes for the predicted future location match criteria required for the predicted future medical occurrence; and wherein identifying the second caregiver includes accessing caregiver information for the second caregiver and determining, using the accessed caregiver information, that the second caregiver is suitable for participating in the future medical occurrence for the patient. The methods can further include identifying a required future treatment for the patient. Determining the predicted future location for the patient can include determining that the predicted future location is suitable for the required future treatment.

Identifying the second caregiver can include identifying that the second caregiver is scheduled to work at the predicted future location during the predicted time window. Determining the predicted future location for the patient can be performed in response to determining, using the received vital sign information, that the patient has sufficiently covered from a previous medical occurrence. The predicted future location can be an outpatient treatment facility. Determining the predicted future location for the patient can include determining that the patient requires outpatient treatment of a type performed at the outpatient treatment facility. Identifying the second caregiver can include determining that the second caregiver is located within a specified proximity of the predicted future location.

Various other functions and benefits of such a system will be apparent from the foregoing detailed description and claims.

BRIEF DESCRIPTION OF THE DRAWINGS

Like reference numbers and designations in the various drawings indicate like elements.

DETAILED DESCRIPTION

Figure 1:
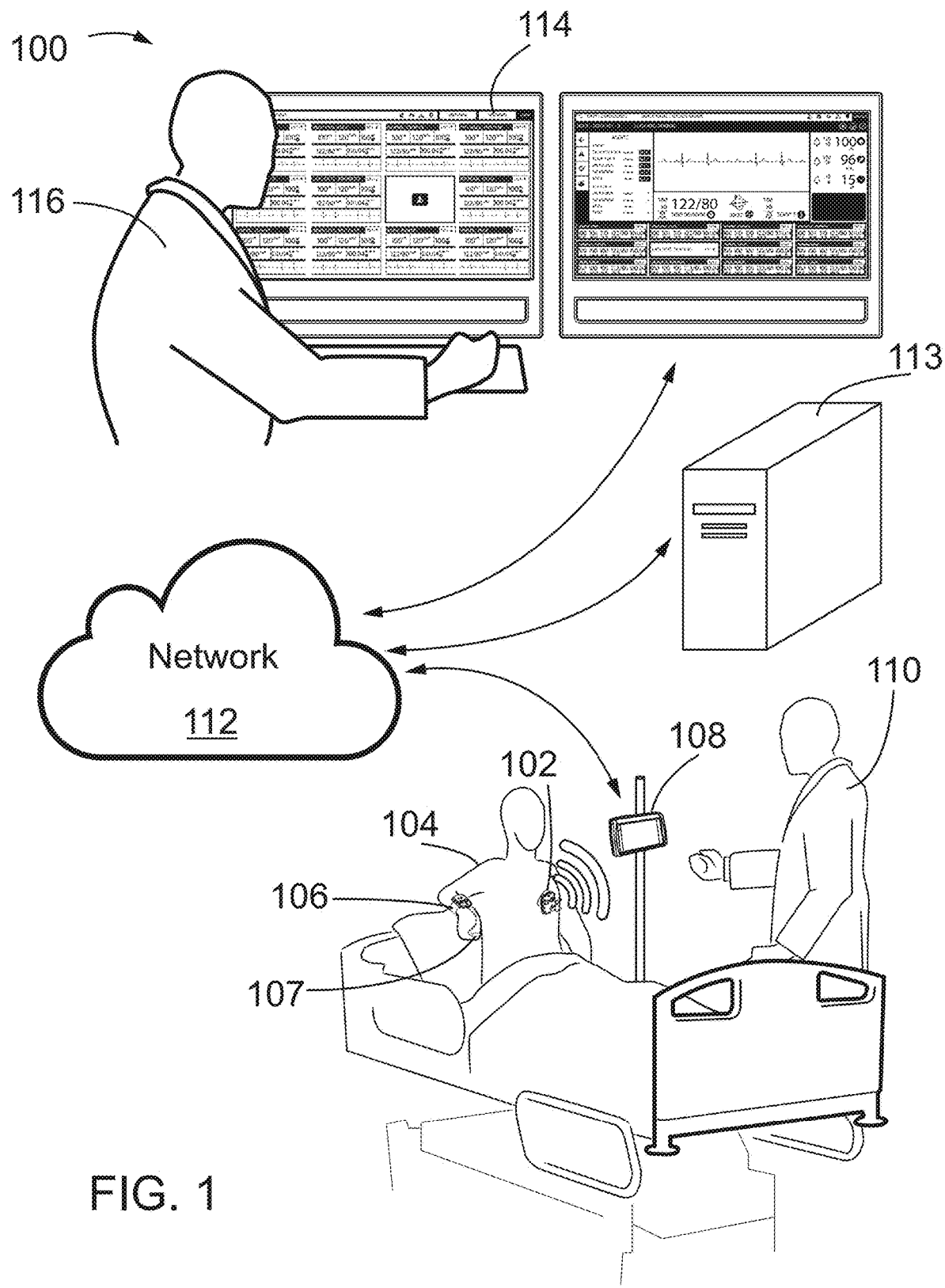
FIG. 1 shows an example system for tracking and monitoring information associated with a patient.

FIG. 1 shows an example system 100 for tracking and monitoring information associated with a patient. The system 100 can be used to monitor patient vital signs, track patient activity, track patient movement, record information associated with a patient, coordinate patient care, and provide up-to-date information to health care providers. The system 100 includes one or more patient worn sensors for detecting and recording various vital signs and other information for a patient. For example, the system 100 can include a chest sensor 102 affixed to the chest of a patient 104 for tracking various vital signs of the patient 104. The system 100 can additionally include a wrist sensor 106, which in the example shown is affixed to the patient 104's right wrist, but in practice could be affixed to either wrist of the patient 104. The patient worn sensors can interact with other components of the system 100 to identify alarm states for the patient 104. Alarm states can include various medical states or medical emergencies for the patient that may or may not require intervention by one or more caregivers. In some implementations, alarm states can be identified based on deviation of one or more vital signs or other metrics for the patient 104 outside of an acceptable range. Detection of an alarm state or other issue associated with the patient 104 or components of the system 100 that requires attention can result in one or more components of the system 100 issuing an alert. An alert can take the form of information regarding an alarm state or other issue being displayed by a computing device, a notification sent to one or more caregivers, an audio alarm, a visual alarm, a tactile alarm (such as vibration), or another indicator.

The chest sensor 102 can include several adherent electrodes for contacting the skin of the patient 104 to record various vital signs for the patient, including heart rhythm (via ECG) and heart rate. The chest sensor 102 can be, for example, a 6-lead ECG sensor having I, II, III, aVL, aVR, and aVF leads. Other vital signs that can be monitored by the chest sensor 102 or a combination of the chest sensor 102 and the wrist sensor 106 can include blood pressure, body temperature, respiratory rate, blood oxygenation, blood glucose level, hydration levels and perspiration. In some implementations, the chest sensor 102 can include a reusable or permanent portion as well as disposable portions. For example, the chest sensor 102 can include a permanent housing for storing electrical components for processing signals received from and detected in association with the patient and for transmitting information to other devices. The chest sensor 102 can further include a disposable adherent electrode pad designed to affix to the chest of the patient 104. Electrodes included as part of the disposable adherent electrode pad can be configured to contact electrical leads of the permanent housing to convey signals from the patient 104 to the electrical components within the chest sensor 102. In some implementations, the permanent housing can include snap connectors for engaging electrodes of the disposable adherent electrode pad and for securing the disposable adherent electrode pad to the permanent housing. The disposable adherent electrode pad can be periodically removed and replaced with a fresh disposable adherent electrode pad while allowing many of the components of the chest sensor 102 to be continually reused.

The chest sensor 102 can also include sensors for detecting bio-impedance in order to monitor hydration levels, body fat levels, or other fluid levels for the patient 104. In some implementations, the chest sensor 102 can include electronics for processing and analyzing vital sign information and other information collected from the patient 104. In some implementations, the chest sensor 102 and/or other patient worn sensors collect raw, pre-processed information which is then transmitted to other portions of the system 100 for further processing and analysis.

In some implementations, the chest sensor 102 includes a temperature sensor that extends from a main body of the chest sensor 102 to underneath the patient 104's armpit for monitoring, tracking, and recording body temperature for the patient 104. The temperature sensor can include both reusable portions and temporary/disposable portions. For example, the temperature sensor can include a disposable contact for affixing to the patient 104's skin under the patient 104's armpit. The temperature sensor can, for example, further include permanent portions that include temperature sensing portions, circuitry for interpreting and processing temperature data received from the patient, and a cable running from the main body of the chest sensor 102 around the chest of the patient 104 to the patient 104's armpit. In some implementations, rather than including functionality for interpreting temperature data collected from the patient 104, the temperature sensor can collect raw data that is processed by circuitry contained within the main housing of the chest sensor 102 or other portions of the system 100.

In some implementations, the chest sensor 102 includes one or more accelerometers for detecting and recording patient motion, activity, position, and posture. For example, an accelerometer included within the chest sensor 102 can track patient activity to allow a caregiver to determine if the patient 104 is receiving a sufficient level of daily exercise, or if the patient 104 is engaging in too much activity for the current physical condition of the patient 104. The accelerometer can also be used to determine if the patient 104 has fallen, or if the patient 104 has been motionless for a specified period of time. For example, the accelerometer can determine that the patient has been in a particular posture for more than a specified time period, which can allow the system 100 to identify an alarm state for the patient and send out one or more alerts to elicit a caregiver response to the patient's alarm state. The accelerometer can also be used to track patient sleep patterns, or to track the posture of the patient 104 to allow caregivers to provide recommendations for how the patient 104 can better position himself when seated, lying, standing, etc. The accelerometer could additionally provide information to caregivers that can be used to determine if the patient 104 is engaging in activities or habits that can increase the risk of re-injury or of developing complications.

The chest sensor 102 can also include circuitry and components for identifying a physical location of the patient 104. For example, the chest sensor 102 can include a GPS unit or a radio signal triangulation based location determination device. A GPS unit or other location determination circuitry included within the chest sensor 102 can be used, for example, to identify a location of a patient when the patient is not located where the patient should be at a specified time. The GPS unit can be used to locate patients suffering from dementia or other mental illnesses who are prone to wandering and becoming lost. As another example, if the accelerometer in the chest sensor 102 determines that the patient 104 has fallen, the chest sensor 102 can transmit an alert to one or more caregivers that includes the location of the patient 104 to allow the caregivers to more easily determine where the patient 104 has fallen and attend to the patient 104's needs quickly and effectively.

Other components that can be included as part of the chest sensor 102 include a power supply, buttons or other input mechanisms for receiving user input, one or more audible alarms or speakers, and display lights or a display screen. A power supply for the chest sensor 102 can take the form of a battery pack for receiving standard disposable batteries, a rechargeable battery, or a removable battery pack that can be replaced with a fully charged battery pack. The chest sensor 102 can further include input mechanisms such as, for example, buttons, keys, or a touch screen. The input mechanisms can allow the patient 104 or a caregiver to adjust settings for the chest sensor 102, perform various tests (such as sensor tests, battery power level tests, etc.) or reset one or more alarms for the chest sensor 102. For example, the patient 104 or a caregiver can silence an audible alarm of the chest sensor 102 or stop a flashing light alarm of the chest sensor 102 by pressing a button on the chest sensor 102.

The chest sensor 102 can also include one or more audible alarms or speakers. Speakers or other noise emittance units included as part of the chest sensor 102 can provide an audible alarm when a particular patient event occurs. In some instances, different types of audible alarms can indicate different patient events. For example, a first alarm sound can indicate cardiac arrest while a second alarm sound can indicate that the patient 104 has fallen and a third alarm can indicate irregular respiration for the patient 104. In some instances, buttons or other input devices of the chest sensor 102 can be used to pause or reset an audible or visual alarm. The chest sensor 102 can also include display lights, a display screen, or other display mechanisms. For example, one or more LED lights can indicate a current status of one or more vital signs of the patient 104 or a current status of one or more components of the chest sensor 102. For example, an LED can indicate that a battery of the chest sensor 102 is low, while another LED can indicate that a communications unit (e.g., wireless Bluetooth communication circuitry) is malfunctioning. As yet another example, a display screen included as part of the chest sensor 102 can provide indications of one or more vital signs or other information collected by the chest sensor 102. For example, a display screen can show one or more ECG readings for the patient 104.

In some instances, buttons or other input devices of the chest sensor can allow the patient 104 to initiate a patient distress call. For example, the patient 104 can select a button on the chest sensor 102 which can cause the chest sensor 102 to communicate a distress signal to a bedside monitor 108, or to another computing device using wireless communications and/or by communicating through a network 112. For example, when the patient 104 presses the button, the chest sensor 102 can transmit a distress signal to a computer located at a nursing station. The nursing station can then indicate to a caregiver that the patient 104 has initiated a distress call. Additionally, information related to the distress call can be recorded and stored along with an indication of a time when the distress call was made, and vital sign and other information for the patient at the time of the distress call.

In some implementations, one or more input devices of the chest sensor 102 can initiate microphone functionality of the chest sensor 102. For example, the patient 104 can select a button on the chest sensor 102 to activate a microphone included in the chest sensor 102. The microphone can allow the patient 104 to make an audio recording to, for example, indicate symptoms currently being experienced, or recently experienced by the patient 104. The audio recording can be recorded along with a time stamp of when the recording was made and stored in computer memory of the chest sensor 102 and/or another computing device in communication with the chest sensor 102. The audio recording (e.g., that includes the patient 104 reciting symptoms) can be used by one or more caregivers in diagnosing the patient 104.

In some implementations, the microphone functionality of the chest sensor 102 can be used to facilitate one-way or two-way audio communication between the patient 102 and a caregiver located at a different location. For example, the patient 104 can select a button of the chest sensor 102 to activate the microphone of the chest sensor 102 and initiate a two-way audio communication session with a caregiver located at a computing device at a different physical location than the patient 104 and the chest sensor 102. For example, the patient 104 can talk to a nurse located at a nursing station on the same floor of a hospital as the patient 104 to communicate problems, symptoms, or other information to the nurse. The nurse can communicate back to the patient 104. For example, the chest sensor 102 can include a speaker to emit audio transmitted by the nursing station to allow the nurse to provide instructions or comfort to the patient 104, or to inform the patient 104 that help is on the way.

As mentioned above, patient worn sensors included as part of the system 100 can include the wrist sensor 106. The wrist sensor 106 can be used to track and record blood pressure and blood oxygenation (SpO2) for the patient 104. As with the chest sensor 102, the wrist sensor 106 can include both reusable and disposable portions. For example, the wrist sensor 106 can include a reusable housing and circuitry for processing signals received from the patient 104 and a disposable portion for contacting the skin of the patient 104. In some implementations, the wrist sensor includes a finger sensor 107 that extends from the wrist sensor 106 and engages one or more fingers of the patient 104. The finger sensor 107 can be used, for example, to measure blood oxygenation (SpO2) for the patient 104. In some implementations, rather than being located at the wrist of the patient 104, the wrist sensor 106 can take the form of an upper arm sensor that is located at the upper arm (above the elbow) of the patient 104. The upper arm sensor can be used, for example, to measure blood pressure for the patient 104.

The chest sensor 102 can communicate with a bedside monitor 108 to convey information collected by the chest sensor 102 and/or other patient worn sensors (e.g., patient vital signs, patient activity, patient location) to the bedside monitor 108. For example, the chest sensor 102 can wirelessly communicate with the bedside monitor 108 using Bluetooth technology. As another example, the chest sensor 102 can communicate with the bedside monitor 108 using a WiFi protocol or a cellular protocol. As yet another example, the chest sensor 102 can use a wired connection to communicate with the bedside monitor 108. The communication connection between the chest sensor 102 and bedside monitor 108 can also be used to relay information from the bedside monitor 108 to the chest sensor 102. For example, the bedside monitor 108 can be used to change settings for the chest sensor 102, such as acceptable ranges for heart rate, respiratory rate, blood oxygenation, or other vital signs monitored by the chest sensor 102 and/or other patient worn sensors. As another example, the bedside monitor 108 can be used to change a frequency at which particular vital signs for the patient 104 are captured and transmitted by the chest sensor 102 and/or wrist sensor 106. As yet another example, the bedside monitor 108 can be used to change a sensitivity level of one or more vital sign reading components of the chest sensor 102 and/or wrist sensor 106.

In some implementations, the wrist sensor 106 also communicates with the bedside monitor 108 (e.g., through a wireless Bluetooth connection, other wireless connection, or through a wired connection). In some implementations, the wrist sensor 106 does not communicate directly with the bedside monitor 108, but rather transfers information to the chest sensor 102 (e.g., through a wireless or wired connection) and the chest sensor 102 then transfers information collected by the wrist sensor 106 to the bedside monitor 108 and transmits settings information and other information indicated by the bedside monitor 108 to the wrist sensor 106.

The bedside monitor 108 can allow a caregiver 110 (e.g., a nurse, doctor, orderly, physical therapist, or other caregiver) to view real-time vital signs for the patient 104, past vital signs for the patient 104, other information provided by the chest sensor 102, wrist sensor 106, and/or other patient worn sensors, or other information associated with the patient 104. For example, the bedside monitor 108 can display an ECG waveform for the patient 104 while also listing a current blood oxygenation level, blood pressure, hydration level, heart rate, respiration rate, and body temperature for the patient 104. The caregiver 110 can also use the bedside monitor 108 to make notes regarding patient care for the patient 104, make annotations for vital sign information or other patient information, send messages to other caregivers, or log patient activities. For example, the caregiver 110 can use the bedside monitor 108 to make a note that the patient 104 has experienced mild trouble breathing, or that the patient 104 is experiencing limb pain. As another example, the caregiver 110 may be a physical therapist and can use the bedside monitor 108 to log a therapy activity for the patient 104 and make notes about physical therapy progress for the patient 104. As yet another example, the caregiver 110 can use the bedside monitor 108 to adjust ranges for what is considered a "normal" or "safe" range for one or more vital signs for the patient 104. As yet another example, the caregiver 110 may be a hospital orderly and can use the bedside monitor 108 to record when the patient 104 has eaten meals, and how much the patient 104 has eaten at each meal.

The bedside monitor 108 can also be used to review notes on patient care for the patient 104 left by other caregivers, or track patient vital signs and activity for a period of time in order to assist in diagnosis or prevention of complications. The bedside monitor 108 can also convey information associated with alarm states for the chest sensor 102. For example, if any of the various vital signs or other information (such as patient motion/location) falls outside of specified "safe" limits, the chest sensor 102, wrist sensor 106, or bedside monitor 108 can initiate an alarm state. The bedside monitor 108 can alert the caregiver 110 to the alarm state through use of visual or audio alarms. In some scenarios, different visual or audio alarms can be used for distinct types of alarm states, or for varying emergency levels associated with different alarm states. In some implementations, alarm states can be tiered based on the severity of an alarm state, with some alarms being identified as more important (and/or in need or more immediate attention from a caregiver) than others. For example, if the chest sensor 102 detects cardiac arrest, this can be classified as a high level emergency requiring immediate attention, while if the wrist sensor 106 detects a slightly elevated blood pressure, this can be identified as a low level alarm state that does not need to be addressed until the next time a caregiver checks in with the patient 104. A display of the bedside monitor 108 can indicate various alarm states to the caregiver 110, as well as the relative importance or level of each alarm state. The caregiver 110 can then use the bedside monitor 108 to view additional information associated with each alarm state, including changes in vital signs or other patient associated information that prompted initiation of the alarm state.

In some implementations, the chest sensor 102, wrist sensor 106, and/or other patient worn sensors can include circuitry for processing vital sign information and other information recorded by the sensors to identify when one or more alarm states have occurred. In some implementations, the patient worn sensors transmit raw, pre-processed vital sign information and other information collected in association with the patient 104 to the bedside monitor 108 and the bedside monitor 108 analyzes the raw information to determine various vital signs and other information for the patient 104 and identify if any alarm states are present (e.g., by identifying if any vital signs or other signals have deviated from an acceptable range). In still other implementations, other portions of the system 100 may be used to analyze vital sign and other information collected by the chest sensor 102 and wrist sensor 106 to identify alarm states associated with the patient 104.

In some implementations, an alarm state for the patient 104 can be identified by comparing one or more vital signs collected for the patient 104 to threshold values. For example, the patient 104's heart rate can be compared to a threshold heart rate value, if the patient 104's heart rate falls below the threshold value, one or more components of the system 100 can automatically determine that the patient is experiencing cardiac arrest. The system 100 can then send alerts to one or more caregivers indicating the cardiac arrest alarm state for the patient 104. For example, an alert can be sent to one or more caregivers within a predetermined proximity of the patient 104, a supervising nurse for a hospital ward in which the patient 104 is located, and a general care physician responsible for general care for the patient 104. An alert can also be sent to a cardiologist currently on duty at the healthcare facility where the patient 104 is located.

In some implementations, collected vital signs can be compared to threshold values to not only determine a type of alarm state, but also to identify a severity of an alarm state. For example, a patient experiencing a respiration rate that is slightly above the preferred range for the patient can be identified as having a respiratory alarm state of a tier 2 level while a patient experiencing a respiration rate that deviates significantly from a preferred range can be identified as having a respiratory alarm state of a tier 1 level (e.g., a higher urgency level). As indicated in the preceding example, alarm states can be divided into different tier levels. As another example, information collected by an accelerometer included in the chest sensor 102 can indicate that the patient 104 has fallen. If the distance and velocity of the fall can be compared to threshold values to identify a severity for the fall and associate an alarm state tier level for the fall. For example, a slow fall from a height of two feet can have a severity level of tier 2 while a quick fall from a height of five can be assigned a severity level of tier 1.

In addition to communicating with the chest sensor 102, wrist sensor 106, and/or other patient worn sensors, the bedside monitor 108 can also communicate with one or more central servers 113 through a network 112. The central server 113 can collect information provided by the bedside monitor 108, other bedside monitors, various sensors, and other computing terminals. The central server 113 can comprise multiple servers that are co-located, or multiple servers located at distinct geographic locations to provide so called "cloud" storage for information stored by the system 100. The one or more central servers 113 can be accessed through the network 112 from many different locations by various devices, including the bedside monitor 108, other bedside monitors and computing devices located at the same hospital as the bedside monitor 108, and various bedside monitors and other computing devices (e.g., mobile phones, personal computers, tablet devices, etc.) located at other physical locations.

Information collected by the central server 113 can be accessed at a central server station 114. For example, a caregiver 116 or other hospital personnel can use the central server station 114 to access information for the patient 104, other patients, or other hospital or healthcare administrative functions. The network 112 can be an intra-hospital local area network (LAN) such as a WiFi network, a wide area network (WAN) such as the Internet, or any combination of LAN and WAN networks. The bedside monitor 108 can connect to the network 112 using a wireless protocol such as WiFi or a cellular communication protocol, or through a wired connection. In some implementations, the central server station 114 may be located at a distinct facility from the patient 104 and bedside monitor 108.

The central server station 114 can allow the caregiver 116 to monitor vital signs, activities, and other information for the patient 104 from a remote location. The central server station 114 can additionally allow the caregiver 116 to observe information for multiple patients within a healthcare facility or system simultaneously. In some implementations, all information collected by the patient worn sensors (e.g., the chest sensor 102 and the wrist sensor 106) and all information entered using the bedside monitor 108 is stored by the central server 113 and is accessible through the central server station 114. In some implementations, the caregiver 116 can receive alarms or alerts associated with the patient 104 at the central server station 114 and take appropriate actions to dispatch one or more caregivers to address the alarm situation. In some implementations, the system 100 can automatically recognize an alarm state for the patient 104 and alert an appropriate caregiver to respond to the situation. For example, the bedside monitor 108 can analyze information received from the chest sensor 102 to determine that the patient 104 is choking. The bedside monitor 108 can recognize this as an emergency level alert, and transmit this information to the central server 113. The central server 113 can then identify one or more caregivers within close proximity to the patient 104 and alert them that the patient 104 is choking.

The alerts can be sent to the one or more caregivers, for example, through bedside monitors with which the caregivers are currently interacting, computer terminals in communication with the central server 113, mobile devices carried or worn by the caregivers, or alarms or displays located throughout a hospital or healthcare facility where the patient 104 is located. The central server 113 can also transmit alert information regarding the patient 104 to the central server station 114 to notify the caregiver 116 as well as the beside monitor 108 (which is associated with the chest sensor 102 worn by the patient 104) to alert the caregiver 110 or perhaps one or more other caregivers in the vicinity of the bedside monitor 108. This automated recognition of an alarm state for the patient 104 and routing of the alarm to caregivers within close proximity to the patient 104 can reduce the time taken to respond to and resolve the emergency, thereby reducing adverse effects for the patient 104.

In some implementations, in addition to information collected by the various patient worn sensors (such as the chest sensor 102, wrist sensor 106, and/or other patient worn sensors) the bedside monitor 108 can include functionality for collecting information related to the patient 104. For example, the bedside monitor 108 can include one or more cameras for monitoring movements, posture, and other aspects of the patient 104. The cameras can be built in to the bedside monitor 108, attached to the bedside monitor 108 as peripheral devices, or separate devices in wired or wireless communication with the bedside monitor 108. A camera of the bedside monitor 108 can be positioned to face the patient 104 while the patient 104 is located in the bed and monitor movements of the patient 104. This information can be used to recognize alarm states for the patient. For example, the bedside monitor 108 (or another computing device of the system 100, such as the central server 113) can analyze video images captured by the camera to identify if the patient 104 has fallen out of the bed. As another example, the camera can be used to identify that the patient 104 is not located in the bed at a time when the patient 104 is expected to be located in the bed. If the bedside monitor 108 detects that the patient 104 has been out of bed for longer than a threshold period of time, the bedside monitor 108 can recognize this as an alarm state and alert a caregiver to the situation.

As yet another example, the camera of the bedside monitor 108 can determine that the patient 104 is awake. Stored information for the patient 104 can indicate that the patient 104 should currently be under a medication induced sleep. The bedside monitor 108 can recognize that the patient 104 being awake during a period when the patient 104 should be asleep as an alarm state. As yet another example, the camera can be used to recognize that a comatose patient is awake and moving. The bedside monitor 108 can recognize this as an alarm state and alert a caregiver to check on the now awake patient.

The bedside monitor 108 can further include one or more accelerometers for determining an orientation of the bedside monitor 108. This orientation information can further be used to determine an orientation of various images captured by the camera of the bedside monitor 108. For example, the bedside monitor 108 may be positioned at various different angles depending on how the bedside monitor 108 is positioned with respect to the patient 104. For example, the bedside monitor 108 may be connected to a support post, affixed to a railing of the patient 104's bed, affixed to the wall, or placed on a table or bedside stand. Additionally the bedside monitor 108 may not necessarily be completely flush on a surface that is supporting the bedside monitor 108. The orientation of the bedside monitor 108 can differ depending on how the bedside monitor 108 is supported. The accelerometers can be used to determine the bedside monitor 108's orientation and thereby determine the orientation of images captured by the camera of the bedside monitor 108.

In some implementations, the chest sensor 102 also includes one or more accelerometers than can determine movements of the chest sensor 102 and orientation of the chest sensor 102. When chest sensors of the system 100, such as the chest sensor 102, are affixed to patients, the chest sensors may have various different orientations when the patients are standing or sitting straight up due to differences in the slope of the chest of each patient or placement location of the chest sensors on each patient. Therefore, the accelerometers of the chest sensor 102 may not be able to accurately determine when the patient 104 is standing or sitting straight up (or lying flat) due to unknown factors such as the slope of the patient 104's chest, or the exact position of the chest sensor 102 on the patient 104. The bedside monitor 108 (or another computing device of the system 100) can use accelerometer information from the accelerometers of both the chest sensor 102 and the bedside monitor 108 as well as image data captured by the one or more cameras of the bedside monitor 108 to calibrate the chest sensor 102 to allow accurate position/posture of the patient 104 to be detected using the accelerometers of the chest sensor 102.

For example, the camera of the bedside monitor 108 can capture image data of the patient 104 while the chest sensor 102 is affixed to the patient 104. The bedside monitor 108 can use accelerometer data collected by accelerometers of the bedside monitor 108 to determine an orientation of the bedside monitor 108, and consequently an orientation of the captured image data. The bedside monitor 108 can then identify the orientation of the patient 104 within one or more of the images (e.g., sitting straight up, inclined at a 30 degree angle, lying down with the torso elevated to 5 degrees above horizontal, etc.). The bedside monitor 108 (or another computing device of the system 100) can then compare accelerometer data collected by the chest sensor 102 at the time that a particular image was taken to the identified orientation/posture of the patient 104 in the particular image to calibrate the accelerometers of the chest sensor 102 with respect to the patient. After calibration, the accelerometer data collected by the accelerometers of the chest sensor 102 can be used to determine orientations/postures of the patient 104 even when the patient 104 is not in view of the camera of the bedside monitor 108. In some implementations, tracked posture/position data for the patient 104 can be used in diagnosing or providing treatment for the patient. For example, a physical therapist can use tracked posture data to alter a physical therapy routine for the patient 104 to correct detected incorrect posture. Detected posture/position information can also be used to detect alarm states. For example, detection of an unexpected posture by the accelerometers of the chest sensor 102 can indicate a problem (e.g., the patient 104 is partially hanging out of bed, or the chest sensor 102 has become detached from the patient 104). As another example, in some cases a tracked angle of incline for the patient 104 can be used by a clinician to determine a level of severity of a heart failure experienced by the patient 104.

In addition to detecting movements of the patient 104 and collecting information for calibrating accelerometers of the chest sensor 102, the one or more cameras of the bedside monitor 108 can be used to monitor other aspects of the patient 104. For example, a camera of the bedside monitor 108 can monitor the patient 104 for changes in color. For example, the camera can monitor the skin tone of the patient 104 after surgery to determine if the patient 104 is returning to a "normal" color within an acceptable time frame after surgery. If the change in color of the patient 104 does not proceed according to schedule, the bedside monitor 108 can recognize this as an alarm state and alert one or more caregivers. As another example, the bedside monitor 108 can use collected image data to monitor a level of jaundice for the patient 104 and recognize an alarm state if the chest sensor 102's color does not improve, or worsens, over a period of time.

The camera of the bedside monitor 108 can also be used identify one or more dangerous or undesirable conditions for the patient 104. For example, the bedside monitor 108 can use the camera to identify that a guardrail for the patient 104's bed is down (e.g., a caregiver forgot to put the rail back up after assisting the patient 104 into bed). The bedside monitor 108 recognize this as an alarm state and notify an appropriate caregiver. As another example, if accelerometer data collected by the chest sensor 102 indicates that the patient 104 has fallen out of bed, the camera of the bedside monitor 108 can be used to verify that the patient 104 has fallen out of bed. In some cases, the camera of the bedside monitor 108 can provide a video feed to one or more caregivers (e.g., to a nurse positioned at a nursing station in the same ward as the patient 104) to allow the caregivers to periodically check in on the patient 104 without having to physically enter the patient 104's room.

Other information that can be collected by one or more sensors or devices built into or in communication with the bedside monitor 108 can include environmental temperature, environmental humidity, noise level, light level, carbon monoxide detection, or smoke detection. For example, the bedside monitor 108 can identify that environmental temperature near the patient 104 has fallen below an acceptable level and alert a caregiver or maintenance worker to the change in temperature. As another example, the bedside monitor 108 can detect that environmental humidity has dropped below a threshold value.

In some implementations, caregivers associated with the patient 104 can be classified into different caregiver categories. For example, first tier caregivers can be identified as caregivers who are responsible for the immediate or day to day care of the patient 104, while second tier caregivers can be identified as caregivers responsible for more generalized supervision of the patient 104's recovery or treatment. For example, an attending physician for a ward where the patient 104 is located could be identified as a first tier caregiver for the patient 104 while a speech therapist responsible for meeting with the patient and working on speech skills once per week could be classified as a second tier (or in some cases, even a third tier) caregiver for the patient 104. As another example, an immediate relative of the patient 104 who responsible for care of the patient 104 when the patient is at home can be identified as a third tier caregiver for the patient 104. The same caregiver can have different caregiver classification levels for different patients. For example a physical therapist can be a first tier caregiver for a patient with which the physical therapist meets several times per day for long periods, while the physical therapist can be a second tier caregiver for a patient who only meets with the physical therapist once per week.

In some implementations, when a patient event (such as an alarm state identified based on vital sign information, or another patient event) occurs for the patient 104, different alerts can be sent to different caregivers. In some implementations, the different alerts can be sent to caregivers based on the caregiver classifications for the caregivers. For example, a detailed alert that includes details on a particular alarm state for the patient 104 and instructions on how to respond to the alarm state can be transmitted to an attending physician on duty at a ward where the patient 104 is located (a first tier caregiver) while a less detailed alert that merely indicates the alarm state and a time when the alarm state occurred can be sent to the patient 104's general care family doctor (a second tier caregiver for the patient 104). As another example, components of the system 100 can determine that the patient 104 is choking based on vital sign information collected by the chest sensor 102. The system 100 can send an urgent alert to a nurse located within a close proximity to the patient 104 that indicates that the patient is choking and instructing the nurse to clear the patient 104's airway. A different alert can be sent to the patient 104's identified emergency contact (e.g., parent, spouse, sibling, etc.) that indicates that the patient experienced a choking situation, and perhaps also indicating that the choking situation was addressed and the patient 104 is no longer in danger.

As yet another example, an alarm state can be triggered because the patient 104 is vomiting. The system 100 can send an alert to a nurse or orderly located within close proximity to the patient 104 indicating that the patient is vomiting, potential reasons why the patient is vomiting, and recommended steps to deal with the situation. A different alert can be sent to a pharmacist associated with the patient indicating that the vomiting occurred and potentially recommending that the pharmacist reassess the patient 104's medication regime. In another example, an accelerometer included in the chest sensor 102 can convey information to the bedside monitor 108 that allows the bedside monitor 108 to determine that the patient has fallen. The system 100 can issue an alert to an orderly located near the patient 104 that informs the orderly of the fall and instructs the orderly to assist the patient 104. A second alert can be sent to the patient 104's physical therapist indicating that the patient 104 fell and indicating a time when the fall occurred. This information can then be used by the physical therapist to adjust treatment for the patient 104.

As described above, various different alarm states can be ranked into various tiers depending on the urgency/severity of the various alarm states. For example, if the chest sensor 102 detects that the patient 104 is experiencing cardiac arrest, this can be classified as a first tier alert, while a determination that the patient 104 has fallen can be classified as a second tier alert, a determination that the patient 104 is breathing irregularly can also be classified as a second tier alert, and a determination that the patient 104 has been immobile for more than a threshold period of time can be classified as a third tier alert. Different tiered alarm states or different types of alarm states can cause the system 100 to send alerts to different caregivers, based on a determination as to which caregivers are best suited to deal with a particular alarm state. For example, a determination that the patient 104 has fallen can lead the system to send an alert to a caregiver having the closest proximity to the patient 104 since someone close to the patient 104 is best able to address the situation quickly, and helping a patient after a fall does not inherently require specialized skill or knowledge. However, if the patient is experiencing cardiac arrest, a different set of caregivers, such as one or more nurses and doctors located near the patient 104 to be alerted to the alarm state.

In some implementations, if a particular alarm state for the patient 104 is not addressed within a specified period of time, the system 100 can escalate alerts that are issued by the system 100. For example, the central server 113 can identify an alarm state for the patient 104, either by receiving a notification from the bedside monitor 108 of the alarm state, or by identifying the alarm state by processing information collected by the chest sensor 102 and/or wrist sensor 106. The central server 113 can identify a first set of caregivers to alert to the alarm situation. The central server 113 can transmit alerts regarding the alarm state for the patient 104 to the identified first set of caregivers by, for example, sending alerts to mobile devices of each of the first set of caregivers, or by sending alerts to bedside monitors or stations at which caregivers are located. Other methods of alerting the caregivers include text messages or automated phone calls. Subsequently, if the central server 113 determines that no one has responded to the alarm state within a specified period of time, the central server 113 can identify a second set of caregivers to inform about the alarm state and transmit alerts regarding the alarm state to the second set of caregivers. In some implementations, the alerts sent to the second set of caregivers can have a heightened alert state (compared to the alerts sent to the first set of caregivers) since a period of time has elapsed since the first set of alerts was transmitted. Additionally, the alerts sent to the second set of caregivers can include different information from the alerts sent to the first set of caregivers. For example, the alerts sent to the second set of caregivers can indicate that alerts had previously been sent to other caregivers and that none of them had responded, or that the alarm state has still not been addressed. In some implementations, alerts sent to the first and/or second set of caregivers can include instructions on how to respond to the alarm state.

In some cases, alerts can also be retransmitted to caregivers within the first set of caregivers at specified intervals (in case one or more of the first set of caregivers had merely failed to notice the initial alert transmission). Escalation and transmittal of additional alerts to additionally identified sets of caregivers can occur periodically until the alarm state is addressed. For example, a caregiver included in the second set of caregivers can respond to an alert indicating that the patient 104 is choking. The caregiver can react to the situation by removing the obstruction from the patient 104's airway, verify that the patient 104 is in a stabilized condition, and then use the bedside monitor 108 to indicate that the alarm state has been addressed and resolved. Upon receiving the indication that the alarm state has been addressed, the central server 113 can cease sending additional alerts regarding the alarm state.

Alerts regarding particular patient alarm states can be routed based on a number of factors, including the nature of the emergency that prompted the alarm state, severity of the alarm state, proximity of caregivers to the patient 104, specialized knowledge or skill of particular caregivers (including correlation of specialized knowledge or skill with the particular nature of the emergency), the type of clinicians available, length of time since the alarm state was first detected, time of day, location of the patient (e.g., at the healthcare facility, at home, near a different healthcare facility, etc.), caregiver classification of caregivers with respect to the patient 104, or current status of caregivers. For example, if a first doctor is currently involved in responding to an emergency situation for a first patient, if an alarm state occurs for a second patient near the first doctor, the system 100 can determine that the first doctor is already engaged and therefore unavailable to respond to the alarm state associated with the second patient. The system 100 can thereafter identify one or more other caregivers that can potentially respond to the alarm state for the second patient and send alerts to these other caregivers.

In some implementations, alerts can be generated in response to detection that a patient is in an unexpected location, or that the patient has been in a particular location for longer than a specified period of time. For example, a patient can be located in a recovery room after a surgery. The patient can be scheduled to be moved to a room in a general ward of the hospital within a certain time frame (e.g., under 8 hours). One or more computing devices of the system 100 can identify that the patient has been located in the recovery room for longer than eight hours and generate an alert to provide to one or more caregivers indicating that the patient is still located in the recovery room. As another example, one or more computing devices of the system 100 can determine that the patient was supposed to be discharged from the hospital within a particular time window. If the patient is identified as still being located within the hospital after the specified time window has elapsed, the system 100 can generate an alert and provide the alert to one or more caregivers indicating that the patient was supposed to have been discharged. As yet another example, an alert can be generated and provided to one or more caregivers if a patient is identified as being immobile in a stairwell for more than a specified period of time (e.g., one minute).

In some implementations, alerts regarding situations other than patient associated alarm states can also be sent to caregivers or other users of the system 100. For example, an alert indicating that the bedside monitor 108 has lost communication with the chest sensor 102 can be sent to the caregiver 110. As another example, an alert indicating that a battery of the chest sensor 102 is law can be sent to the caregiver 110. As yet another example, an alert indicating that the chest sensor 102 is not properly collecting information necessary for one or more vital sign determinations for the patient 104 can be transmitted to the caregiver 110. In this example, the caregiver 110 can address the problem by adjusting contacts of the chest sensor 102 so that they properly contact the skin of the patient 104, or by replacing the chest sensor 102 with a properly functioning chest sensor.

In some implementations of the system 100, the chest sensor 102, wrist sensor 106, and/or other patient worn sensors can obviate the need for the bedside monitor 108 by connecting directly to the network 112 (e.g., using a WiFi or other wireless protocol) to transfer vital sign and other information to the central server 113. The information transferred to the central server 113 through the network can then be accessed at the central server station 114 and other terminals connected to the network 112. In some implementations, the bedside monitor 108 serves as a dummy terminal that receives information from the central server 113 and displays a graphical user interface dictated by the central server 113 rather than receiving information directly from the chest sensor 102 and/or other patient worn sensors.

In some implementations, information for the patient 104 (such as vital signs, alarm states, treatment information, biographical information, etc.) can be accessed using other devices in communication with the central server 113 and/or bedside monitor 108. For example, patient information can be sent to a mobile device (such as a smart phone, tablet or laptop) owned by the caregiver 110 or another caregiver associated with the patient 104. As another example, the caregiver 110 can access the central server 113 (e.g., by using the bedside monitor 108 or another computing device) and indicate that the caregiver 110 wishes to receive updates for the patient 104. The caregiver 110 can then be associated with the patient 104 (for example, by linking a caregiver profile for the caregiver 110 to a patient profile for the patient 104). When important information regarding the patient 104 (such as alarm states, or significant changes in treatment plans) are received by the central server 113, the central server 113 can automatically send this information to a device associated with the caregiver 110, such as the caregiver 110's mobile phone.

In some implementations, a caregiver associated with the patient 104 can use a computing device to communicate with the central server 113 and access information for the patient 104. For example, a caregiver can access information for the patient 104 if the caregiver has proper permission to access the information. The caregiver can indicate permission to access the information by entering an access code, or by accessing a profile for the caregiver that has previously been associated with a patient profile for the patient 104. In some implementations, information associated with the patient 104 can be accessed from a number of different bedside monitors or central server stations. Such an information access scheme can allow caregivers and other users of the system 100 to access information for multiple patients. For example, a doctor can be in charge of monitoring the status of a number of patients. The doctor can use a PC to access the central server 113 and view vital sign information, alert information, and other information for each of the multiple patients. The information for the multiple patients can be arranged in a newsfeed that allows the doctor to easily access and review the most pertinent patient information, while also providing the ability for the doctor to access additional information for each patient that is not identified by the system 100 as being the most relevant.

The caregiver 110 can additionally use the bedside monitor 108 to access information associated with the patient 104 that has been entered into the system 100 but not provided by the chest sensor 102 or other patient worn sensors. For example, the caregiver 110 can use the bedside monitor 108 to access information associated with the patient 104 regarding treatment or procedures that occurred at locations other than the current location of the patient 104. In one example, the caregiver 110 can use the bedside monitor 108 to access and review information stored at the central server 113 regarding interactions between the patient 104 and emergency room staff to assess a current status for the patient 104. As another example, the caregiver 110 can review notes left by an anesthesiologist at a different bedside monitor for the patient 104 regarding specific vital signs or other behavior for the patient 104 to observe during a specified post-surgical procedure time period for the patient 104.

In some implementations, the central server 113 can interface with computing systems outside of the system 100 to access additional information for the patient 104. For example, the central server 113 can access electronic medical records (EMRs), electronic health records (EHRs), or picture archiving and communication system (PACS) information for the patient 104 containing healthcare information for the patient regarding past treatment, procedures, care plans, diagnoses or other healthcare related information for the patient 104 which may or may not be associated with a healthcare facility associated with the system 100.

As discussed above, the various components of the system 100 can allow caregivers (including the caregivers 110 and 116) to more efficiently coordinate patient care and more seamlessly transition a patient from one location to another, from one environment to another, or from one set of caregivers to another. For example, caregivers can use the system 100 to make notes regarding patient care which can be stored along with patient vital sign and other information. For example, the caregiver 110 can make a note about the patient 104's eating habits. As another example, the caregiver 116 can use the central server station 114 to enter notes for the patient 104 that are, for example, based on reviewing and assessing information received from the bedside monitor 108 and other sources and stored at the central server 113. The notes can then be viewed by other caregivers when the caregivers access information about the patient 104 (e.g., using the central server station 114, the bedside monitor 108, another bedside monitor, a mobile device, or another computing device in communication with the network 112) to allow the other caregivers to adjust one or more aspects of the patient 104's treatment plan. In some instances, a note or message can be addressed to the attention of one or more other caregivers. For example, a the caregiver 110 can make a note that the patient 104 had a particular reaction after taking medication and set the note to the attention of a pharmacist responsible for care of the patient. The pharmacist can receive an alert (e.g., via the pharmacist's mobile phone) that a new note has been addressed to his attention, review the note, and review other information associated with the patient 104 to best determine if a change to the patient 104's medication schedule needs to be made.

In some implementations, the central server 113 can include information other than information directly related to patient care. For example, the central server 113 can store information related to healthcare facility maintenance and inventory (e.g., for medical supplies, medical devices, medication, or routine items such as light bulbs and batteries). This information can be accessed from computing devices included in the system 100 that are in communication with the network 112. The system can further include functionality for tracking maintenance and inventory, including scheduling maintenance, tracking maintenance progress, ordering new inventory as supplies are depleted, tracking supplier, vendor, and service provider information, and tracking maintenance and inventory budgets. The central server 113 can also store insurance information for patients, payment information for patients, or other patient information that is only tangentially related to patient care. Additional functionality that can be provided by the central server 113 or other components of the system 100 includes employ payroll and staff scheduling.

In some implementations of the system 100, multiple patient worn sensors are associated with multiple respective patients and each of the patient worn sensors is configured to sync with one or more bedside monitors or intermediary devices (e.g., using Bluetooth or another wireless communication protocol). In some implementations, the patient worn sensors can communicate with bedside monitors or other devices using wired connections. In some implementations, some or all of the patient worn sensors are configured to communicate directly with the network 112 (e.g., using WiFi or another wireless communication protocol). Information collected by the multiple patient worn sensors can be routed through the network to the central server 113 and stored. The information can then be accessed by components of the system 100. For example, the caregiver 116 can access information collected by the multiple patient worn sensors at the central server station 114 to monitor statuses of the patients associated with the multiple patient worn sensors.

In some implementations, multiple bedside monitors included in the system 100 can communicate directly with each other to create network redundancy. For example, the network 112 may be down for a period of time, or the bedside monitor 108 and other bedside monitors of the system 100 may be unable to communicate with the network 112 for a period of time. The bedside monitor 108 may communicate with the central server 113 and other computing devices of the system 100, for example, through a LAN. The LAN may experience an outage and be unavailable for a period of time. The bedside monitors of the system 100 can detect the outage and each bedside monitor can establish direct communications with one or more other bedside monitors (or other computing devices of the system 100) to form an ad hoc backup network for conveying patient information and other information among bedside monitors and other computing devices of the system 100. For example, each of the bedside monitors can use wireless communication capabilities (e.g., Bluetooth or WiFi communication capabilities) to communicate with other bedside monitors within range.

In many use cases, the bedside monitors will be positioned somewhat regularly throughout a hospital or other medical care environment. For example, there would generally be one or two bedside monitors located in each patient room as well as computing devices of the system 100 having wireless communication capabilities positioned at nursing stations and other area throughout the hospital. The spatial distribution of the bedside monitors can allow the bedside monitors to relay information through a series of bedside monitors (and other computing devices) to allow information to be transmitted to be transmitted between devices that are physically further apart from each other than could normally be spanned by standard short range wireless communication protocols.

In some implementations, some of the bedside monitors can be designated as hubs and route information to other hub bedside monitors, while other client bedside monitors send information only to a hub bedside monitor within wireless communication range. Such an ad hoc network can route alerts, patient information, and other notifications to the appropriate devices (such as computers located at nursing stations, or a computing device associated with an appropriate caregiver).

In some implementations, if a network failure is detected, alerts and/or messages identified as having high importance can be routed through the ad hoc network for presentation at multiple computing devices to ensure that the issue is addressed. For example, if a chest sensor of a patient identifies that the patient is experiencing heart failure, the bedside monitor in communication with the chest sensor of the patient can send an alert to all bedside monitors (and other computing devices) within communication range, and those devices can then route the alert to other computing devices, which can route the alert to still other computing devices, and so on. Each bedside monitor (or nursing station computer, etc.) that receives the alert can indicate the alert to anyone nearby. For example, all bedside monitors that receive the alert can sound an audible alarm and indicate that the patient is experiencing cardiac arrest and also indicate the location of the patient (e.g., room 317). While such a blast communication system for alerts may not be ideal under normal operating conditions, such a system can be employed when the network 112 is unavailable to get the alert to as many caregivers as possible to ensure that one or more caregivers is able to quickly respond to the patient's cardiac arrest.

In some implementations, some information deemed low priority can be stored by local bedside monitors for transmission after the network 112 is restored. For example, tracked vital sign data for the patient 104 that are all within acceptable ranges can be stored at the bedside monitor 108 for later transmission to free up communication capacity of the ad hoc bedside monitor to bedside monitor network for important alerts and notifications.

In some implementations, a different set of caregivers is alerted to alarm states for the patient 104 when the network 112 is down and an ad hoc network is employed than the set of caregivers who would be alerted when the network 112 is functioning properly. For example, an alert for the patient 104 that might normally be sent to a specialist at a remote location when the network 112 is functioning normally can be instead routed to a nearby caregiver when an ad hoc bedside monitor to bedside monitor network is employed.

In use, one or more patient worn sensors (such as the chest sensor 102 and wrist sensor 106) can be associated with the patient 104 upon admittance of the patient 104 to a healthcare facility, or shortly after admittance of the patient 104 to the healthcare facility. In some implementations, if the patient 104 has entered the healthcare facility during an emergency situation (e.g., cardiac arrest, severe car accident, etc.) the patient worn sensors can be issued to the patient 104 after the emergency situation has been addressed and the patient 104 has been stabilized. In some implementations, the patient 104 can be associated with a unique patient identifier ("ID"). The patient ID can be as simple as the patient 104's name, a unique number assigned to the patient 104, a unique combination of numbers, letters, and other characters, or any other unique identifier associated with the patient 104. If the patient 104 has previously interacted with the healthcare facility, the system 100, or a related system, the caregiver 110 can look up the unique identifier for the patient 104 by, for example, entering the patient 104's name at the bedside monitor 108. The caregiver 110 can then access patient information for the patient 104. Patient information can include biographical information such as name, age, weight, height, address, contact information, family members, emergency contacts, etc. as well as healthcare information regarding past (or present or future) healthcare events, treatments, procedures, care plans, etc. for the patient 104. In some implementations, the caregiver 110 can access a patient profile for the patient 104 (for example, using the patient ID for the patient 104). The patient profile can include any of the above listed information for the patient 104. The patient profile can also indicate caregivers associated with the patient 104, such as doctors who have performed surgery on the patient 104, doctors scheduled to perform future procedures on the patient 104, one or more caregivers responsible for the primary care of the patient 104, emergency room doctors and attendants who handled initial emergency care for the patient 104, and other caregivers associated with the patient 104.

If the patient 104 has not previously interacted with system 100 or a related system, a new unique ID can be assigned to the patient 104 by one or more components of the system 100 (for example, by the bedside monitor 108 or the central server 113.) Biographical, healthcare, and other information for the patient 104 can then be entered (e.g., using the bedside monitor 108 or central server station 114) and stored at the central server 113.

When the patient worn monitors (such as the chest sensor 102 and wrist sensor 106) are initially provided to the patient 104, the patient worn sensors can be associated with the patient 104 by associating the patient worn sensors with the unique ID for the patient 104. For example, the chest sensor 102 can be synced with the bedside monitor 108. The caregiver 110 can then use the bedside monitor 108 to associate the chest sensor 102 with the patient 104. After the chest sensor 102 is associated with the patient 104, the chest sensor 102 can identify the patient 104 to other components of the system 100, such as other bedside monitors, or other monitor stations.

The bedside monitor 108 can sync with the chest sensor 102, for example, by searching for devices within a specified distance of the bedside monitor 108, displaying a list of nearby devices (such as the chest sensor 102, the wrist sensor 106, and one or more other patient worn sensors worn by other nearby patients), and allowing the caregiver 110 to select the chest sensor 102 from the list of displayed devices. After syncing, the caregiver 110 can associate the chest sensor 102 with the patient 104's unique patient ID. As another example, the caregiver 110 can sync the bedside monitor 108 with the chest sensor 102 by entering a unique sensor ID for the chest sensor 102 at the bedside monitor 108. The unique sensor ID can be, for example, printed on the surface of the chest sensor 102. In some implementations, the bedside monitor 108 is synced with the chest sensor 102 using a special scanning device in communication with the bedside monitor 108. The caregiver 110 can use the scanning device to scan the chest sensor 102 (e.g., by detecting a signal being transmitted by a component of the chest sensor 102, scanning an RF ID tag, or by reading a barcode printed on the chest sensor 102). The bedside monitor 108 can use information from the scanning device to identify the chest sensor 102 and sync with the chest sensor 102. In some implementations, the bedside monitor 108 can include a scanning device that is incorporated into the design of the bedside monitor 108. For example, the bedside monitor can be a tablet device that has one or more built in cameras that can be used to scan the chest sensor 102.

In some implementations, the bedside monitor 108 can automatically sync patient worn sensors or other devices with which the bedside monitor 108 has previously synced whenever the patient worn sensors and other devices are within a communication range of the bedside monitor 108. For example, the chest sensor 102 can be synced with the bedside monitor 108 using one of the above described techniques, or another technique. The patient 104 can then leave a communication range of the bedside monitor 108, for example by going to a hospital cafeteria to eat lunch or going to a physical therapy area of the healthcare facility. The patient 104 can then return to the communication range of the bedside monitor 108. The bedside monitor 108 can automatically detect that the chest sensor 102 has reentered the communication range of the bedside monitor 108, that the bedside monitor 108 and chest sensor 102 had previously been synced, and then sync with the chest sensor 102. In some implementations, the bedside monitor 108 automatically syncs with all patient worn sensors within a specified communication range that are capable of communicating with the bedside monitor 108. For example, the bedside monitor 108 can sync with patient worn sensors for multiple patients located in the same room and display information received from each of the sensors.

In some implementations, patient worn sensors can sync with any monitor (such as a bedside monitor) within a specified communication distance. In some implementations, a patient worn sensor can identify a nearest monitor from among several monitors (e.g., by strength of communication signal) and automatically sync with the identified nearest monitor. In some implementations patient worn sensors are capable of syncing with multiple monitors simultaneously. In some implementations, syncing activity of a patient worn sensor can be used to track movements of a patient. For example, each monitor can be associated with a particular physical location. In this example, the bedside monitor 108 might be associated with room 309 of the healthcare facility. In some implementations, when monitors are moved, they become associated with a new physical location. Continuing with this example, the patient 104 can leave a room in which the bedside monitor 108 is located (i.e., room 309).

As the patient 104 walks down a hallway, monitors positioned in the hallway or in other rooms of the healthcare facility can detect the chest sensor 102. These monitors can indicate to the central server 113 that the chest sensor 102 was within communication range, and also indicate the time at which this occurred. As the patient 104 continues to move, the chest sensor 102 can continually sync and un-sync with various monitors at various different times. This continual syncing and un-syncing of the chest sensor 102 can be used to track movements of the patient 104 within the healthcare facility. This information can be used to identify a location for the patient 104 if the patient 104 cannot be found, or if the patient 104 has failed to arrive for a scheduled appointment or treatment.

Additionally, such tracking of patient movement can be used to verify that the patient 104 arrived at a correct location for a scheduled procedure, treatment, or therapy. For example, the system can log that the chest sensor 102 synced with a monitor located at a physical therapy facility within the healthcare facility during a particular time period. This information can be checked by the system 100, or by a caregiver to verify that the patient 104 was present for a previously scheduled physical therapy appointment. As another example, the central server 113 can use patient location information for the patient 104 to identify that the patient 104 has failed to arrive for a previously scheduled therapy appointment. The central server 113 can then take actions in response to this determination such as sending an alert to a caregiver that the patient 104 has not arrived for a therapy session, or sending a reminder to the patient 104. For example, a reminder that is viewable by the patient 104 can be sent to the bedside monitor 108, a different monitor that is currently synced with the chest sensor 102, or the patient 104's mobile phone.

A detailed use case that can be implemented utilizing the various components of the system 100 will now be described. The patient 104 can experience a medical emergency and enter an emergency department (ER) of a healthcare facility. Upon entering the ER, the caregiver 110 can perform triage for the patient 104 to identify the patient 104's immediate needs and perform initial diagnosis for the patient 104. For example, the patient 104 may be complaining of chest pains. The caregiver 110 can register the patient 104 in the system 100 using the bedside monitor 108. In some implementations, this can include creation of a patient profile for the patient 104. The caregiver 110 can enter care information for the patient 104 in the form of notes (for example, a note indicating that the patient 104 is experiencing chest pain). The system 100 automatically pushes the registration data to the central server 113 where the patient data can be stored as an electronic medical record (EMR) for the patient 104. The patient 104 is outfitted with the chest sensor 102 and the wrist sensor 106 to track vital signs for the patient 104. This can allow the ER physician (caregiver 110) to begin to immediately assess the patient 104's baseline status. For example, the ER physician may see nothing immediately wrong from the patient 104's vital signs, but can nonetheless request that the patient 104 be placed on observation for 2 hours while additional blood tests are preformed and vital sign information is collected for the patient. The caregiver 110 can log into the system 100 using the bedside monitor 108 and make a note that he has not observed anything abnormal, but that he has ordered a few tests for which he's waiting for results. The physician "invites" an ER nurse (electronically, through the system 100) to join a care group for the patient 104 and to coordinate the additional tests for the patient 104.

The ER nurse accesses the system 100 using her mobile device that is in wireless communication with the network 112 and sees the invitation from the physician and accepts. She accepts joining of this newly formed care group for the patient 104 and now has access to patient information for the patient 104. This can include access to a patient profile for the patient 104. Additionally, information for the patient 104 can be included in a patient news feed of information on multiple patients with which the ER nurse is associated. The ER nurse's personalized news feed can indicate that the tests requested by the physician for the patient 104. The ER nurse can confirm that she has ordered the tests.

The ER nurse can also contact the patient's family who indicate that they cannot be there for another 2 hours as they live far from the hospital, but would like to be kept updated on status. The nurse can use the system 100 to send an SMS invitation to one or more of the family members inviting the family members to subscribe to a care group for the patient 104, which the family members may accept via SMS.

The blood test data is pulled into the System 100 and automatically delivered to the ER nurse and the physician (who are identified as caregivers within the patient 104's care group), but not to the patient's family via the giver group—the system 100 identifies that this type of information is only intended for clinicians (first tier caregivers) within the care group, and not family members or other non-clinician members of the care group (second tier caregivers). The ER physician notices elevated troponin levels, and suspects that the patient had a heart attack. He then invites the on-call cardiologist to the patient-specific care group for the patient 104, after which the cardiologist accepts and immediately sees the history of the patient via a patient news feed that includes information for the patient 104, including historical information in the newsfeed. The patient news feed can be displayed, for example, as part of a visual representation of the patient 104's patient profile. This patient news feed allows the cardiologist to view real-time (or near real-time) vital sign data for the patient 104 even though the cardiologist is not physically located in the same location as the patient 104. The cardiologist notices an abnormality on the ECG reading for the patient 104 and orders an echocardiogram to confirm his suspicions of their being an acute cardiac event for the patient 104.

At this stage, the cardiologist makes a note to the patient's patient profile within the system 100 that the patient is to be admitted. The ER nurse receives this notification, at which point she invites a telemetry nurse to the patient 104's care group to let the telemetry nurse know to expect an incoming patient. The system 100 can track movements of the patient 104 and detect that the patient 104 has left the ER since the patient 104's chest sensor 102 has disassociated with the ER bedside monitor 108. Additionally or alternatively, movements of the patient 104 can be tracked using a GPS unit or other location determination unit included in the chest sensor 102. Information collected by a GPS unit included in the chest sensor 102 can be used to determine that the patient 104 has left the ER. In response to this determination that the patient 104 has left the ER, the system 100 can automatically disassociate the ER physician from the patient 104's care group so he no longer receives information or alerts associated with the patient 104. The ER nurse physically transports the patient to the telemetry ward, and at that time manually leaves the care group by accessing the system 100 from a system access station.

Alternatively, the system 100 can automatically remove the ER nurse from the care group based on identifying that the patient 104 is no longer located in the ER and is now located in the telemetry ward. As described above, the location of the patient 104 in the telemetry ward can be determined based on the chest sensor 102 associating with a bedside monitor located in the telemetry ward (thus indicating that the chest sensor 102 being worn by the patient 104 is within a close proximity of the bedside monitor in the telemetry ward. Additionally or alternatively, the patient 104's location within the telemetry ward can be identified using a GPS unit or other location determination unit included in the chest sensor 102. Additionally or alternatively, the patient 104's location within the telemetry ward can be identified based on information that is manually input by one or more caregivers. For example, the telemetry nurse can access a patient profile for the patient 104 and enter information indicating that the patient is currently located in a particular bed, in a particular room in the telemetry ward.

Once received by the telemetry nurse, the patient 104 is transitioned to inpatient status. The inpatient status of the patient 104 can be automatically pushed to electronic medical records for the patient stored at the central server 113. The telemetry nurse notices that a family member had joined the care group for the patient 104, and sends a text message to the family member indicating that the patient 104 has been admitted and is awaiting further testing. This notification can also be posted to the patient 104's patient profile as a text note.

The cardiologist receives the echocardiogram via a terminal in communication with the central server 113 through the network 112. The cardiologist is able to annotate directly on the echocardiogram image what his findings are and save this modified image to the patient 104's patient profile record. The cardiologist sees a blockage in the left circumflex artery, and is recommending the patient 104 be sent for immediate angioplasty and possible stenting. He then invites the Cath Lab to join the care group for the patient 104, at which time all Cath Lab staff are notified (by the system 100) that a procedure is imminent and to prepare the lab. Patient care records stored at the central server 113 are simultaneously updated with an indication of this decision and the telemetry nurse disassociates from the patient 104's care group.

During the procedure, the patient suffers from complications and the cardiologist recommends recovery in the cardiac telemetry unit. The cardiologist tries to locate or contact the patient 104's family but cannot, and then sends a message via patient group forum for the patient 104. Other family members had been invited to the care group for the patient 104, and now family members located in another state are receiving alerts for the patient 104 via email.

The same telemetry nurse is re-associated with the care group for the patient 104, and the on-call intensivist is also automatically added to the care group. He is able to scroll through the patient history for the patient 104 and immediately gets up to speed on what has happened over the past 4 hours.

During the 6th hour in the telemetry unit, the chest sensor battery for the chest sensor 102 (which has been re-adhered to the patient post-surgery) is running low—because the system 100 determines that this is a technical alarm, it only sends an alert to the telemetry nurse. The original telemetry nurse had actually ended her shift an hour ago, but she had left a video note on the patient's patient profile saying the battery was low—the incoming telemetry nurse reviews this video note at the start of her shift, and subsequently replaces the battery in the chest sensor 102. Later on in the night, an arrhythmia is diagnosed automatically by the central server 113 using vital sign information collected by the chest sensor 102. Both the intensivist and the nurse receive an alert that the patient 104 is experiencing arrhythmia. The managing cardiologist is also alerted and further receives a request from the intensivist to take a look at the abnormal rhythm. The managing cardiologist determines that variation in the heart rhythm is not a serious issue and everything is fine, and this finding is then noted in the patient 104's patient profile.

The patient 104 is then discharged home with one or more patient worn sensors such as the chest sensor 102 and wrist sensor 106, or other replacement sensors. The data recorded by the patient worn sensors is continuously supplied to the system 100 for recording into that patient 104's EMR stored at the central server. The status of the patient 104 can also be monitored from remote locations such as by the caregiver 116 at the central server station 114 (which can be located at a patient monitoring center outside of the hospital environment). Additionally, the telemetry nurse and intensivists can disassociate from the patient 104's care group. The cardiologist remains in the care group for further oversight in case caregivers monitoring the patient at the central server station 114 see anything for the patient 104 that raises suspicion. The members of the care group (including the patient 104's family members who joined the care group) are informed that the patient 104 went home and that he continues to be monitored at the central server station 114.

Figure 2:
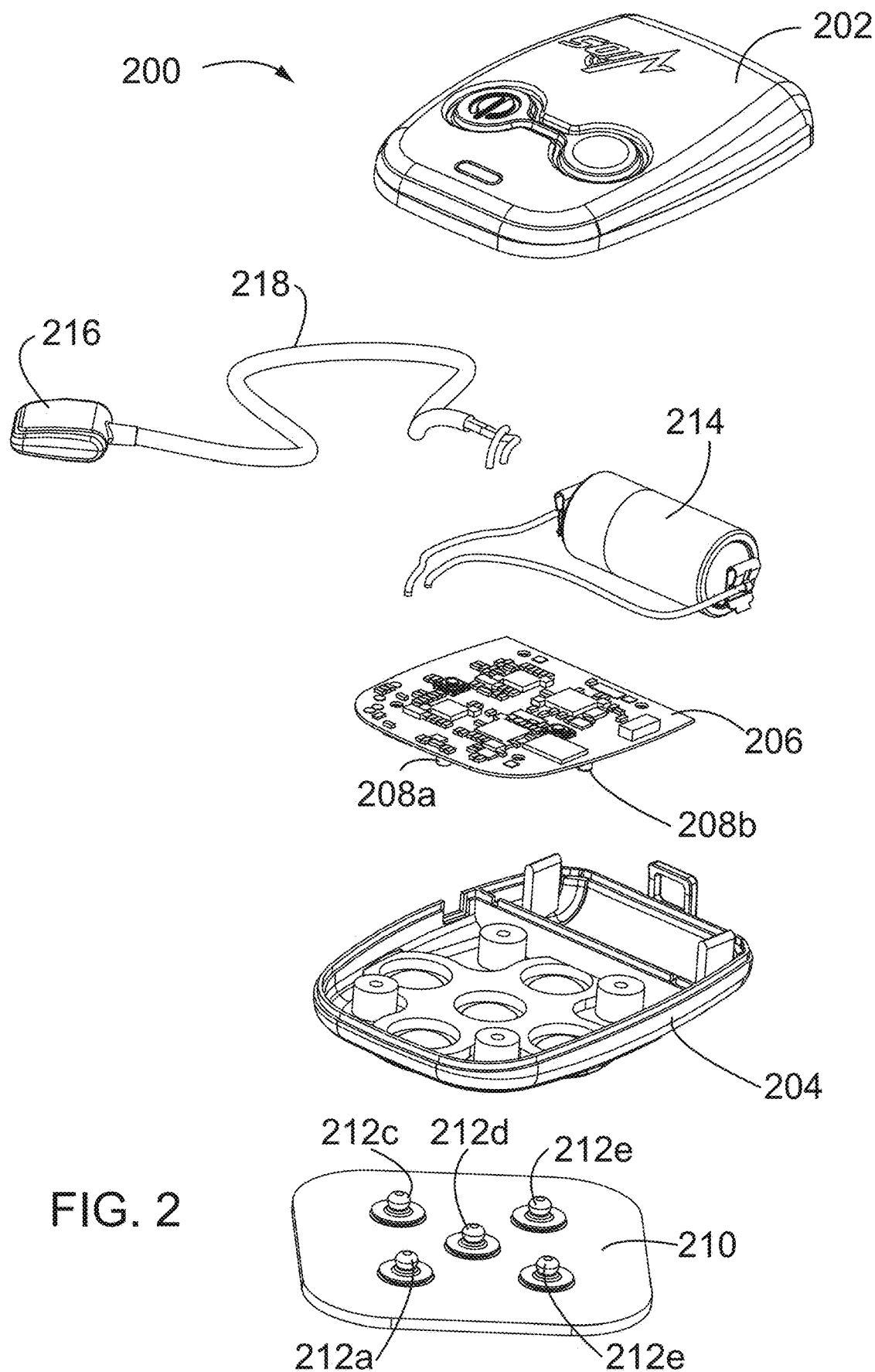
FIG. 2 is an exploded view of various components of a patient worn sensor.

FIG. 2 shows an exploded view of various components of a patient worn sensor 200. The patient worn sensor 200 can be a chest sensor. For example, patient worn sensor 200 can be used as the chest sensor 102 shown in FIG. 1. The patient worn sensor 200 includes a top outer case portion 202. The top outer case portion 202 can be configured to engage a bottom outer case portion 204 of the patient worn sensor 200 to encase and protect other components of the patient worn sensor 200. The top outer case portion 202 and bottom outer case portion 204 can be made from molded plastic or another material that is suitably light weight so as to facilitate easy attachment to a patient while also structurally strong enough to protect inner components of the patient worn sensor 200 from damage if the patient worn sensor 200 is dropped. The top outer case portion 202 and bottom outer case portion 204 can also be configured to engage each other in a water-tight or semi-water-tight seal to prevent moisture from reaching the inner components of the patient worn sensor 200. In some implementations, the top outer case portion 202 and/or bottom outer case portion 204 can include one or more buttons for controlling the patient worn sensor 200 (e.g., changing settings for the patient worn sensor 200). In some implementations, the top outer case portion 202 and/or bottom outer case portion 204 can include one or more lights (e.g., LEDs) for indicating an alarm state for a patient wearing the patient worn sensor 200, or a functional problem with the patient worn sensor 200 (such as loss of communication, or low battery).

The patient worn sensor 200 further includes a circuit board 206 containing circuitry for receiving various patient vital sign information for a patient wearing the patient worn sensor 200 and for transmitting the vital sign information to a computing device or computing system (such as the bedside monitor 108 of FIG. 1). In some implementations, the circuitry of the patient worn sensor 200 is configured to process received vital sign information to create human readable vital sign information, or to identify abnormal vital sign information (aka, vital sign information outside of pre-specified acceptable ranges) for the patient.

The circuit board 206 includes electrode contacts 208a and 208b as well as additional electrode contacts not shown in FIG. 2. The electrode contacts are configured to extend through apertures in the bottom outer case portion 204 to engage an electrode pad 210 having electrodes 212a-e. The electrode pad 210 can be a disposable pad that is configured to adhere to the skin of a patient wearing the patient worn sensor 200. The electrode pad 210 can be made from a foam material coated with an adhesive coating for contacting the skin of the patient. Each of the electrodes 212a-e includes a snap connector portion for engaging the electrode contacts 208a and 208b and the other electrode contacts not shown. For example, the electrode 212a is configured to releasably connect to the electrode contact 208a while the electrode 212b is configured to releasably connect to the electrode contact 208b. The electrodes 212a-e allow the patient worn sensor 200 to detect various vital sign signals and transmit these signals to the circuit board 206. Each of the electrodes 212a-e can include a hydrogel layer for contacting the skin of the patient and collecting vital sign information. In some implementations, the electrode pad 210 is removed from the patient worn sensor 200 and replaced on a regular basis (e.g., every three days) to ensure that sufficient contact with the patient's skin is maintained while keeping the contact site clean. The other components of the patient worn sensor 200 can be continually reused with the electrode pad 210 being replaced. The permanent components of the patient worn sensor 200 can additionally be reused for different patients, while the electrode pad 210 is replaced when the patient worn sensor 200 is transferred from one patient to another.

The electrodes 212a-e can extend through the electrode pad 210 and be configured to contact and releasably adhere to the skin of a patient wearing the patient worn sensor 200. The electrodes 212a-e can collect various bio signals from the patient and transfer these signals to the circuit board 206. The circuit board 206 can be configured to attach to the skin of the patient near the patient's heart and record vital sign information for the patient, including heart rhythm (via ECG) and heart rate. The patient worn sensor 200 can be, for example, a 6-lead ECG sensor having I, II, III, aVL, aVR, and aVF leads. Other vital signs that can be monitored by the patient worn sensor 200 or a combination of the patient worn sensor 200 and one or more additional sensors can include blood pressure, body temperature, respiratory rate, blood oxygenation, blood glucose level, hydration levels and perspiration. The circuit board 206 additionally includes circuitry for transmitting information to one or more computing devices or computing systems. For example, the circuit board 206 can include a Bluetooth transmitter for transmitting information to a bedside monitor or other computing device using a Bluetooth protocol. The circuit board 206 can also include one or more communications modules for connecting to a wireless network such as a WiFi network or a cellular network.

Additional components that can be included as part of the circuit board 206 include location identification circuitry such as a GPS unit or a radio signal triangulation based location determination device. A GPS unit or other location determination circuitry included as part of the circuit board 206 can be used, for example, to identify a location of a patient when the patient is not located where the patient should be at a specified time. The GPS unit can be used to locate patients suffering from dementia or other mental illnesses who are prone to wandering and becoming lost. In some implementations, the circuit board 206 includes one or more accelerometers for detecting and recording patient motion, activity, position, and posture. For example, an accelerometer included as part of the circuit board 206 can track patient activity to allow a caregiver to determine if the patient is receiving a sufficient level of daily exercise, or if the patient is engaging in too much activity for the current physical condition of the patient. The accelerometer can also be used to determine if the patient has fallen, or if the patient has been motionless for a period of time greater than a pre-determined threshold. The accelerometer can also be used to track patient sleep patterns, or to track the posture of the patient to allow caregivers to provide recommendations for how the patient can better position himself when seated, lying, standing, etc. The accelerometer could additionally provide information to caregivers that can be used to determine if the patient is engaging in activities or habits that can increase the risk of re-injury or of developing complications.

The patient worn sensor 200 includes a power supply 214. The power supply 214 can be a rechargeable battery, a battery pack for receiving a disposable battery, or the like. The power supply 214 is contained within the housing (top outer case portion 202 and bottom outer case portion 204) of the patient worn sensor 200 and provides power for the circuit board 206 and other components of the patient worn sensor 200.

The patient worn sensor 200 further includes a temperature sensor 216 for monitoring body temperature of the patient. The temperature sensor 216 is configured to attach to the skin of the patient underneath the patient's arm to best monitor the patient's temperature. A cord 218 extends from the temperature sensor 216 through an opening formed when the top outer case portion 202 engages the bottom outer case portion 204 and connects to the circuit board 206 to convey the signals detected by the temperature sensor 216 to the circuit board 206. In some implementations, the temperature sensor 216 includes one or more disposable temperature electrodes that can be removed from the temperature sensor 216 and replaced periodically.

Figure 3A:
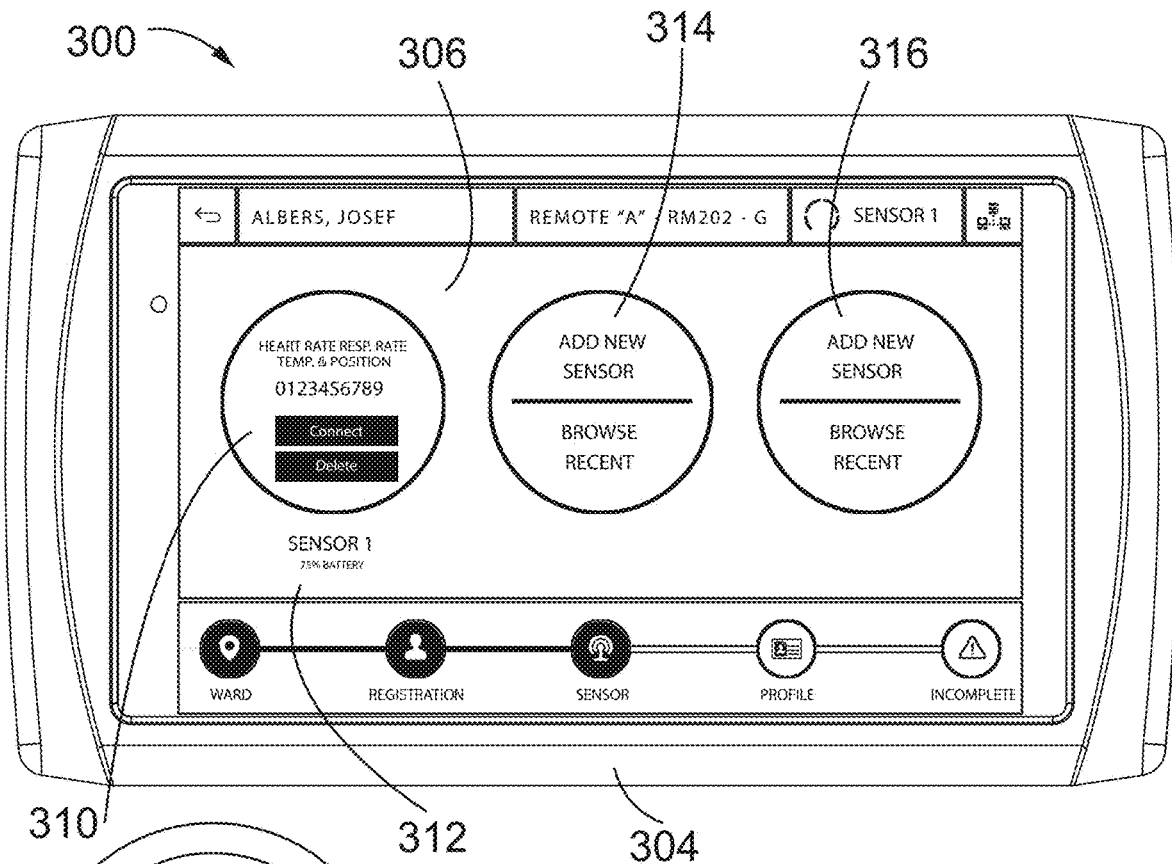
FIGS. 3A-3E show a patient worn sensor in wireless communication with a bedside monitor having several example display screens for conveying patient information.
Figure 3A:
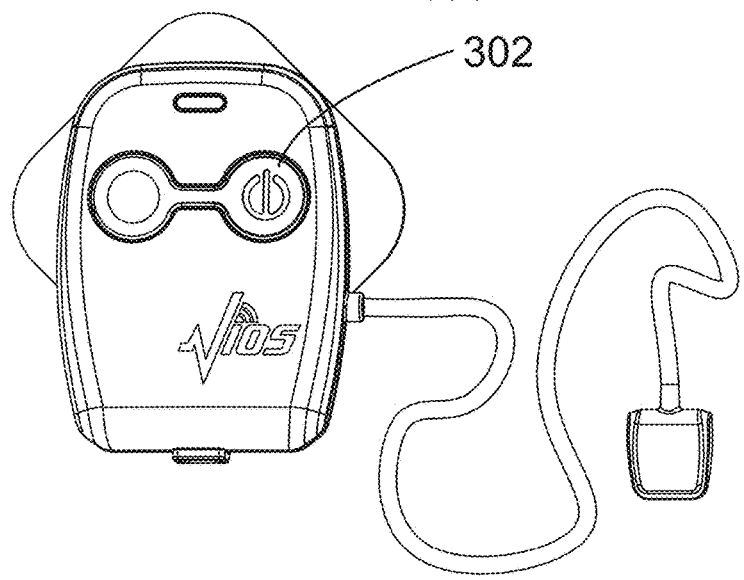

FIG. 3A shows a system 300 that includes a patient worn sensor 302 in wireless communication with a bedside monitor 304 having a bedside monitor 304 displaying information for a patient care system, such as, for example, the system 100 of FIG. 1. The bedside monitor 304 can include a user interface 306 that includes information received from the patient worn sensor 302 and/or information associated with a patient associated with the patient worn sensor 302. The patient worn sensor 302 can be, for example, a chest sensor such as the chest sensor 102 of FIG. 1. The patient worn sensor 302 can include contacts for attaching to the skin of a patient and recording various patient vital signs such as blood pressure, body temperature, respiratory rate, body impedance, blood oxygenation, heart rhythm (via ECG), and heart rate.

The patient worn sensor 302 can wirelessly communicate with the bedside monitor 304 through a wireless connection 308 using a wireless communication protocol such as, for example, Bluetooth, WiFi, or a cellular protocol. The patient worn sensor 302 can transmit vital sign information for the patient to the bedside monitor 304 through the wireless connection 308. In some implementations the patient worn sensor 302 can perform processing on the collected vital sign information prior to transmission of the information to the bedside monitor 304, while in some implementations, the patient worn sensor 302 can transmit raw vital sign information to the bedside monitor 304 instead of or in addition to processed information. The bedside monitor 304 can be a touch screen device, such as a tablet, that is capable of receiving touch screen inputs. In some implementations, the bedside monitor 304 can receiving input from a keyboard, mouse, input buttons, or one or more devices capable of recognizing voice commands. In some implementations, the bedside monitor 304 can be controlled using a device in wireless communication with the bedside monitor 304, such as a mobile phone. In some implementations, the bedside monitor 304 is a "headless" device that does not include direct user input and/or output functionality, but rather merely serves as a processing device for processing raw vital sign information received from the patient worn sensor 302, detecting alarm states, transmitting alerts to other devices in communication with the bedside monitor 304, and transmitting patient information to one or more central servers (e.g., the central server 113 of FIG. 1). In such cases, the bedside monitor 304 would not include a display.

The user interface 306 displays information for a patient "Josef Albers" associated with the patient worn sensor 302. At 310, the user interface 306 indicates that the patient worn sensor 302, having a sensor ID of 012346789 is synced with the bedside monitor 304 and is currently collecting information for the patient including heart rate, respiration rate, temperature, and patient position/location. The user interface 306 further indicates at 312 that the battery level for the patient worn sensor 302 (identified as "sensor 1" by the user interface 306) is 75%. The user interface 306 further includes selectable areas 314 and 316 that can be used to sync additional sensors with the bedside monitor 304. For example, a user can select the selectable area 314 to sync a patient worn sensor associated with a different patient with the bedside monitor 304. As another example, a user can select the selectable area 316 to sync a wrist worn sensor worn by the same patient associated with the patient worn sensor 302 with the bedside monitor 304. In some implementations, the selectable area 316 is only selectable if the "sensor 2" slot indicated by the selectable area 314 is already associated with a sensor that is synced with the bedside monitor 304.

A user of the bedside monitor 304 can use touchscreen functionality of the bedside monitor 304, a mouse, or another input device to select an area of the user interface 306 at 310 to cause additional display screens associated with the patient associated with the patient worn sensor 302 (displayed as "sensor 1") on the bedside monitor 304. In the example shown, selecting the user interface 306 at 310 can cause one or more additional display screens having information associated with the patient "Josef Albers" to be displayed.

Figure 3B:
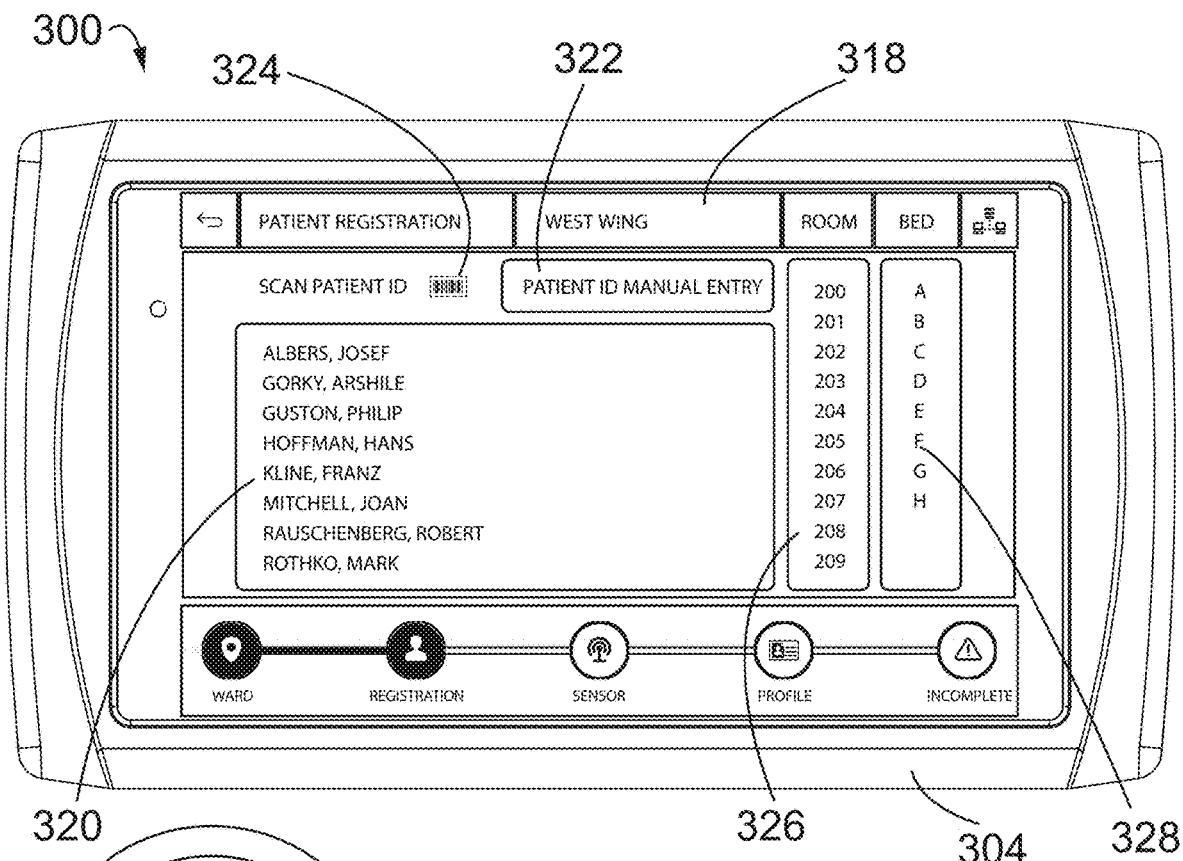
Figure 3B:
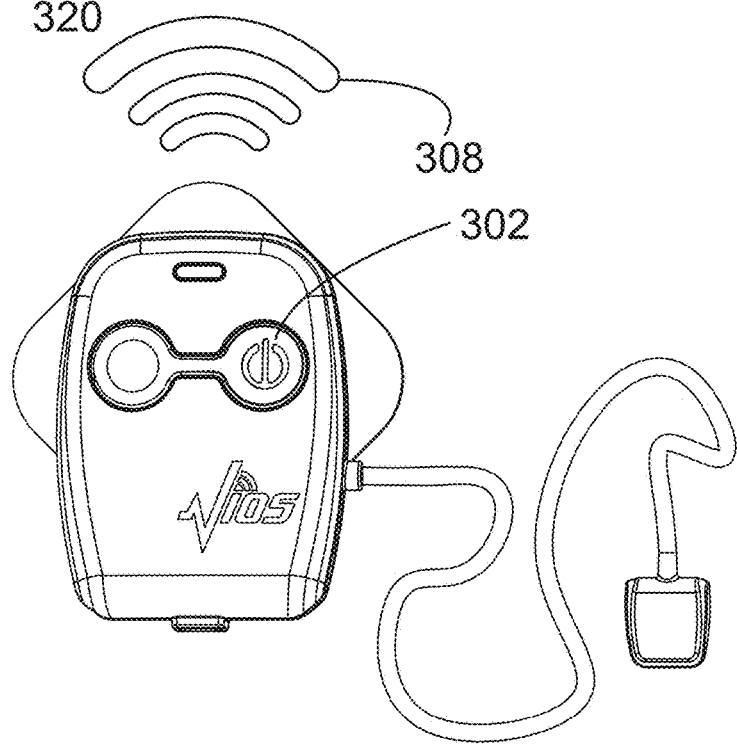

Turning to FIG. 3B, the bedside monitor 304 is in wireless communication with the patient worn sensor 302 through the wireless connection 308. The bedside monitor 304 includes a user interface 318. The user interface 318 can be accessed by selecting, for example, one or more portions of the user interface 306 shown in FIG. 3A. For example, referring to FIG. 3A, a caregiver can select the selectable area 314 to cause the user interface 318 to be displayed.

Returning to FIG. 3B, the user interface 318 is a patient registration screen that can be used to associate the patient worn sensor 302 with a particular patient as well as enter additional information associated with the patient. The user interface 318 includes an alphabetical list of patients 320 that can be associated with the patient worn sensor 302. For example, the list of patients 320 can include patients who are identified by a central sever as being current patients of a particular healthcare facility where the bedside monitor 304 is located. A user of the bedside monitor 304 can select a name from the list of patients 320 to cause the selected patient to be associated with the patient worn sensor 302. Associating a particular patient with the patient worn sensor 302 can cause information collected by the patient worn sensor 302 to be included in a patient profile for the particular patient. Additionally, vital sign threshold information (aka, acceptable ranges for various vital signs) associated with the particular patient can be transferred to the patient worn sensor 302 to allow the patient worn sensor 302 to identify if vital signs for the particular patient are within acceptable levels. In some implementations, rather than transferring vital sign threshold information for the patient to the patient worn sensor 302, the bedside monitor 304 performs functionality of comparing vital sign information collected by the patient worn sensor 302 to the threshold information for the patient (e.g., to determine if an alarm state exists for the patient). In some implementations, the functionality of comparing vital sign information collected by the patient worn sensor 302 to the threshold information for the patient is performed by a different computing device, such as, for example, the central server 113 or the central server station 114 of FIG. 1.

The user interface 318 additionally includes a text field 322 to allow a user of the bedside monitor 304 to manually input a patient ID for a patient to associate with the patient worn sensor 302. As described above, a unique patient ID can be a name of the patient, a unique number, or a unique combination of numbers, letters, and other characters. In some implementations, as indicated at 324, a patient ID for a patient can be scanned to be input into the bedside monitor 304. For example, the patient can be wearing a wrist band having a barcode that encodes an identifier for the patient. A scanner connected to the bedside monitor 304 can be used to scan the barcode on the patient's wrist band to identify the patient and associate the patient with the bedside monitor 304 and the patient worn sensor 302. As another example, the patient worn sensor 302 can be associated with a patient prior to the patient worn sensor 302 syncing with the bedside monitor 304. A scanner connected to the bedside monitor 304 can be used to scan a barcode imprinted on the patient worn sensor 302 to identify the patient worn sensor 302 (and subsequently identify the patient) or a scanner connected to the bedside monitor 304 can be used to scan an electrical signal being emitted by the patient worn sensor 302 to identify the patient worn sensor 302 (and subsequently identify the patient associated with the patient worn sensor 302). In some implementations, a user of the bedside monitor 304 can select the user interface 318 at 324 to cause the bedside monitor 304 to enter a scanning mode in which the bedside monitor 304 (e.g. via a built in camera), or an input peripheral (e.g., an RFID scanner or barcode scanner) in communication with the bedside monitor 304, can receive a scanned patient ID.

The user interface 318 further includes a field 326 that allows a user of the bedside monitor 304 to indicate a room to associate with a selected or indicated patient. The user interface 318 also includes a field 328 that allows the user to indicate a bed within the selected room that is associated with the selected or indicated patient.

Figure 3C:
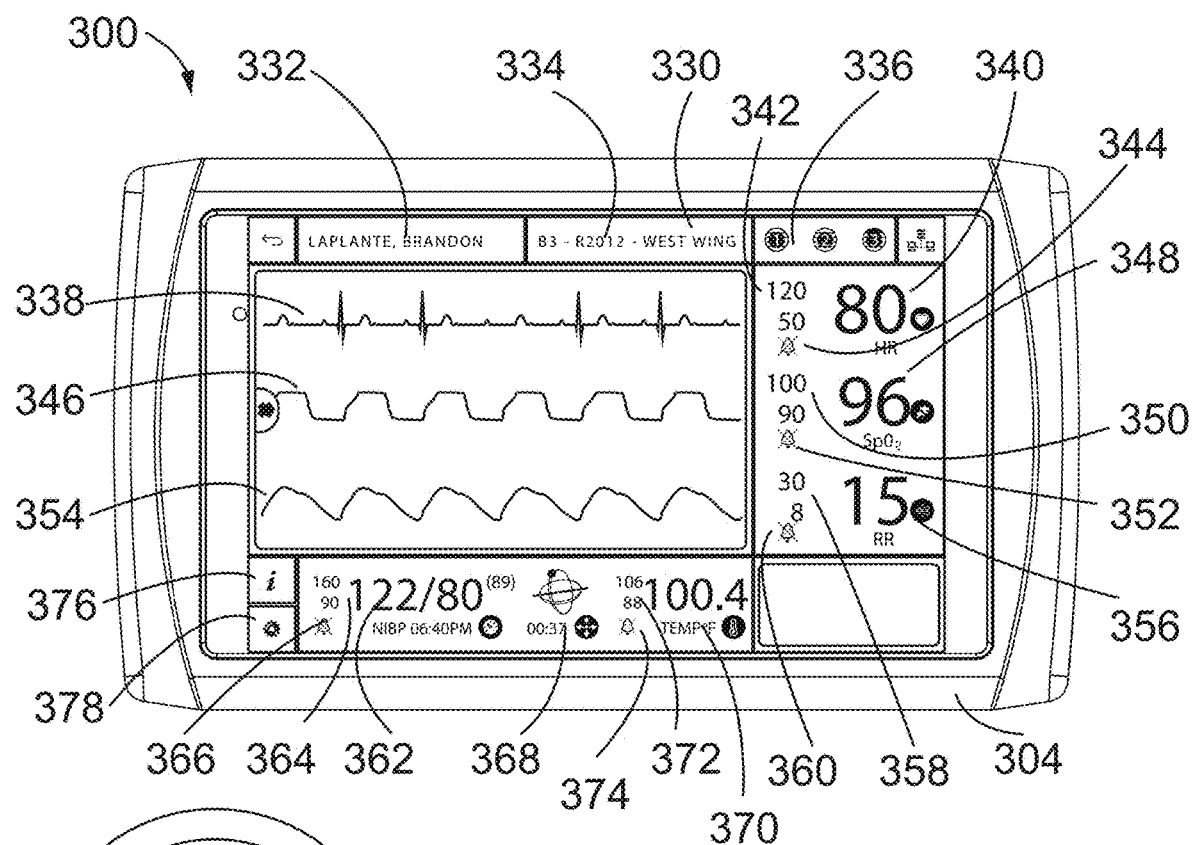
Figure 3C:
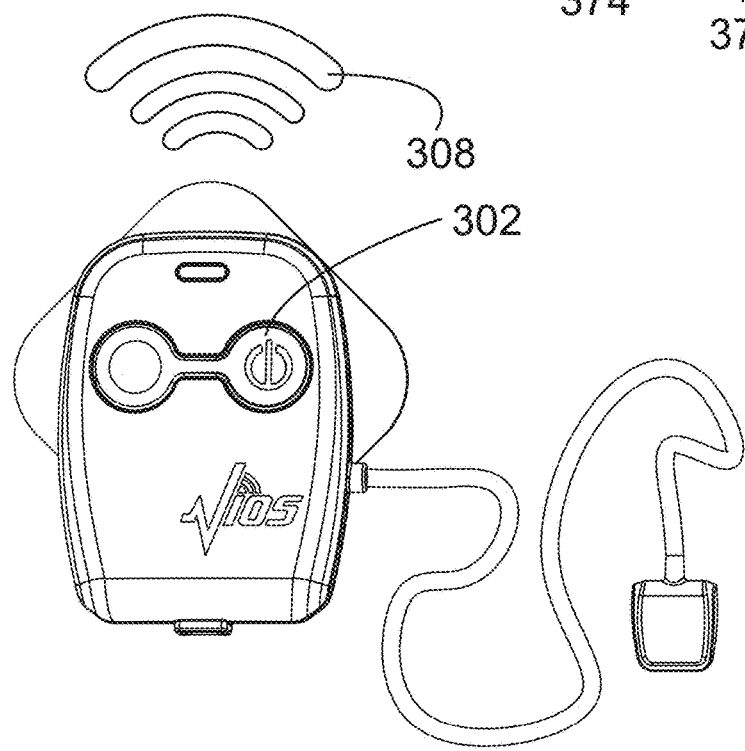

Turning to FIG. 3C, the bedside monitor 304 is in wireless communication with the patient worn sensor 302 through the wireless connection 308. The bedside monitor 304 includes a user interface 330 displaying vital sign information for a patient associated with the patient worn sensor 302. For example, electrodes of the patient worn sensor 302 can be in contact with the patient's skin and collect vital sign information which is transferred to the bedside monitor 304 through the wireless connection 308, processed by the bedside monitor 304, and displayed as part of the user interface 330. In some implementations, a user of the bedside monitor 304 can reach the user interface 330 by making a selection on another display screen. For example, making a selection on the user interface 306 of FIG. 3A at location 310 can cause the user interface 330, including information for the patient associated with "sensor 1" to be displayed on the bedside monitor 304.

Returning to FIG. 3C, the user interface 330 further includes an indication of a name for a patient at 332 that is associated with the patient worn sensor 302. At 334, the user interface 330 indicates that the patient is located in bed 3 of room 2012 in the west wing of a healthcare facility where the bedside monitor 304. This can also indicate that the bedside monitor 304 is associated with this particular bed. At 336, the user interface 330 indicates that three sensors, including the patient worn sensor 302 and two additional sensors, are currently synced with the bedside monitor 304. The user interface 330 at 336 additionally indicates a battery charge level for each of the three sensors. The example depicted in FIG. 3C shows that the charge level of sensors 1 and 2 are full, while the charge level of sensor 3 is less than full.

The user interface 330 additionally shows various vital sign waves and numeric levels. For example, the user interface 330 shows a heart rate waveform 338 for the patient as well as a numeric heart rate value 340 for the patient. In the example shown, the heart rate value 340 for the patient is 80 beats per minute. The user interface 330 indicates at 342 an acceptable heart rate level for the patient as falling between 50 and 120 beats per minute. Being as the current heart rate for the patient of 80 beats per minute falls within the indicated acceptable range, there is not currently an alarm state for heart rate for the patient. This is indicated by an icon 344 of a bell superimposed with an "X" symbol. The icon 344 indicates that the current heart rate of the patient is within the acceptable range. In a situation in which the heart rate for the patient is not within the acceptable level, the icon 344 can change to indicate an alarm state. For example, the "X" can disappear from the icon 344 and the icon 344 can light up or flash to indicate an alarm state. Additionally, the bedside monitor 304 can emit an audible alarm to alert nearby caregivers to an alarm state for the patient. In some implementations, other portions of the user interface 330 can flash or otherwise indicate an alarm state. For example, the displayed heart rate value 340 can flash when the patient's heart rate is outside of an acceptable level. In some implementations, the icon 344 (or other portions of the user interface 330) can flash at varying rates to indicate the severity of a particular alarm state. For example, the icon 344 can flash faster the further the patient's heart rate is from the acceptable range.

The user interface 330 also shows a blood oxygenation waveform 346 and a numeric blood oxygenation value 348 for the patient. The user interface 330 also shows, at 350, an acceptable blood oxygenation range for the patient. The user interface 330 further includes an icon 352 indicating that the blood oxygenation level for the patient is within the acceptable range (indicated by an "X" symbol superimposed over a bell, indicating that the alarm is "off").

The user interface 330 additionally includes a respiratory rate waveform 354 and a numeric respiratory rate value 356 which shows a numeric value indicating the number of breaths per minute taken by the patient. In the example shown, the patient has a respiration rate of 15 breaths per minute, as indicated by the respiratory rate value 356. The user interface 330 also shows, at 358, an acceptable respiration rate range for the patient. In the example shown, the acceptable respiration rate range is 8 breaths per minute to 30 breaths per minute. The user interface 330 further includes an icon 360 indicating that the respiration rate for the patent is within the acceptable range (indicated by an "X" symbol superimposed over a bell, indicating that the alarm is "off").

The user interface 330 further includes a blood pressure value 362 for the patient. In the example shown, the blood pressure value 362 indicates that the patient's current blood pressure is 122/80. The user interface 330 additionally includes, at 364, an acceptable blood pressure range for the patient. The user interface 330 further includes an icon 366 indicating that the blood pressure for the patent is within the acceptable range (indicated by an "X" symbol superimposed over a bell, indicating that the alarm is "off").

The user interface 330 further includes an orientation indicator 368 indicating a current orientation for the patient as well as an indication of how long the patient has been in the current orientation. The orientation indicator 368 can help a caregiver to identify if the patient has been in a current orientation for longer than a preferred length of time. The orientation indicator 368 can also be used to indicate that the patient has fallen and is in need of assistance (e.g., through use of an audible or visual alarm, indicating that the alarm is "off").

The user interface 330 further includes a numeric body temperature value 370 for the patient. In the example shown, the body temperature value 370 indicates that the patient's temperature is currently 100.4 degrees Fahrenheit. The user interface 330 also includes, at 372, an acceptable temperature range for the patient, and an icon 374 indicating that the body temperature for the patent is within the acceptable range (indicated by an "X" symbol superimposed over a bell).

The bedside monitor 304 can allow a caregiver to access additional information for the patient other than the information displayed by the user interface 330. For example, a caregiver can select a portion of the user interface 330 at the displayed heart rate value 340 to cause recorded heart rate information for the patient to be displayed. In this example, the bedside monitor 304 can display heart rate measurements for the patient taken at regular 15 minute intervals for the past several hours. As another example, the caregiver can select the user interface 330 at the orientation indicator 368 to access recorded orientation information for the patient.

The bedside monitor 304 can also be used to manually add information associated with the patient or to change one or more settings for the patient. For example, a caregiver can use the bedside monitor 304 to enter notes on what the patient ate that day, the patient's physical activity for the day, or any changes to the patient's status that is not indicated by the automatically tracked vital signs (such as the patient experiencing head-aches, or increased pain/swelling at a surgical incision). The caregiver can also use the bedside monitor 304 to change one or more of the acceptable vital sign ranges. For example, the caregiver can select the user interface 330 at 342 to change the acceptable heart rate range for the patient from 50-120 BPM to 70-125 BPM. As another example, the caregiver can select the user interface 330 at 372 to change the acceptable temperature range for the patient from 88 to 106 degrees to 93 to 101 degrees.

The user interface 330 further includes control buttons 376 and 378 for accessing various controls or other display screens for the bedside monitor 304. For example, the control button 376 can be used to access additional information about the system 300, the patient worn sensor 302, the bedside monitor 304, or the patient. As another example, the control button 378 can be used to access a settings menu. The settings menu can be used to, for example, change the brightness of the display of the bedside monitor 304, change the volume of audible alarms, change syncing configurations for the bedside monitor 304 with respect to one or more sensors, or change the configuration of information displayed on the user interface 330.

Figure 3D:
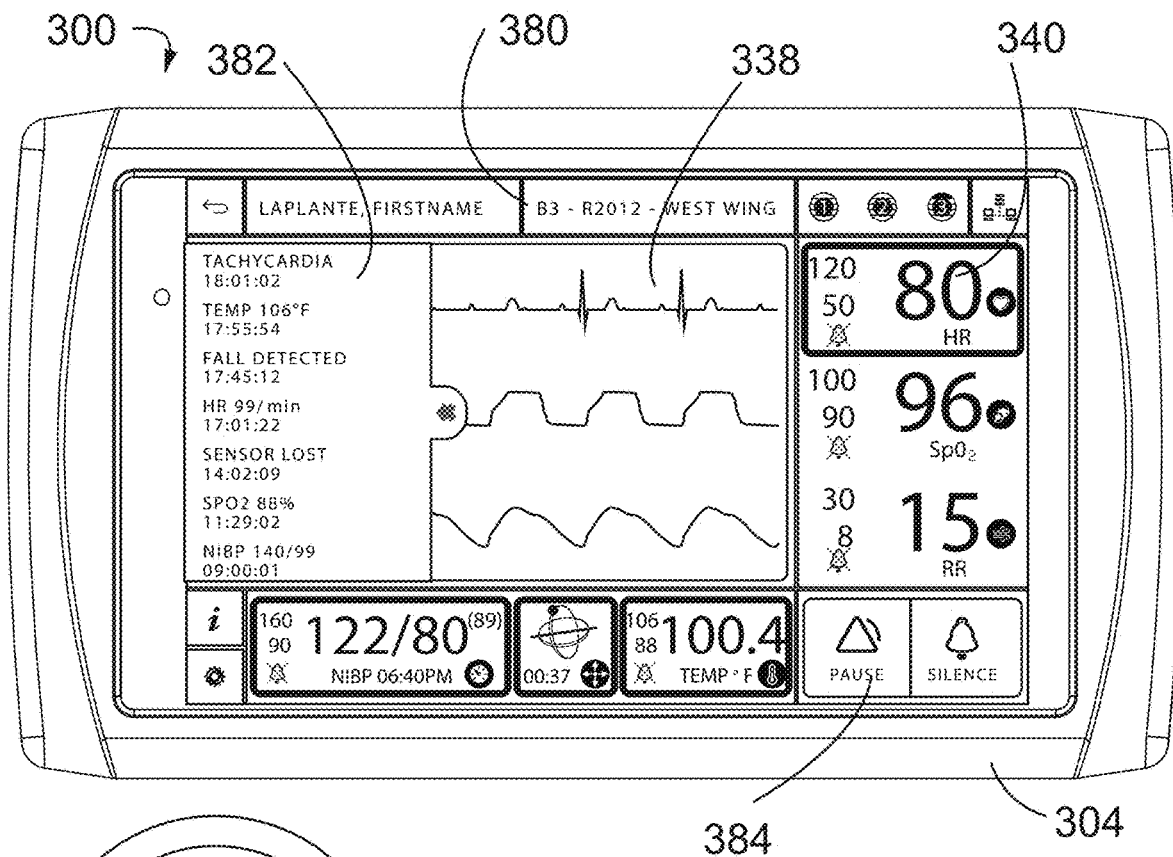
Figure 3D:
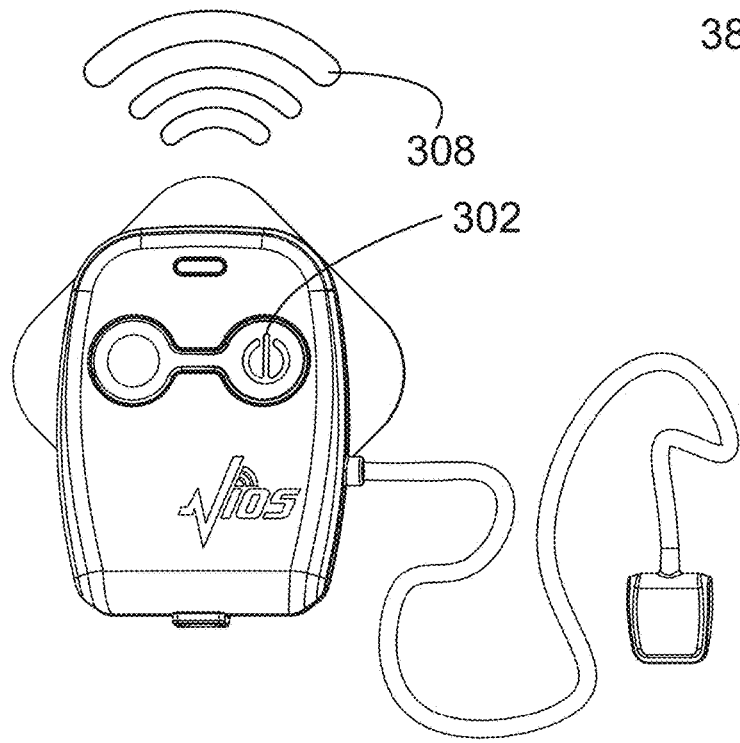

Turning to FIG. 3D, the bedside monitor 304 is in wireless communication with the patient worn sensor 302 through the wireless connection 308. The bedside monitor 304 includes a user interface 380 displaying vital sign information for a patient associated with the patient worn sensor 302. The display screen 376 includes much of the same information included in the user interface 330 discussed with respect to FIG. 3C above. For example, the user interface 380 includes the heart rate waveform 338 for the patient as well as the numeric heart rate value 340 for the patient.

In addition to the information displayed by the user interface 330, the user interface 380 includes an alert panel 382 showing alerts for various alarm states associated with the patient, as well as time stamps indicating when each of the alarm states was first detected. For example, the alert panel 382 indicates that tachycardia (increased heart rate outside of acceptable levels) occurred at 18:01:02. Additionally, the alert panel 382 indicates that a temperature of 106 degrees (which is outside of the acceptable temperature range for the patient) was detected at 17:55:54. As yet another example, the alert panel 382 indicates that a fall was detected by the patient worn sensor 302 at 17:45:12. In addition to displaying alarm states in the alert panel 382, the bedside monitor 304 can also alert caregivers to an alarm state by causing one or more portions of the display to flash, issuing an audible alarm, or transmitting alerts to other devices. For example, as described above with reference to FIG. 1, the bedside monitor 304 can transmit an alert to a central server which can then identify one or more caregivers to whom to direct the alert associated with the patient. The central server can then transmit alerts to devices associated with the identified caregivers.

The user interface 380 further includes an alert control 384 that allows a user of the bedside monitor 304 to pause or silence an alert. For example, a caregiver can be alerted to an alarm situation (e.g., by an alert received at a station where the caregiver is located). The caregiver can go to the patient's location to address the alert. The caregiver can pause the alert using the alert control 384 while the caregiver addresses an alarm state that initiated the alert. If the caregiver is unable to properly address the alarm state, the caregiver can use the alert control 384 to un-pause the alert, which can lead the system 300 to escalate alerts for the alarm state and notify one or more additional caregivers of the alarm state. In another example, the caregiver can use the alert control 384 to silence an audible alarm (to reduce distractions while dealing with the alarm state) without pausing the alert. This can allow the system 300 to escalate the alerts if the alarm state is not remedied within a threshold period of time.

Figure 3E:
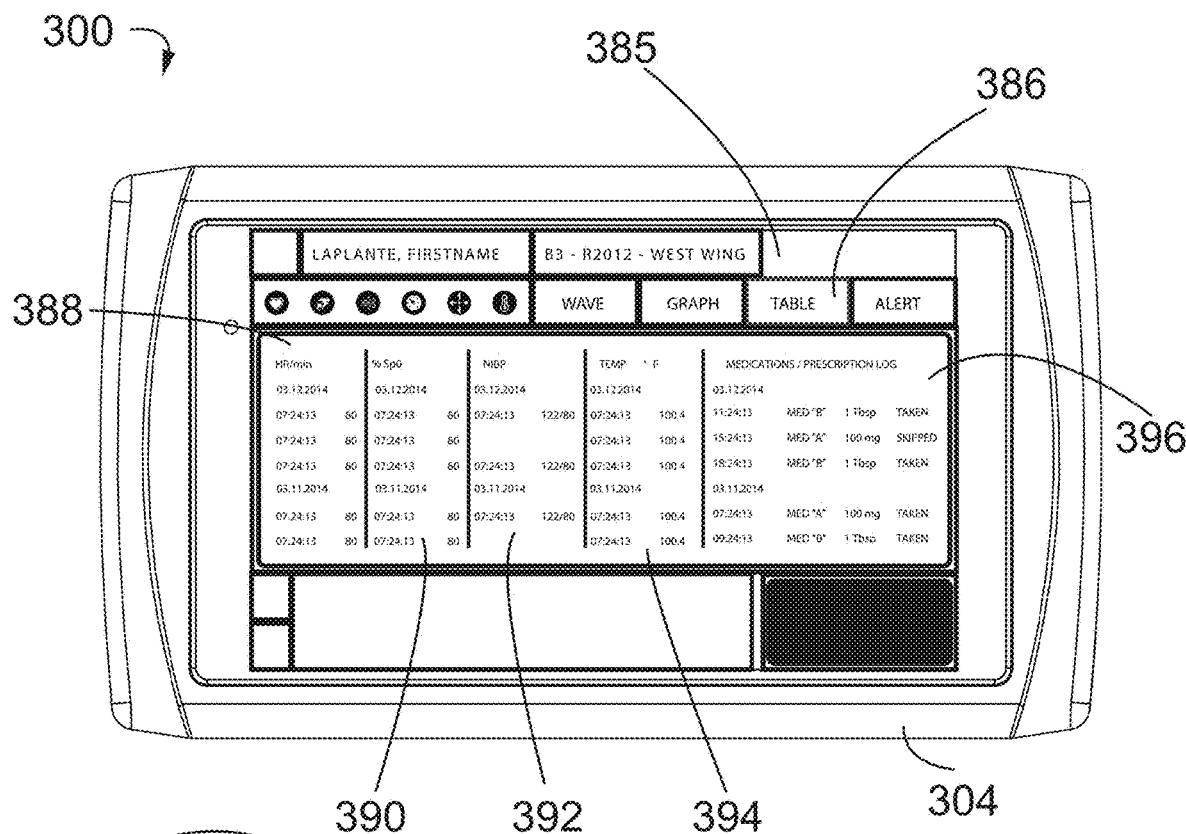
Figure 3E:
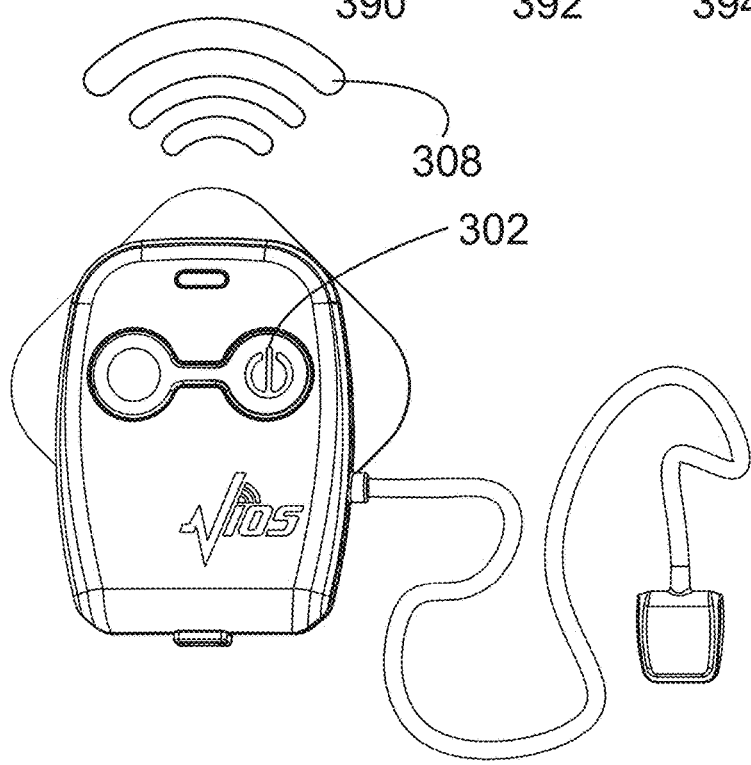

Turning to FIG. 3E, the bedside monitor 304 is in wireless communication with the patient worn sensor 302 through the wireless connection 308. The bedside monitor 304 includes a user interface 385 displaying historical vital sign information and other information for the patient. The user interface 385 includes a control 386 that is user selectable to allow a user of the bedside monitor 304 to view historical information associated with the patient in a table format. The user interface 385 includes a panel 388 that displays historic heart rate information for the patient. The panel 388 displays a date at which the heart rate readings were measured, and a list of time stamps indicating times at which the heart rate readings were measured, and heart rate values that were measured at the indicated times.

The user interface 385 further includes a panel 390 indicating historic blood oxygenation level information for the patient. The panel 390 displays a list of blood oxygenation level values recorded for the patient, the date on which the blood oxygenation level values were recorded, and times at which the blood oxygenation level values were recorded. The user interface 385 similarly includes a panel 392 displaying historic heart rate information for the patient including recorded heart rates and the dates and times at which the heart rate readings were recorded. Additionally, the user interface 385 includes a panel 394 that displays historic body temperature information for the patient including temperature readings and the dates and times at which the temperature readings were recorded. The information displayed in one or more of the panels 388, 390, 392, and 394 can be vital sign information that is automatically recorded by one or more patient worn sensors, such as the patient worn sensor 302, or the chest 102 and the wrist sensor 106 of FIG. 1. In some implementations, the bedside monitor 304 can receive the displayed information directly from one or more patient worn sensors, store the information in a local memory of the bedside monitor, and display the information as part of the user interface 385. In some implementations, the bedside monitor 304 retrieves some or all of the information displayed as part of the user interface 385 from a remote server, such as the central server 113 of FIG. 1. The bedside monitor 304 can, for example, transmit a patient ID for the patient to the remote server as long as a request for specified information related to the patient and a time frame for the specified information. The remote server can then provide the requested information for the identified patient to the bedside monitor 304 for inclusion in the user interface 385.

In some implementations, the vital sign information displayed as part of the user interface 385 is recorded by more than one patient worn sensor. For example, some of the information can be recorded by a first patient worn sensor. The first patient worn sensor can then be removed from the patient and replaced by a second patient worn sensor which can record additional vital sign information for the patient. Vital sign information recorded by both the first and second patient worn sensors can be included in the panels 388, 390, 392, and 394. In some implementations, information displayed as part of the user interface 385 includes information that is automatically recorded by one or more patient worn sensors as well as information that is manually entered by one or more caregivers. For example, a caregiver can measure a height and weight for the patient and manually enter the information into the bedside monitor 304. This height and weight information can be displayed as part of the user interface 384 along with the automatically recorded vital sign information.

The user interface 385 additionally includes a panel 396 that displays medication administration information for the patient. The panel 396 indicates dates and times at which various medications were administered to the patient, what the medications are (in this example, "MED 'B'" and "MED 'A'") and the dosage level of each medication. The panel 396 further includes an indication of whether or not the patient actually took the medication at the indicated time. If a patient took (e.g. successfully ingested) the medication at the indicated time, the panel 396 displays "taken" for that time stamp. If the patient did not take the medication, the panel 396 indicates "skipped" for that medication at the particular time stamp.

The medication administration information displayed by panel 396 can be manually entered by a caregiver. For example, a nurse can administer medication to the patient and then input information for the medication administration into the bedside monitor 304. In some cases, the information displayed in the panel 396 is manually entered at a terminal or device other than the bedside monitor 304. For example, the displayed information can be entered by a caregiver using a mobile device. The information is then stored at a remote server and accessed by the bedside monitor for display in the panel 396. In some implementations, the user interface 385 (or another user interface on the bedside monitor 304 or another device) can prompt a user to enter information regarding a medication administration. For example, the bedside monitor 304 can determine that the patient is scheduled to receive medication at a specified dosage at 5:00 pm. The bedside monitor 304 can determine that the current time is 5:05 pm and display a prompt inquiring "Was 100 mg of medication A administered to patient at 5:00 pm?" The user can then respond to the prompt by indicating whether or not the medication was administered and successfully taken by the patient, as well as if the administration occurred at the scheduled time (e.g. 5:00 pm) or at a different time.

In some implementations, the panel 396 can also display future scheduled medication administration times for the patient. For example, the panel 396 can include a time and date indication for a time in the future along with a list of one or medications to be administered to the patient at the indicated time and the dosage for each medication to be administered. This can allow a user of the bedside monitor 304 to quickly identify when the patient is scheduled to receive future dosages of medication.

The user interface 385 can include additional information for the patient, such as for example, historic respiratory rate readings, historic location information, historic motion information or other patient related information along with time stamps indicating dates and times at which the information was recorded. The user interface can also include a listing of past alarm states for the patient and information related to each alarm state. Another example of historic patient information that can be included in the user interface 385 is past therapy treatment for the patient, including time stamps for the therapy treatments and any progress or status changes for the patient related to the therapy treatment. The historic patient information displayed as part of the user interface 385 can assist caregivers in identifying or diagnosing problems for the patient. Caregivers can review the historic information to identify trends or patterns that can be indicative of issues related to the patient's health. In some implementations, the user interface 385 allows the user to scroll through one or more of the display panels 388, 390, 392, 394, and 396 to view additional historic information for the patient.

The user interface 385 can also include indications of recorded vital sign information or other information that is outside of a specified normal range for the patient. This can include vital signs that deviate enough from indicate normal ranges to rise to the level of an alarm state as well as slight deviations from a normal level. For example, one or more vital sign listings of the user interface 385 can be color coded to draw attention to the particular listings to indicate that the vital signs are out of a specified normal range. For example a first heart rate listing can be color coded yellow to indicate a slight deviation from a normal range, while a second temperature listing can be coded red to indicate a significant deviation from a normal range, or a deviation from a normal range lasting longer than a specified period of time. Visually distinguishing historic information for the patient that deviates from normal or expected ranges can help a caregiver to quickly identify problems for the patient to better determine a course of care for the patient.

In some implementations, the user interface 385 can include reminders related to care for the patient. For example, as mentioned above, future scheduled mediation administration can be listed by the user interface 385. As another example, the user interface 385 can include a listing of future scheduled therapy appointments for the patient.

Figure 4A:
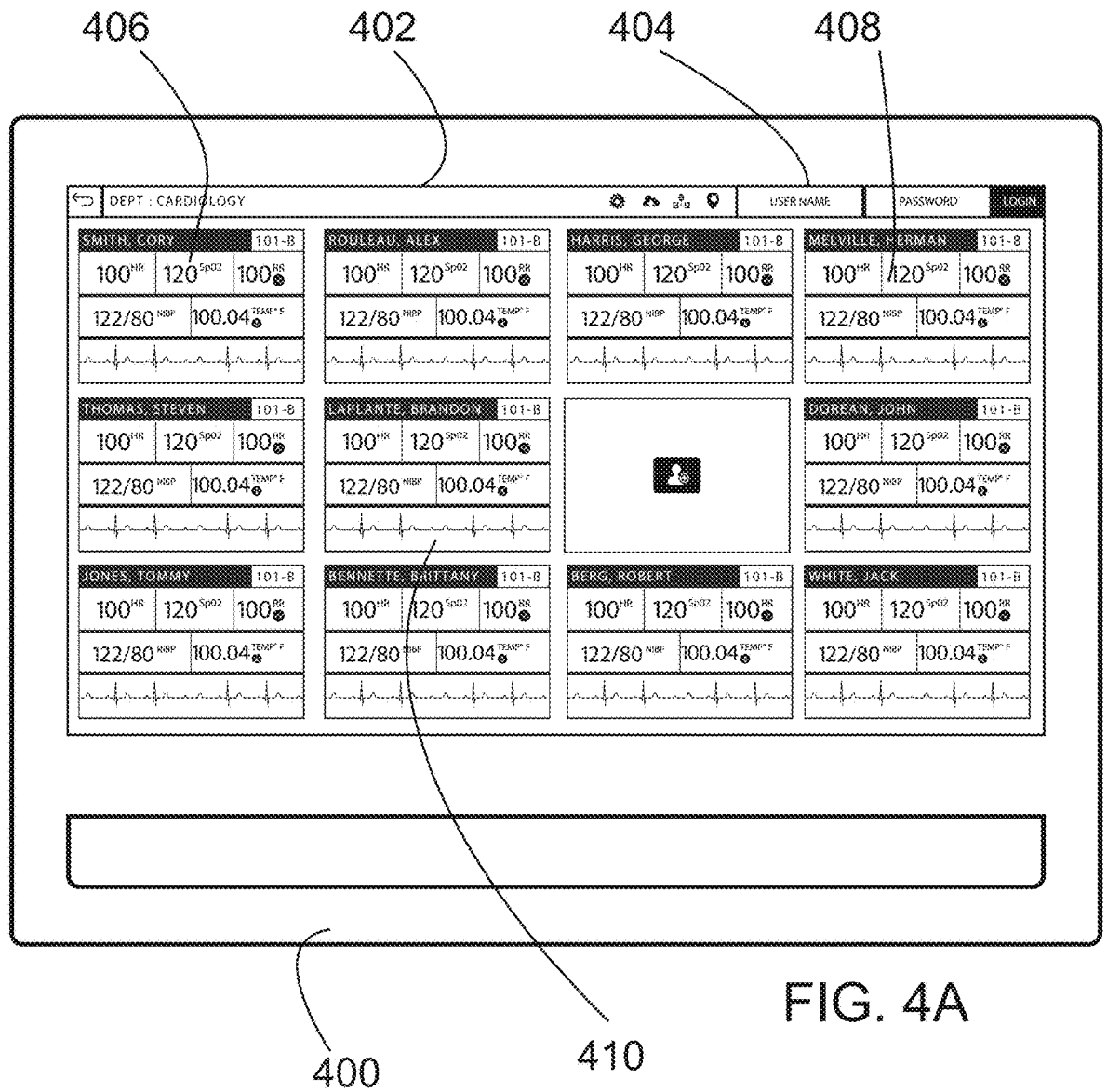
FIGS. 4A-4B show example graphical user interfaces for a central server station of a healthcare information system.

FIG. 4A shows a display 400 having a user interface 402. The display 400 can be part of a central server station in communication with a central server, such as, for example, the central server station 114 of FIG. 1 that is in communication with the central server 113. As described above, the central server can be a collection of multiple servers spread across different geographic locations that are accessible by multiple computing devices, such as a computing device that includes the display 400. The information displayed on the display 400 can be provided by the one or more servers located at various geographic locations. The user interface 402 can serve as a central aggregation point for multiple patients being monitored using one or more patient worn sensors assigned to each patient and each associated with one or more bedside monitors (or other monitors). The central server can receive information from the multiple bedside monitors and aggregate the information for display as part of the user interface 402. The user interface 402 can display the information for the multiple patients in a tiled manner, thereby providing a dashboard for patients located within a particular healthcare facility or a particular segment of a healthcare facility, or otherwise associated with a particular healthcare entity. This patient dashboard can present vital sign and other information for the multiple patients.

In the example shown in FIG. 4A, the user interface 402 shows information for a number of different patients that are currently being monitored. For example, each patient represented on the user interface 402 can be equipped with one or more patient worn monitors (e.g., chest monitors, arm pit monitors, wrist monitors, finger monitors, ear worn monitors, etc.) for monitoring vital signs of the patients. The information collected by the various patient worn monitors is transmitted to a central server through a network and displayed on the user interface 402. The user interface 402 indicates that the patients being monitored are patients associated with a cardiology department. However, each of the patients being monitored is not necessarily physically located in a cardiology department of a hospital. Some patients may be located in a general ward of the hospital, or may have been discharged and are being monitored from home or another environment outside of the hospital.

The user interface 402 includes a log-in field that can allow a user of the display 400 to log-in to a computer system for accessing patient information. For example, the user can enter a username and password to log-in to the system. Access to specific user information can be restricted to only users who have authorized access. In some implementations, different users can have different access levels. For example, a first user may only have access to a certain set of patients (e.g., only patients associated with cardiology, or only patients that are specifically assigned to the first user). As another example, a second user can access to a different set of patients, for example the second user may be assigned to a second, distinct group of patients and can only access information for the patients that are assigned to the second user. A third user may have access to information associated with all patients associated with the system. For example, the third user might be a chief doctor in charge of hospital administrative duties.

In some implementations, a particular user may only have permissions to access specific information for one or more patients. For example, a user of the system may have permission to access vital sign and treatment information for a patient, but cannot access insurance or financial information for the patient. As another example, a user may have permission to access information related to a current care plan for a patient, but cannot access information regarding past medical treatments for the patient.

In the example shown, the user interface 402 shows a vital sign information summary for a number of different patients. For example, a panel 406 shows vital sign information for a patient named Cory Smith while a panel 408 shows vital sign information for a patient named Herman Melville. Each of the panels included as part of the user interface 402 can include current information for a patient as well as historic information previously recorded for the patient, or manually entered for the patient.

For example, the panel 406 indicates that Cory Smith is located in room 1-B. The panel 406 additionally includes heart rate information, blood oxygenation level, respiratory rate, blood pressure, and temperature measurements for Cory Smith. The panel 406 also shows a heart rate waveform for Cory Smith.

In some implementations, if an alarm state for a particular patient is detected, the user interface 402 can alert a user of the display 400 by causing a panel associated with a patient experiencing the alarm state to start flashing, change color, become enlarged, or otherwise visually indicate an alarm state. For example, if Cory Smith's respiratory rate increases to above an upper acceptable bound, the panel 406 can flash to indicate an alarm state to a user of the display 400. In some implementations, a flashing box surrounding the panel 406 can appear to indicate that Cory Smith is currently experiencing an alarm state. The color of box can indicate a type of emergency or to indicate a severity of an emergency. For example, a red box can indicate a heart rate related alarm state, a green box can indicate a respiratory rate related alarm state, and a blue box can indicate a blood origination level related alarm state. As another example, a red box can indicate a highest tier (emergency) alarm state, a yellow box can indicate a mid-tier alarm state, a white box can indicate a low tier alarm state, and a green box can indicate a technical problem (e.g., loss of communication with a sensor, or low battery). In some implementations, a rate of flashing of an alert box surrounding a panel can be used to indicate the severity of an alarm state. For example, the more severe the alarm state, the faster the box can flash. Each of these alerts can also be combined with an audible alarm. In some implementations, different audible alarms can be used to indicate different alarm states or severity of an alarm state. The volume of an audible alarm can also be used to indicate the relative severity of an alarm state.

The display 400 can allow a user to select portions of the user interface 402 (e.g., using touch screen functionality of the display 400, a mouse, or other input device). The user can select a panel to view additional information for a patient associated with the selected panel. For example, the user can select a panel 410 to view additional information for a patient named Brandon LaPlante.

Figure 4B:
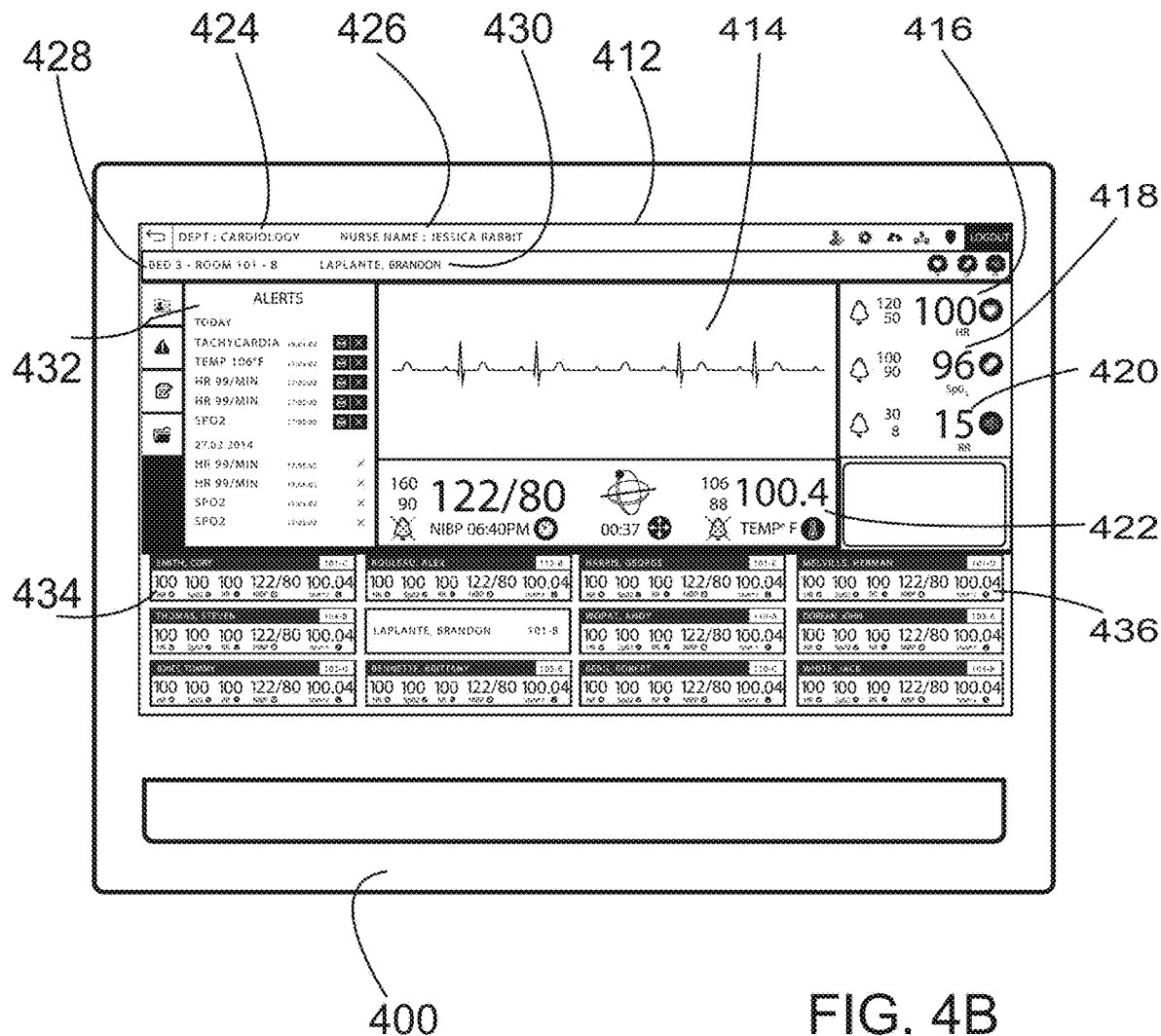

Turning to FIG. 4B, in some implementations, selection of the panel 410 causes a user interface 412 to be displayed. User interface 412 shows detailed information for the patient Brandon LaPlante. For example, the user interface 412 includes a heart rate waveform 414, a numeric heart rate value 416, a numeric blood oxygenation level 418, a numerical respiratory rate value 420 and a numeric body temperature value 422 for the patient. Additional information for the patient Brandon LaPlante is also displayed by the user interface 412, including additional vital sign information as described above with respect to FIG. 3C. The user interface 412 can also indicate if an alarm state is occurring with respect to the patient, e.g. by causing one or more portions of the screen to change color, flash, or display an alert indication icon.

The user interface 412 indicates a department associated with the patient (cardiology department, at 424), a caregiver responsible for monitoring the patient (Jessica Rabbit, at 426), a room and bed number assigned to the patient (Room 101-B, bed 3, at 428) and the patient's name (Brandon LaPlante, at 430). The user interface 412 further includes an alert panel 432 showing alerts for alarm states associated with the patient along with a time stamp for each of the alerts. For example, the alert panel 432 shows that the patient experienced tachycardia at 18:01:02 and that the patient experienced a blood oxygenation level alarm state at 17:05:02.

In addition to displaying information for the patient Brandon LaPlante, the user interface 412 also includes several panels displaying information for several other patients. For example, each of the panels shown in the user interface 402 of FIG. 4A can be reformatted into a smaller format for display at the bottom portion of the user interface 412. For example, a panel 434 shows vital sign information (heart rate, blood oxygenation, respiratory rate, blood pressure, and temperature) for patient Cory Smith, while a panel 436 shows vital sign for patient Herman Melville. In some implementations, if an alarm state occurs with respect to a patient associated with one of the displayed panels, a visual and/or audible alarm as described above with respect to FIG. 4A can alert a user of the display 400 to the alarm state. For example, if Herman Melville experiences cardiac arrest, a flashing red box can appear around the panel 436 to alert the user of the display 400 that Herman Melville is currently experiencing an alarm state.

Figure 5A:
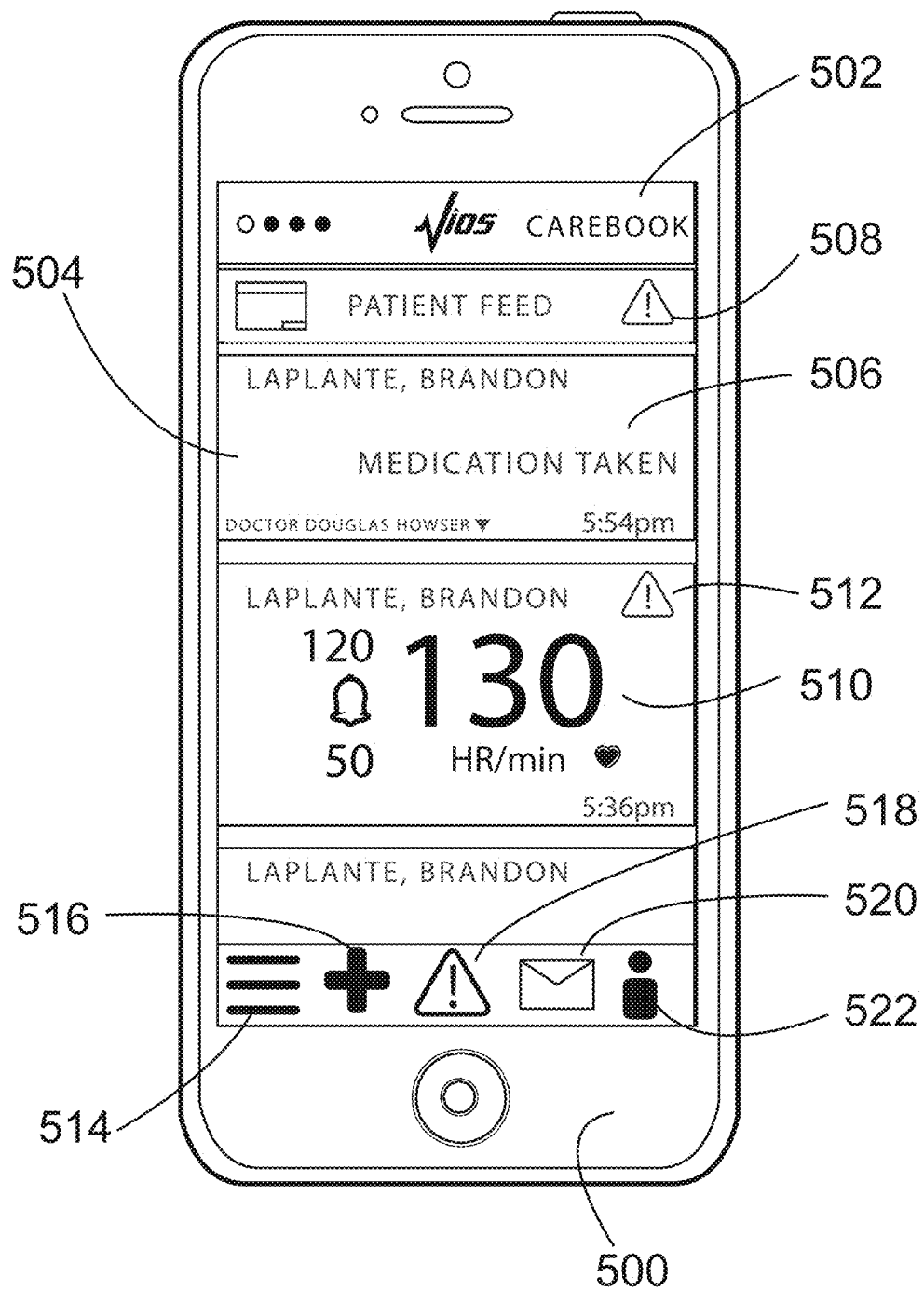
FIGS. 5A-5F show example graphical user interfaces of a caregiving network for a healthcare information system.

FIG. 5A shows a mobile device 500 having a user interface 502 that includes a patient newsfeed 504 displaying information associated with a patient. The mobile device 500 can, for example, belong to a caregiver associated with the patient (for example, a general care physician assigned to monitor the patient, a surgeon who performed surgery on the patient, a pharmacist assigned to the patient, etc.). The caregiver can access the patient newsfeed 504 by logging into a secure system through the mobile device 500. The system can verify the caregiver's credentials to determine that the caregiver has proper permissions to view information for the patient. The patient newsfeed 504 shows an information flow for the patient showing various healthcare related events and information associated with the patient. For example, a panel 506 indicates that the patient (Brandon LaPlante) took medication at 5:54 and that this note on medication was entered by Doctor Douglas Howser. The caregiver can scroll through the patient newsfeed 504 to view additional information for the patient that is not currently shown on the user interface 502. The information for the patient can be ordered, for example, by time that the displayed information was entered or recorded, importance of the information, or information type. Information displayed as part of the newsfeed 504 can include the occurrence of medical events related to the patient (e.g., medical procedures, medication administered, treatment performed) including time stamp information and notes on the medical events. The newsfeed 504 can further include vital sign information for the patient (e.g., as measured by a patient worn sensor affixed to the patient), historical medical care information for the patient, notes and other information entered by various caregivers associated with the patient, and other information related to the patient's health care.

The patient newsfeed 504 also includes an alert icon 508 indicating that an alarm state currently exists for the patient. The patient newsfeed 504 provides additional detail for the alarm state at panel 510. The panel 510 includes an alert icon 512 indicating an alarm state for the patient. The panel 510 indicates that the patient's heart rate is currently at 130 beats per minute (BPM). The panel 510 also shows an acceptable heart rate range of 50 BPM to 120 BPM for the patient. This allows the caregiver to readily identify how severe the increased heart rate for the patient is in comparison to a determined acceptable range for the patient. In some implementations, the caregiver can use the mobile device 500 to identify a current location for the patient to determine if the caregiver is near the patient's current location. If the caregiver determines that he is near the patient's location, the caregiver can potentially respond to the indicated alarm state.

In some implementations, the user can select various portions of the user interface 502 to access additional information. For example, the user can select the panel 506 to cause the mobile device 500 to display a user interface that includes additional information on historic medication administration for the patient and/or future scheduled medication administration times and other information associated with a medication plan for the patient. As another example, the user can select the panel 510 to cause the mobile device 500 to display a user interface containing additional information on tracked heart rate information for the patient. For example, heart rate information for the patient recorded at regular intervals for a specified time period can be displayed.

The user interface 502 includes additional controls to allow a user of the mobile device 500 to access additional information and control menus. For example, a control 514 allows the user to access a menu screen. The menu screen can allow the user to access additional information, change settings, or indicate alert preferences or viewing preferences. For example, the user can select the control 514 to cause the mobile device 500 to display a settings screen. As another example, the user can select the panel 510 to access a user interface that allows the user to change values for an acceptable heart rate range for the patient.

The user interface 502 can further include a control 516 that allows the user to input information. For example, the user can select the control 516 and the mobile device 500 can display an input box in response to the selection. The user can then enter a note for the patient. For example, the user can indicate that the patient is feeling light headed and indicate a time frame for this event. As another example, the user can enter a note indicating that swelling around a surgical incision has reduced since a previous inspection of the incision. In some implementations, the user can indicate a priority level for a note. For example, the user can select an "urgent" or "important" priority level for a particular note. In some implementations, the control 516 can be used to add a patient to the system. For example, the user can select the control 516 to create a new patient profile for a new patient. The user can enter information for the new patient such as the name of the new patient, historical health information provided by the patient or patient records, and notes on medical issues that have caused the patient to seek treatment.

The user interface 502 further includes a control 518 for accessing alerts. For example, the user can select the control 518 to cause the mobile device 500 to display current alerts for the patient, past alerts for the patient, alerts that occurred within a specified time frame (e.g., the past week) or alerts associated with multiple patients. Such an alert screen can allow the user to access information on patient alarm states that prompted each alert, information that allowed the system to identify the alarm state, how the alarm states were resolved, and status of the patient after the alarm states were resolved. In some implementations, the alert screen accessed by selecting the control 518 only shows active alerts (i.e., alerts for unresolved alarm states) for patients associated with the user of the mobile device 500. For example, the user can be a nurse on duty on in a particular hospital ward. The mobile device 500 can receive an alert message and alert the nurse by emitting an audible alarm, flashing, or vibrating. The nurse can look at the user interface 502 which can cause the control 518 to flash to indicate that an alert message has been received. The nurse can then select the control 518 to view information for the alert that can allow the nurse to respond to the alert. For example, upon selection of the control 518, the mobile device 500 can indicate that a patient located in room 309C Bed 2 is currently experiencing an accelerated respiratory rate.

The user interface 502 includes a control 520 to allow the user to send messages to other caregivers or other users of the system. For example, the user can send a message to a pharmacist indicating that the user believes that medication dosage for the patient should be increased and asking the pharmacists opinion. In some implementations, the user interface of the mobile device 500 can allow the user to readily include information about one or more patients in a message. For example, the mobile device 500 can allow the user to select recent information items from the patient newsfeed 504 to include in the message. In some implementations, the user interface allows the user to select from a list of caregivers associated with the patient to address a message to caregivers selected from the list.

In some implementations, the patient newsfeed 504 is provided to the user of the mobile device 500 as a user interface for interacting with a caregiving network of a hospital information system. The caregiving network can be administered by one or more servers and include profiles for patients, caregivers, and other caregiving network participants. The profiles can be linked to each other to form various user specific care groups and facilitate communication of information between participants of the caregiving network. For example, the user can be a caregiver and a caregiver profile (stored at one or more central servers) can be associated with the caregiver. The caregiver profile can include information for the caregiver, such as name, age, job title, areas of expertise, healthcare department, contact information (email, phone number, address, etc.), and a profile picture for the caregiver. The caregiver profile can also include links to patient profiles for patients that the caregiver is responsible for or associated with. For example, patient profiles for patients assigned to a general ward nurse can be linked to the nurse's caregiver profile. As another example, patient profiles for patients that are scheduled to have operations performed by a particular surgeon, or whom have recently had operations performed by the surgeon can be linked to the surgeon's caregiver profile. The caregiver profile can also be linked to other caregiver profiles. For example, caregiver profiles for caregivers in a particular department, or assigned to a particular ward can be linked to each other. As another example, the caregiver profile for the caregiver can be linked to a caregiver profile for the caregiver's supervisors. The caregiving network can include a plurality of patient profiles and caregiver profiles that are linked to each other to form the caregiving network and facilitate communication between linked parties and efficient exchange of information. The patient newsfeed 504 can be displayed as part of the functionality provided by the caregiving network.

Patient profiles can be linked to several caregiver profiles. For example, a patient profile can be linked to caregiver profiles for an attending physician assigned to the patient, one or more nurses assigned to monitoring the patient, one or more orderlies responsible for an area of a healthcare facility where the patient is located, caregivers associated with a future scheduled or past surgical procedure for the patient, physical therapists assigned to the patient, pharmacists responsible for the patient's medication schedule, and other caregivers associated with the patient. The caregivers having caregiver profiles linked to the patient's patient profile make up the patient's care group. The patient's care group can be continuously (and in some cases, dynamically) updated through the addition or removal of caregivers from the patient's care group. For example an emergency room physician can be added to the patient's profile due to the physician performing emergency surgery on the patient to set a broken bone. The physician can remain in the patient's care group for a specified time, and later be automatically removed from the patient's care group when the patient has been out of the emergency room environment for a specified period of time (e.g., the patient's physical location as determined by the system is a location somewhere other than the emergency room for a specified period of time). As another example, a nurse in charge of supervising patient care for a particular ward or health facility location can be automatically added to the patient's care group (by linking the nurse's caregiver profile to the patient's patient profile) when the patient is relocated to the particular ward or health facility location.

A healthcare system can dynamically create, update, or dissolve care groups based on information for a patient, changing patient condition (including changes in vital sign information recorded, for example, by a patient worn sensor), progression of a patient along a recovery schedule, change in treatment for a patient, or change in caregiver circumstances. Care groups can be dynamically updated to reflect the reality that certain actors and certain entities (e.g., caregivers and healthcare entities such as specific treatment facilities) will have interests in a patient's condition, treatment, and recovery progress at different points in time in different degrees. For example, an anesthesiologist could be included in a patient's care group for a limited portion of time preceding a surgery, during the surgery, and during a period of time sufficient for initial recovery of the patient immediately after surgery.

The healthcare system can collect information about a patient and information related to the patient, the patient's condition, and the patient's medical care to dynamically create one or more care groups for the patient and to dynamically add or remove caregivers or other persons to or from the patient's care group. Factors that can be assessed by the system when adding or removing care group members can include patient treatment information, medical history of the patient, patient vital signs (e.g., as collected by a patient worn sensor), patient location, care giver location, indications of one or more events having occurred or not occurred, time since the occurrence of an event, time and date, or any combination of these factors and other factors.

For example, a surgeon may only be concerned with a patient leading up to surgery, during surgery, and during an initial recovery phase after surgery, but not for the entire recovery phase for the patient. The surgeon can be automatically added to the patient's care group for a time frame in which the surgeon has an interest in the patient's status and recovery, and then removed from the patient's care group after the time in which the surgeon has a direct interest in the patient's recovery and treatment. This can be, for example, a set time frame after the completion of the surgery. In this example, the system can identify that a set time period (e.g., twelve hours) has elapsed since the completion of surgery and that the patient's vital signs are currently at stable levels. The system can additionally access information (e.g., entered manually by surgical nurse who participated in the surgery) indicating that no complications occurred during the surgery and that the surgery was completed successfully. Based on this collection of information, the system can determine that the surgeon no longer needs to be notified of changes in the patient's condition and automatically remove the surgeon from the patient's care group.

As another example, the system can identify that a patient is scheduled for knee surgery, or that the patient has recently had a knee surgery. The system can identify that the patient requires physical therapy and automatically add a physical therapist having the required credentials for assisting patient's in recovering from knee surgery to the patient's care group. The system can also automatically schedule one or more therapy sessions with the physical therapist. Later, the system can identify that the patient has attended all required physical therapy sessions (e.g., based on information manually entered by the physical therapist or another caregiver, or based on identifying that the patient was physically located in the physical therapy room for three different two hour time periods). Based on this determination, the system can automatically remove the physical therapist from the patient's care group since the patient has completed all necessary physical therapy sessions. In some implementations, the physical therapist is not removed from the patient's care group until a set period of time after the final physical therapy session (e.g., so that the physical therapist is kept apprised of any possible adverse effects of the physical therapy).

In some implementations, the system can use vital sign information (e.g., real-time vital sign information collected by a patient worn sensor) in determining whether to add or remove a caregiver or other care group member from the patient's care group. For example, the system can remove a surgeon from the patient's care group a set amount of time after successful completion of surgery only after the system has verified that the patient's vital signs are within pre-specified "normal" or "stable" ranges (or after verifying that the patient's vital signs have been within pre-specified normal ranges for a specified duration of time). If one or more vital signs for the patient is not within a pre-specified normal range, the surgeon can be kept in the patient's care group since the surgeon may want to monitor information for the patient to assure that there are no unexpected post-surgery complications. In other words, the surgeon is kept in the patient's care group since the surgeon may want to be informed of the patient's status for a longer period of time than if all vital signs for the patient were within pre-specified normal ranges.

As another example, the system can monitor vital sign information and dynamically add caregivers to the patient's care group based on changes in vital signs for the patient, or based on one or more vital signs reaching a particular level for a specified period of time. For example, the system can receive blood sugar level information for a patient. The system can identify that the patient's blood sugar level is above a specified level for longer than a specified period of time. The system can automatically generate an alert and transmit the alert to one or more care givers in the patient's care group. The system can further identify a specialist who specializes in treating diabetes and other blood sugar related ailments and automatically add the specialist to the patient's care group. Additionally, in response to identifying the patient's high blood sugar condition, the system can automatically schedule a consultation session between the patient and the specialist (including identifying a time for the consultation session, and a location of the consultation session).

As yet another example, a patient may be admitted to the hospital after being involved in a car accident. The patient can be initially treated in the ER, outfitted with a patient worn sensor, and subsequently moved to a general ward of the hospital. At this point, the patient's care group does not include a cardiologist since the patient was not admitted for a heart condition. The system can track the patient's vital signs using the patient worn sensor, and use this vital sign information to detect an irregular heart pattern for the patient. In addition to generating an alert message and providing the alert message to one or more care givers in the patient's care group (e.g., a nurse located near the patient's room) the system can identify a cardiologist on duty and automatically add the cardiologist to the patient's care group in response to identifying the irregular heart pattern.

In some implementations, changes in information other than information directly related to the patient is used in automatically adding or removing care givers to/from the patient's care group. For example, a patient may need an organ transplant and be placed on an organ transplant waiting list. The system can determine when an organ that matches requirements for the patient becomes available. The system can further identify patient information (such as caregiver entered information and detected vital sign information) to identify that the patient is in suitable condition for having organ transplant surgery, and that the patient has no progressed to a point where an organ transplant procedure is no longer feasible or advised. The system assesses the information, and makes a determination that the available organ matches the patient's requirements and that the patient is in a sufficiently stable condition to have the organ transplant surgery. In response to the organ becoming available and the positive determination made by the system, the system can automatically identify one or more surgeons, surgical nurses, physicians' assistants, and/or other medical care professionals to perform the transplant surgery and participate in the immediate recovery of the patient. Each identified care giver is then automatically added to the patient's care group. These various care givers can later (after the surgery) be automatically removed from the patient's care group at various points in time as described in the above examples.

In some implementations, when patient events (e.g. alarm states) occur for a patient, notifications can be transmitted to some or all caregivers included in the patient's care group. In some implementations notifications can be transmitted to all caregivers in the patient's care group, only caregivers identified as being related to a particular event, only caregivers currently on duty, or only caregivers that are within a specified proximity of the patient. The notifications can include information on the patient event, including vital sign information for the patient (e.g., information collected from one or more patient worn sensors) and other information associated with the patient event (such as information used to identify a current alarm state for the patient). For example, the user of the mobile device 500 can receive notifications related to patients in the user's care group (patients with which the user is an associated caregiver) which can be displayed as part of the user interface 502.

The caregiver can access the caregiving network by logging in using a unique caregiver ID and password. The caregiver can log in using the mobile device 500 or another computing device capable of communicating with one or more central servers. For example, referring to FIG. 1, access to the caregiving network can be controlled by the central server 113, and the caregiver can access the caregiving network by logging in at the bedside monitor 108, central server station 114, or another computing device in communication with the network 112. Returning to FIG. 5A. The caregiver can access the patient newsfeed 504 using caregiving network functionality of the system that is accessible using the mobile device 500. For example, a patient profile for the patient Brandon LaPlante can be linked to the caregiver's caregiver profile. The caregiver can select Brandon LaPlante from a list of patients associated with the caregiver profile to view information for Brandon LaPlante. The information can be displayed to the caregiver in the form of the patient newsfeed 504. In some implementations, a patient newsfeed displayed on the mobile device 500 can include information for multiple patients. For example, the caregiver can select an option to view information for each patient having a patient profile that is currently linked to the caregiver's caregiver profile. In some implementations, a patient profile can have a designation indicating whether the patient associated with the patient profile is an active patient.

This can allow the caregiver to elect to only view information for patients having patient profiles indicating that the patients are active patients.

The caregiver can link her profile to patient profiles for various patients or caregiver profiles for other caregivers using various different techniques. Some techniques allow for manual linking of the caregiver's profile with patient profiles and other caregiver profiles while other techniques automatically link the caregiver's profile to other patient and caregiver profiles. One way in which the caregiver can link to other profiles is by searching for patients or other caregivers by name, patient ID, caregiver ID, or another unique identifier. For example, the caregiver can access a search screen to search for patient profiles and enter the name "Brandon LaPlante." If a patient profile for Brandon LaPlante exists in the system, the caregiver can select a link to the patient profile for Brandon LaPlante. The system can verify that the caregiver has proper permissions to access some or all of the information included in the patient profile for Brandon LaPlante. If the system determines that the caregiver is permitted to access the patient profile for Brandon LaPlante, the system can display information from the patient profile that the caregiver is permitted to access. The caregiver can then link the patient profile for Brandon LaPlante to the caregiver's caregiver profile. Later, the caregiver can elect to unlink her caregiver profile from the patient profile for Brandon LaPlante. As another example, if Brandon LaPlante is discharged from a hospital at which the caregiver works, the patient profile for Brandon LaPlante can be automatically unlinked from the caregiver's caregiver profile.

In some implementations, patient profiles or caregiver profiles can be automatically linked to the caregiver's caregiver profile. For example, a patient profile for a patient can be linked to the caregiver profile based on the system identifying a scheduled future medical occurrence for the patient. For example, the patient can be scheduled to receive a heart operation at a specific time and date and this information, as well as an indication of the surgeon performing the operation, can be included in the patient profile (e.g., either from being manually entered, or automatically entered by the system). The system can then identify a surgical attendant nurse that is scheduled to work during the time of the operation who is not currently occupied during that time period and is qualified to assist with the specified type of operation. The system can automatically assign the surgical attendant nurse to the operation and automatically link the patient profile to a caregiver profile for the surgical attendant nurse. The system can further identify an anesthesiologist that is scheduled to be on call during the time period for the operation who is not already scheduled for a procedure during that time period and who is qualified to assist with the procedure. The system can automatically link a caregiver profile for the anesthesiologist to the patient profile.

As another example, a patient profile for a patient can indicate that the patient is to go for a 15 minute walk every day at approximately 4:00 pm. The system can identify an orderly that is scheduled to work during the specified time period of the patient's walks, determine that the orderly is not busy with other responsibilities during those time periods, assign the orderly to be in responsible for assisting the patient with the walks, and automatically link a caregiver profile for the orderly to the patient's patient profile. As yet another example, the system can identify that a particular nurse has entered notes into a patient's patient profile regarding medication administration for the patient on several occasions. The system can use this information to determine that the nurse is associated with the patient and automatically link the patient's patient profile to the nurse's caregiver profile. In another example, the system can automatically link patient profiles for all patients assigned to a particular ward, or located on a particular section of a floor to a caregiver profile for an attending caregiver that is in charge of supervising care for all patients within the particular ward or the particular section of the floor.

In some implementations, caregiver profiles can be automatically unlinked from patient profiles based on one or more factors. For example, a caregiver profile for a surgeon can be linked to a patient profile for a patient prior to a scheduled surgery for the patient to be performed by the surgeon. The surgeon's caregiver profile can remained linked with the patient profile for a period of time after the surgery so that the surgeon can readily access information for the patient to assess whether recovery immediately after the surgery is proceeding normally, or if any complications from the surgery have arisen. After a specified period of time after the surgery has elapsed, the surgeon's caregiver profile can be automatically unlinked from the patient profile since the surgeon is no longer directly related to the patient's care after the elapsed time.

As mentioned above, the user of the mobile device 500 can use the control 514 to access various menus for the user interface 502, including a settings interface for changing various information viewing settings. The user can use the settings screen to set preferences for the presentation of information in the newsfeed 504 or other information provided by the user interface 502. The user can apply filters to identify specific types of information to display as part of the patient newsfeed 504. This functionality allows the user to create a customized newsfeed that includes information that is most relevant to the user based on specified preferences of the user. The customized newsfeed can include information from one or more patient profiles linked to the user's caregiver profile in a customized manner specified by the user to allow the user to more efficiently monitor the status of patients under the user's care. In some implementations, the user can apply different information filter settings for different patients. This can include setting different information filter settings for different types of patients. For example, the user can prioritize a first set of information for patients recovering from heart surgery, a second set of information for patients being treated for respiratory problems, and a third set of information for patients recovering from head injuries.

Another example of criteria that can be used to specify information to display as part of a customized newsfeed for the user includes alert/alarm priority. For example, the user can change settings to specify that alerts indicating alarm states for patients associated with the user (e.g., patients having patient profiles linked to the user's caregiver profile) are to be given priority over other information and placed at the top of the patient newsfeed 504. The user can further specify that alerts having higher severity levels be given the most prominent locations within the patient newsfeed 504. For example, a tier one alert would be placed above a tier two alert. As another example, the user can specify that technical alerts (e.g., low battery for a patient worn sensor) are not to be given specialized priority over other information in the patient newsfeed 504.

Other factors that can be used to specify display layout for the patient newsfeed 504 can include the time stamp of events/information (e.g., information is displayed in chronological or reverse chronological order of when it was entered or received). The layout of information in the patient newsfeed 504 can also be specified based on physical location of patients (e.g. proximity to the mobile device 500, or location within a particular healthcare environment). For example, information for one or more patients within close proximity to the physical location of the mobile device 500 can be displayed at the top of the patient newsfeed 504 while information for patients located further away from the mobile device 500 can be given lower priority. For example, the user can be an attending physician. As the physician makes rounds, the physician carries the mobile device 500 around with her. As the physician moves from room to room, location identification functionality of the mobile device 500 (e.g., a GPS unit, RF triangulation unit, or other location detection unit) continually identifies the changing location of the mobile device 500. As the physician enters a room, the mobile device 500 can determine its own current location, and update the patient newsfeed 504 to bring information for one or more patients located in or associated with the room in which the physician is currently located to the top of the patient newsfeed 504.

As another example, profile display preference information can specify that users located within a specified healthcare environment can be given priority such that information associated with the identified patients is more prominently presented by the patient newsfeed 504 (e.g., at the top of the patient newsfeed 504). For example, the user can specify that information for patients located in a recovery room is to be given priority over information for patients located in a general ward. As another example, the profile display preference information specifying that information for patients located in an ER of a healthcare facility are to be given priority over information associated with patients who have been discharged from the healthcare facility can be accessed and used to format information included in the patient newsfeed 504 for display to the user.

Other display preferences that can be set by the user include color schemes, text size (including variable text size for information having different priority levels) and general information positioning and layout. For example, the user can specify that information panels (such as the panels 506 and 510) scroll horizontally rather than vertically, or specify another layout for the information displayed by the user interface 502.

Figure 5B:
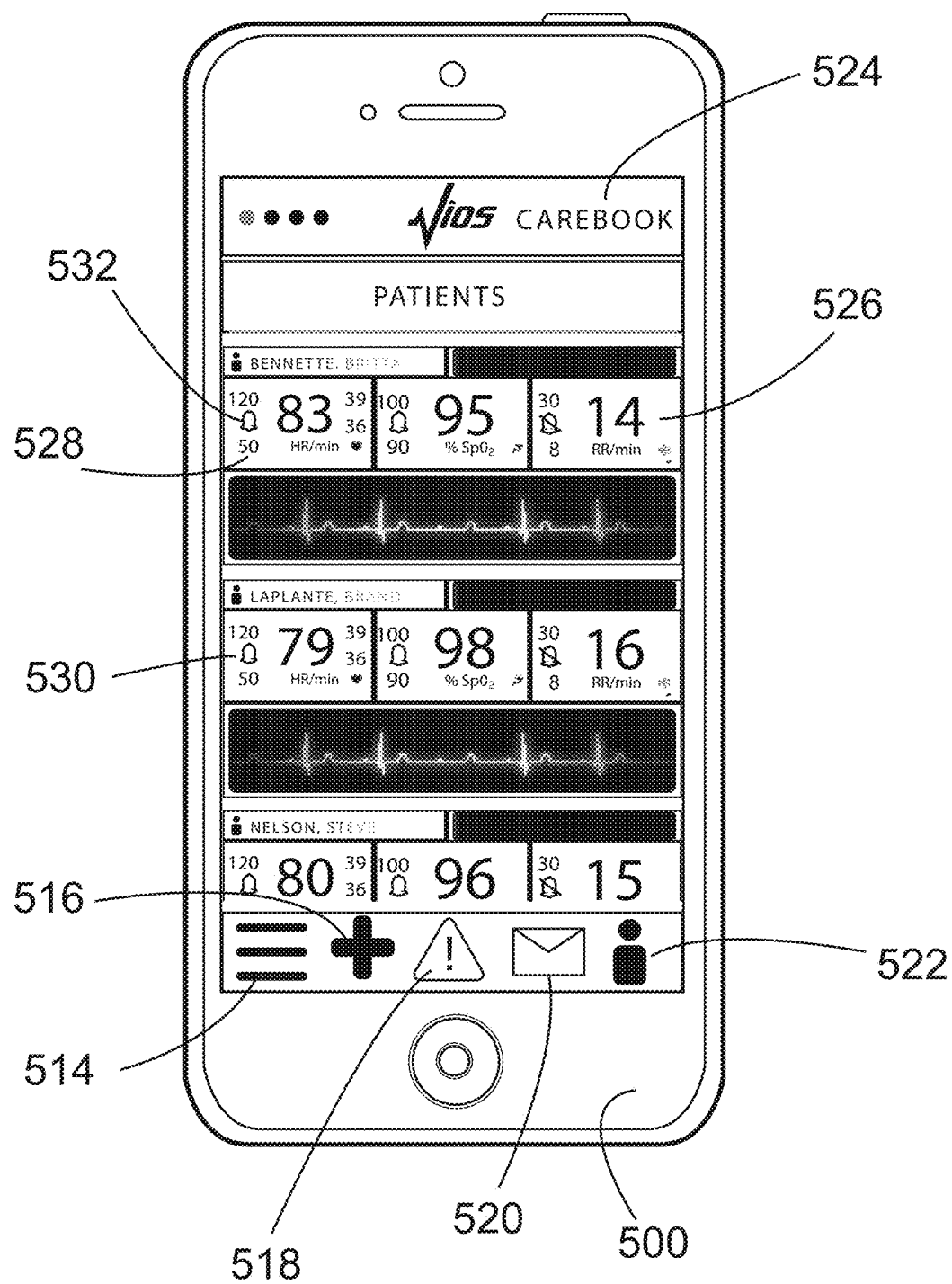

Turning to FIG. 5B, the mobile device 500 shows a user interface 524 that includes a newsfeed 526. The newsfeed 526 displays vital sign information for a number of different patients. For example, the mobile device 500 can belong to a caregiver who has logged into the caregiving network system. The caregiver can have a caregiver profile as described above and the caregiver profile can be linked to patient profiles for multiple patients. The newsfeed 526 can allow the caregiver to view vital sign information and other information for each patient having a patient profile linked to the caregiver's caregiver profile. For example, the newsfeed 526 includes a panel 528 showing vital sign information (heart rate, blood oxygenation, respiratory rate, and a heart rate waveform) for a first patient as well as specified acceptable ranges for each of these vital signs for the first patient. The newsfeed 526 further includes a panel 530 showing vital sign information and specified acceptable vital sign ranges for a second patient. The newsfeed 526 can include more or less information for patients than is shown in the example in FIG. 5B. For example, blood pressure or orientation for each patient could be included in the newsfeed 526. As another example, a current assigned room number and bed number for each patient can be displayed as part of the newsfeed 526. As yet another example, the newsfeed 526 can display a medication schedule for each patient that shows what medications have been prescribed to the patients, when they have been administered, and when they are scheduled to be administered in the future.

The newsfeed 526 can also indicate alarm states for one or more patients having patient profiles linked to the caregiver's caregiver profile. For example, an alert icon 532 can change color, or begin flashing if an alarm state related to a heart rate for the first patient has been detected. For example, the alert icon 532 can begin flashing if the first patient begins experiencing tachycardia. As another example, a box can appear surrounding a panel that includes information for a patient to indicate that an alarm state for the patient has been detected. For example, a flashing box that encircles the panel 530 can be displayed on the user interface 524 to indicate that an alarm state is presently occurring for the second patient. The alarm state can be related to one of the presently displayed vital signs (e.g., irregular breathing) or to another vital sign or other information associated with the second patient (e.g., a patient worn sensor has detected that the patient has fallen).

In some implementations, layout of information included as part of the newsfeed 526 or the type of information included as part of the newsfeed 526 can be based, at least in part, on specified user preferences of the user of the mobile device 500. For example, the user can select the control 514 to access a settings menu and change display preferences for the user interface 524 as described above with reference to FIG. 5A. For example, the information displayed as part of the panel 528 can be given priority over the information included in the panel 530 based on user preferences specifying that information associated with the first patient (shown in panel 528) is of higher priority than information associated with the second patient (shown in panel 530).

Figure 5C:
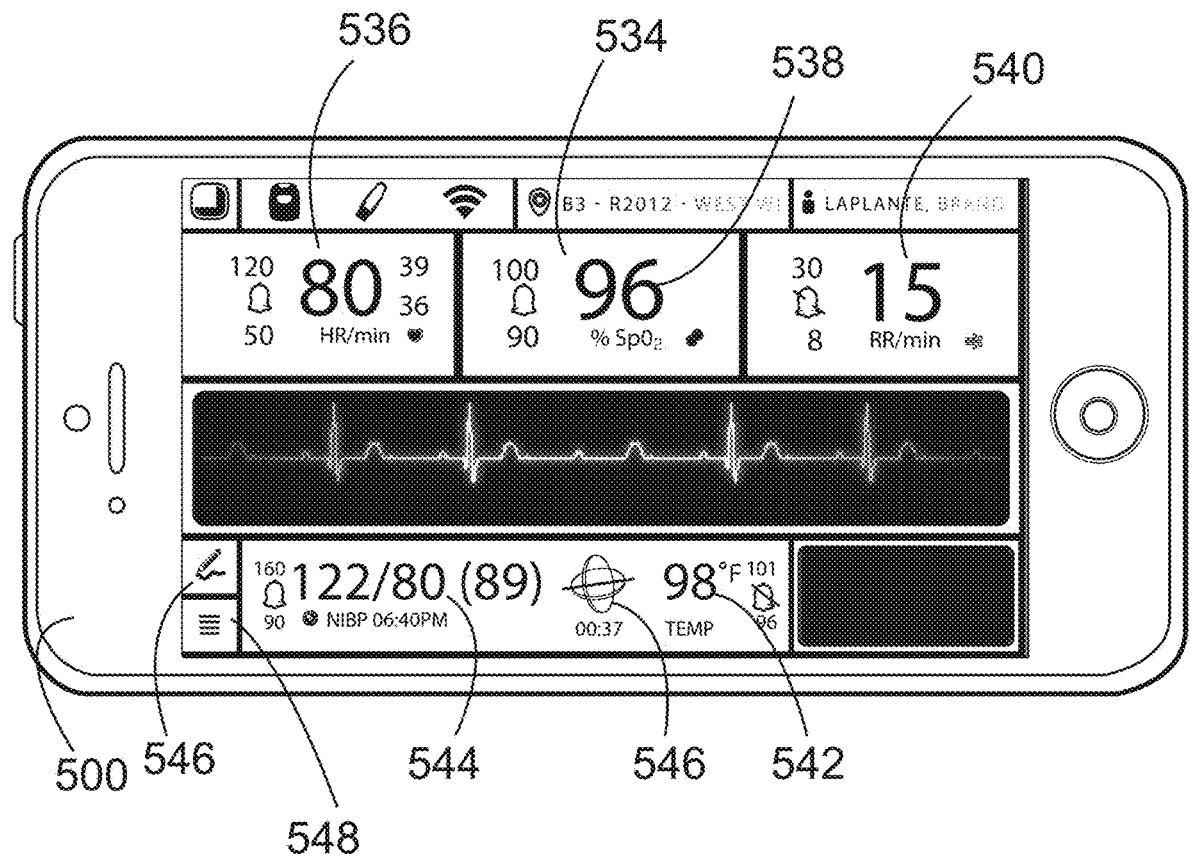

In some implementations, portions of the newsfeed 526 are selectable to allow the caregiver to access additional information about patients having profiles linked to the caregiver's profile. For example, the caregiver can select the panel 528 to cause the mobile device 500 to display a user interface 534 as shown in FIG. 5C. The user interface 534 shows vital sign and other information for the patient associated with the panel 528 selected from the newsfeed 526. The information included in the user interface 534 is similar to the information shown as part of the user interface 330 in FIG. 3C in the context of a bedside monitor or the user interface 412 shown in FIG. 4B in the context of a central server station with the information being specifically configured for display on a mobile device. For example, in the example shown in FIG. 5C, the user interface 534 includes a numeric heart rate value 536, a numeric blood oxygenation level 538, a numerical respiratory rate value 540, a numeric body temperature value 542, a blood pressure value 544, and an orientation indicator 546 for the patient. Additional information for the patient Brandon LaPlante is also displayed by the user interface 534, including the patient's name, a room number for the patient, and a bed number for the patient. The user interface 412 can also indicate if an alarm state is occurring with respect to the patient, e.g. by causing one or more portions of the screen to change color, flash, or display an alert indication icon.

The user interface 534 further includes a control 546 that allows the caregiver to enter notes for the patient. For example, the caregiver can select the control 546 and make a note that the patient has been experiencing dizziness. As another example, the caregiver can enter a note indicating that the patient missed a scheduled physical therapy appointment. The user interface 534 also includes a control 548 to allow the caregiver to access a menu screen. The menu screen can allow the caregiver to change settings, access additional information for the patient, change to a different display screen, view the patient's patient profile, view the caregiver's caregiver profile, or view information for other patients.

In some implementations, layout of information included as part of the user interface 534 or the type of information included as part of the user interface 534 can be based, at least in part, on specified user preferences of the user of the mobile device 500. For example, the user can select the control 548 to access a settings menu and change display preferences for the user interface 534 as described above with reference to FIG. 5A. For example, the user can specify that heart rate and respiration rate information for the patient should be displayed by the user interface 534, but that information on blood pressure and blood oxygenation should not be included. In some implementations, rather than specifying the display preferences for the specific patient, the user can specify display preferences based on a patient type or treatment category for the patient. For example, the user can specify that one set of vital signs should be displayed for patient's recovering from burn related injuries while a second set of vital signs should be displayed for patient's going through physical therapy for improving motor function skills.

Figure 5D:
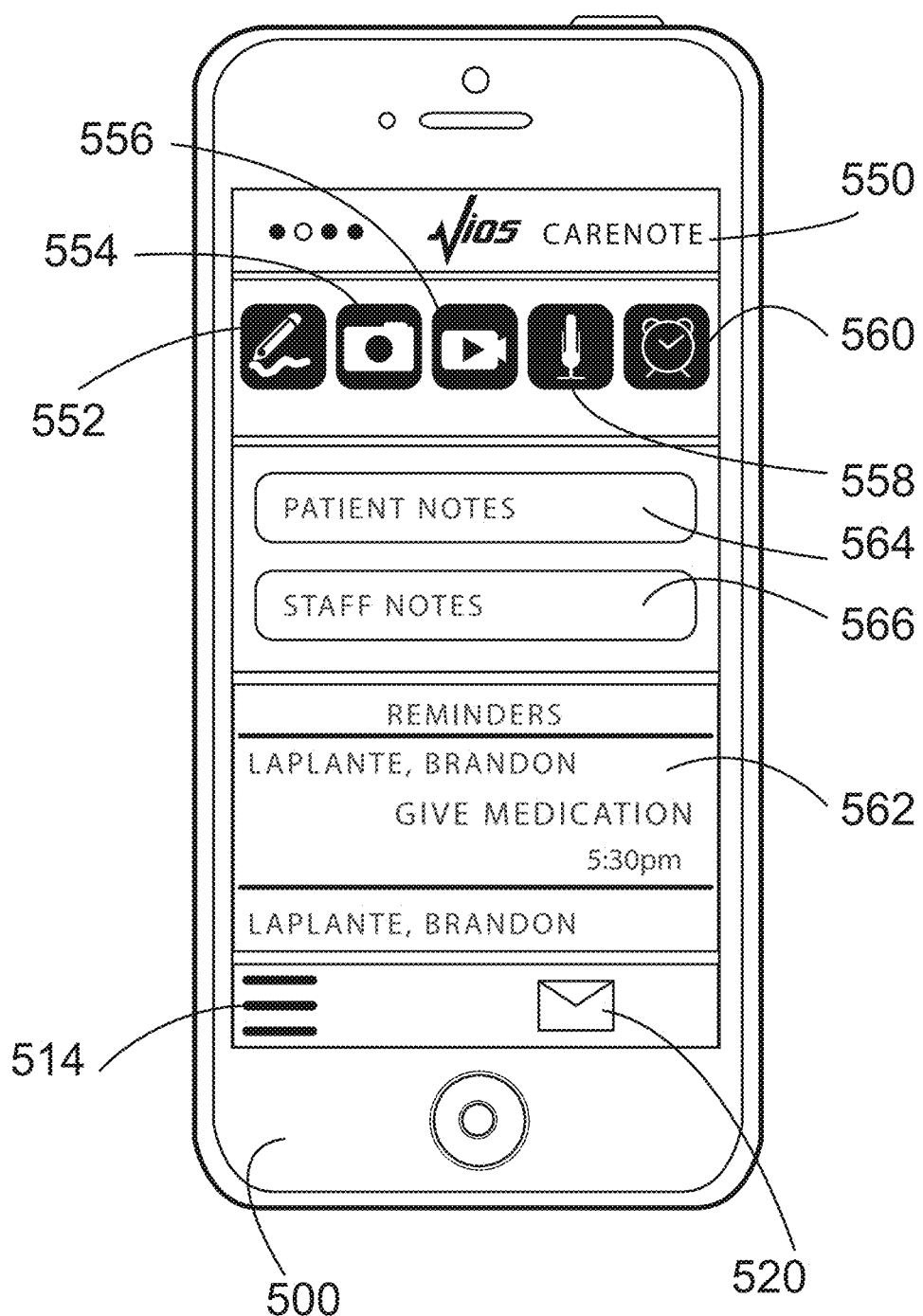

FIG. 5D shows a user interface 550 for entering information associated with a patient and viewing information associated with the patient displayed on the mobile device 500. The user interface 550 includes a control 552 to allow a user of the mobile device 500 to enter information for the patient Brandon LaPlante. The user can select the control 552 to enter a text note for the patient. For example, the user can select the control 552 and enter text stating "surgical incision is healing nicely, minimal swelling and no signs of infection." As another example, the user can select the control 552 and enter text stating "check in with patient on May 3, 2013 regarding response to increase in medication dosage."

The user interface 550 also includes a control 554 that allows the user to associate pictures and images with the patient (for example, by posting the images to the patient's patient profile). Images posted to the patient's profile can assist with diagnosis, treatment, or prolonged care for the patient. In some implementations, the user can mark the images to the attention of one or more other caregivers to solicit input from the indicated caregivers. For example, the user can use a camera of the mobile device 500 to take a picture of a rash on the patient's skin and post the picture to the patient's profile. The user can then mark the picture to the attention of one or more other caregivers to solicit opinions on what is causing the rash or how to treat it. As another example, the user can use the mobile device 500 to retrieve a picture from a stored location and add the picture to the patient's profile. For example, the user can take a picture using a digital camera, load the picture onto a computing device, access the picture (e.g., through a network connection) using the mobile device 500, and then post the picture to the patient's profile.

As another example, the user can post images indicating certain treatment procedures for the patient. For example, a doctor can post an image including instructions and examples for properly changing dressing for a wound to the patient's profile. The patient can later access the image and follow the instructions to dress a wound after the patient has been discharged from a healthcare facility. As another example, a physical therapist can post images containing instructions on how to perform rehabilitative exercises. The patient can later access the images to assist the patient in performing the exercise on his own.

In some implementations, the control 554 can be used to capture screen shots of vital signs for the patient (such as the information displayed as part of the user interface 534 shown in FIG. 5C). The screen shots can then be attached to the patient's patient profile as a note. The user can make annotations to the image as part of the note. Additionally, a snapshot of one or more vital signs can be taken and added to text notes, video notes, calendar entries, or other notes for the patient. For example, the user can notice an abnormal heart rhythm for the patient. The user can take a snapshot of the waveform of the abnormal heart rhythm, add text notes, and then post the notes and the snapshot to the patient's profile. The user can mark the note/snapshot to the attention of a cardiologist who can then receive an alert prompting him to observe the note. The cardiologist can then look at the waveform snapshot and notes left by the user and recommend a course of action for the patient.

The user interface 550 includes a control 556 to facilitate posting of videos to the patient's profile. For example, rather than leaving a text note using the control 552, the user can record a video message for one or more other caregivers regarding status or treatment of the patient and post the video for the other caregivers to view. In some implementations, the user can mark posted videos to the attention of one or more other caregivers to solicit input from the indicated caregivers. Video messages can allow the user to get into more detail than would be allowed by a short text note, or provide visual and audio demonstrations simultaneously. Videos can also allow for more detailed explanations of complex scenarios and allow video images of the patient to be included. For example, if the patient is having problem with motor skills, the user can take a video of the patient walking, post the video to the patient's profile, mark the video to the attention of one or more physical therapists, and receive feedback from the physical therapists regarding techniques for improving the patient's walking ability.

The user interface 550 includes a control 558 to facilitate posting of audio messages to the patient's profile. For example, rather than leaving a text note using the control 552, the user can record an audio message for one or more other caregivers regarding status or treatment of the patient and post the audio message for the other caregivers to view. In some implementations, the user can mark posted audio messages to the attention of one or more other caregivers to solicit input from the indicated caregivers. Audio messages can allow the user to get into more detail than would be allowed by a short text note including allowing for more detailed explanations of complex scenarios.

The user interface 550 includes a control 560 to allow the user to enter reminders for future scheduled events associated with the patient. For example, selection of the control 560 can cause the mobile device 500 to display an input screen allowing the user to make a calendar entry for the patient profile. The user can, for example, add an entry for a future surgical procedure for the patient. In some implementations, the system can use information from the calendar entry to identify other resources to reserve for the surgical procedure. For example, the system can automatically identify a surgery room that is appropriate for the surgical procedure (based on a procedure type for the surgical procedure), verify that the identified room is not currently reserved for the necessary time frame, and reserve the room for the surgical procedure. The system can also automatically identify caregivers (e.g., surgeons, attending nurses, physicians assistants, pharmacists, anesthesiologists, etc.) having the appropriate skills for performing or assisting with the surgical procedure who are not otherwise engaged during the applicable time frame and schedule the identified caregivers to participate in the surgical procedure. The system can then send notifications to each of the identified caregivers and link the patient's patient profile to caregiver profiles for each of identified caregivers (thereby adding the caregivers to the patient's care group).

As another example, the user can select the control 560 and enter in a regularly scheduled event for the patient, such as indicating that medication is to be administered to the patient at 8:30 am and 4:30 pm every day for the next eight days. The user can include notes along with the scheduled event such as medication types and dosage. The user can also indicate one or more caregivers to be alerted to the regularly scheduled event, such as an orderly responsible for the specified time frames where the patient is located. In some implementations, the system can automatically associate a caregiver with a scheduled event. For example, the system can automatically identify a first orderly who is responsible for the patient's location in the morning and a second orderly who is responsible for the patient's location in the afternoons and automatically notify the first and second orderlies regarding the regularly scheduled medication administration for the patient. The orderlies can be automatically added to the patient's care group by linking the orderlies caregiver profiles to the patient's patient profile.

The user interface 550 includes an example of a scheduled event for the patient at the panel 562. In the example shown, the panel 562 displays a scheduled reminder to administer medication to the patient Brandon LaPlante at 5:30 pm. The user interface 550 can allow the user to scroll through various other reminders and notes associated with the patient. In some implementations, the user interface 550 also shows vital sign information (current vital sign information and/or recorded past vital sign information) and other information for the patient. In some implementations, the user can use the control 520 to transmit a message that includes one or more notes or other information for the patient to one or more caregivers or other recipients. For example, the user can enter a text note to the patient's patient profile indicating that the patient has coughed up blood, and then select the control 520 to send the note to one or more other caregivers to allow the other caregivers to respond to the note. As another example, the user can take a video of patient moving his fingers, post the video to the patient's profile, and then select the control 520 to transmit the video to a physical therapist associated with the patient.

The user interface 550 can include a control 564 to allow the user to designate a note (e.g., a note entered using one of the controls 552, 554, 556, 558, or 560) as a patient note. Designating a note as a patient note can indicate that the note is specific to a particular patient, or includes a patient centric observation. In some implementations, selection of the control 564 causes the user interface 550 to display a list of patients associated with the user of the mobile device 500. The user can then select a patient from the list to associate a note with the selected patient. For example, the note can be posted to the selected patient's patient profile.

The user interface can also include a control 566 to allow the user to designate a note as a staff note. A staff note can be a note that is not associated with any specific patient, but is rather directed toward one or more categories of staff members in general. For example, a note regarding a change in staff scheduling could be designated as a staff note using the control 566. As another example, a change to medication administration procedures could be designated as a staff note. In some implementations, the user can identify a staff note as being applicable to all staff, or to one or more selected categories of staff members. For example, a staff note regarding medication administration could be designated to the attention of all orderlies and nurses. As another example, a staff note regarding a change to operation preparation procedures could be designated to the attention of caregivers involved in operation perpetration.

Notes entered by the user in the form of text notes, images, video notes, audio messages, and calendar events can help improve and coordinate care for the patient. Various notes allow caregivers associated with the patient to coordinate with one another regarding care for the patient even if the caregivers are not physically present at the same location, or are not available at the same times. This can allow issues associated with the patient to be more quickly and efficiently addressed by caregivers who are best suited to address the various issues. This coordinated care can help prevent alarm states for the patient that require immediate attention from occurring by helping to identify and address small problems before they become emergencies. Notes may be entered by caregivers regarding patient status for general posting to the patient newsfeed, which are then viewable by all caregivers associated with the patient. Notes may also be entered by staff or caregivers to facilitate communication between staff or caregivers, and these notes would be more private in nature.

Figure 5E:
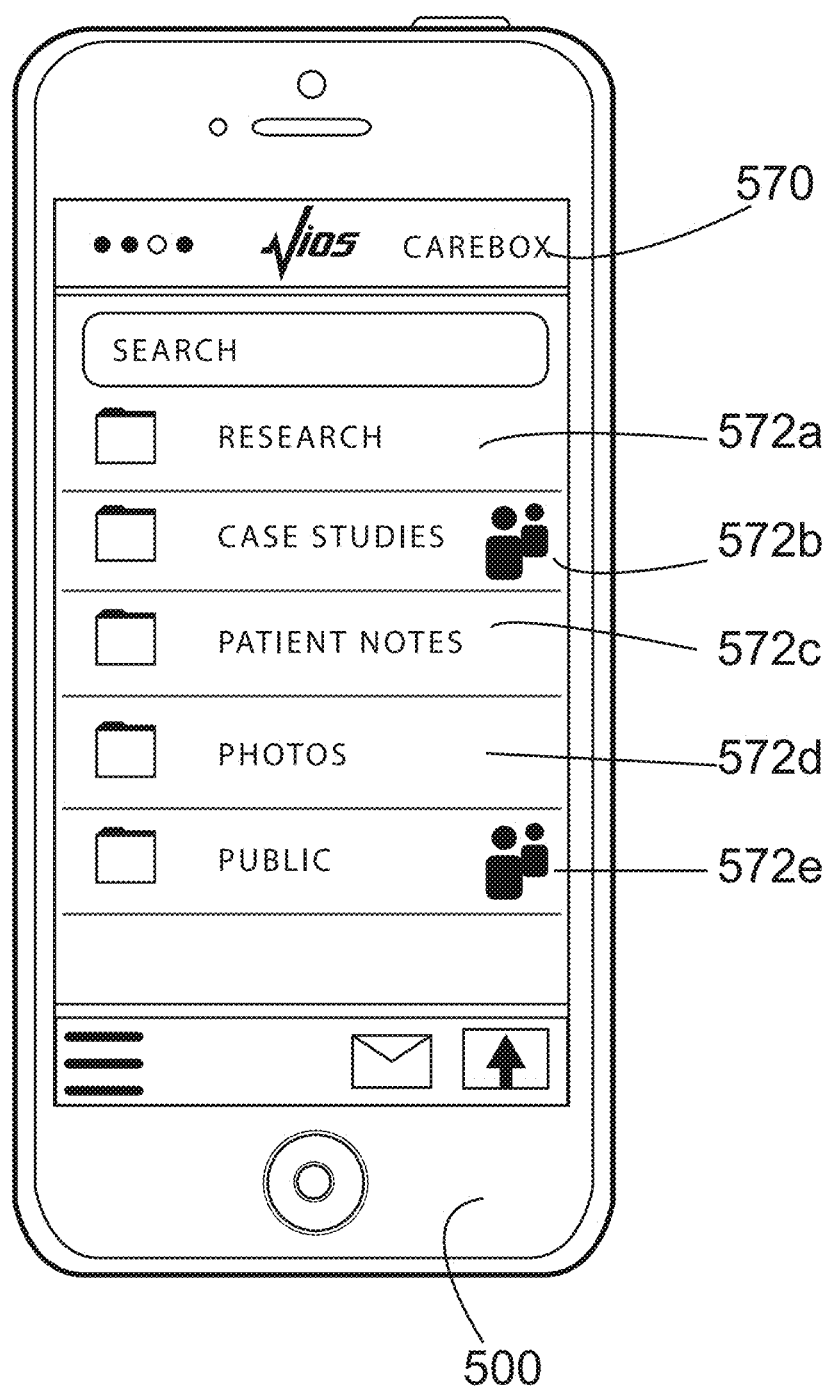

FIG. 5E shows a user interface 570 displayed on the mobile device 500 that includes resources for accessing patient information and other healthcare related information. For example, the user interface 570 includes controls 572*a-e* that allow the user of the mobile device 500 to access information including research information, case studies for various ailments and conditions, patient notes for one or more patients (e.g., patients associated with the user via profile links), photos (e.g., for guidance in visually diagnosing various conditions), and public information. In some implementations, the user interface 570 can be used for general storage and retrieval for various resources that users may use throughout the care process that do not pertain to a particular patient.

Figure 5F:
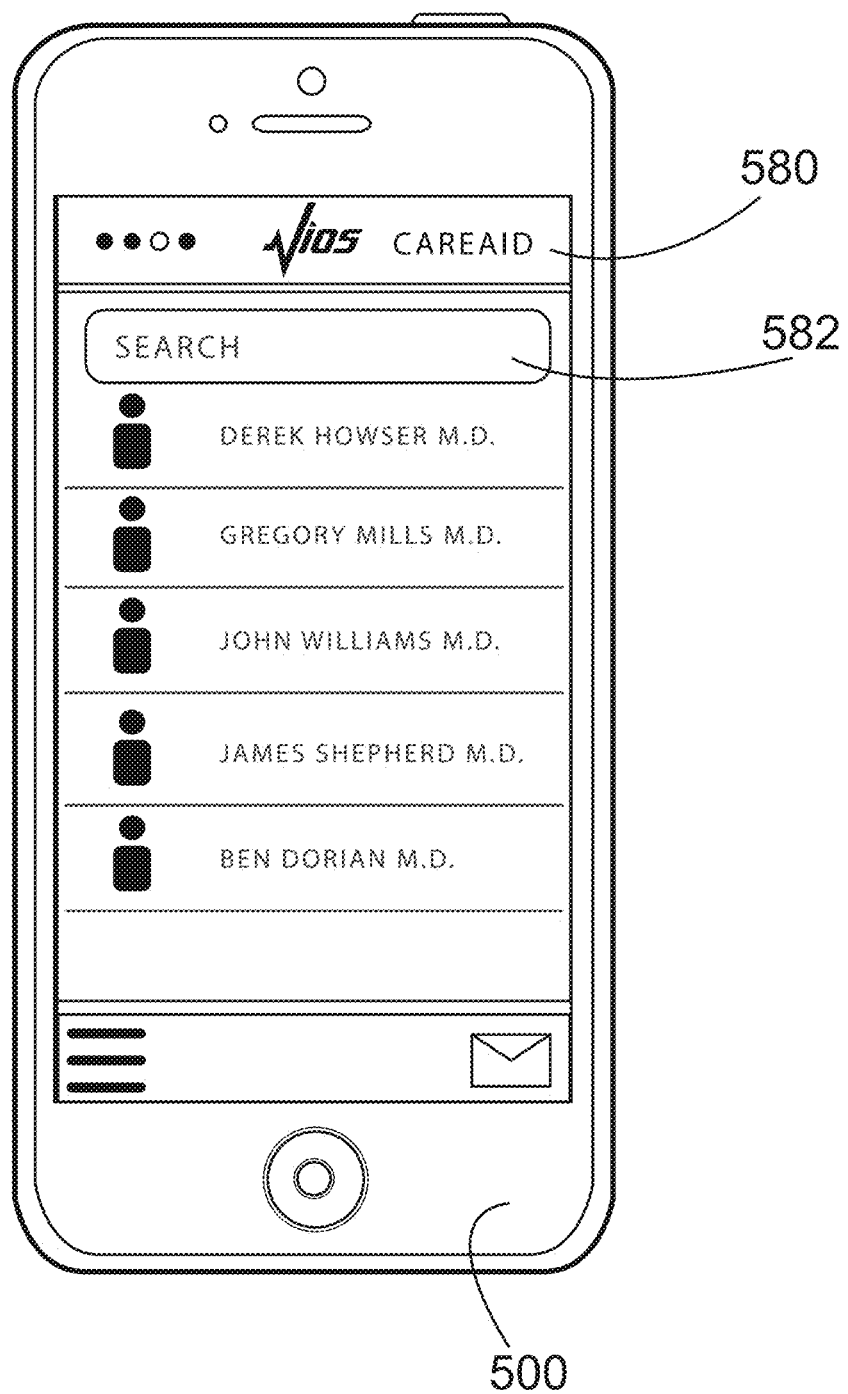

FIG. 5F shows a user interface 580 displayed on the mobile device 500. The user interface 580 allows the user of the mobile device 500 to search for caregivers using a search box 582. The user can search for caregivers by name, specialty, location, patient association, caregiver idea, or other information associated with caregivers. For example, the user can enter a search for cardiologists into the search box 582 to cause the example list of doctors shown in FIG. 5F to be displayed on the user interface 580. As another example, the user can enter a patient's name or patient ID to cause the user interface 580 to display a list of caregivers associated with the patient. For example, caregivers having caregiver profiles that link to the patient's patient profile can be listed on the user interface 580.

In some implementations, the user can use the search box 582 to search for patients, healthcare facilities, or any other healthcare related entities or information. For example, the user can use the search box 582 to search for information on spinal implant procedures. As another example, the user can use the search box 582 to search for cancer treatment facilities within a specified geographic region.

Figure 6A:
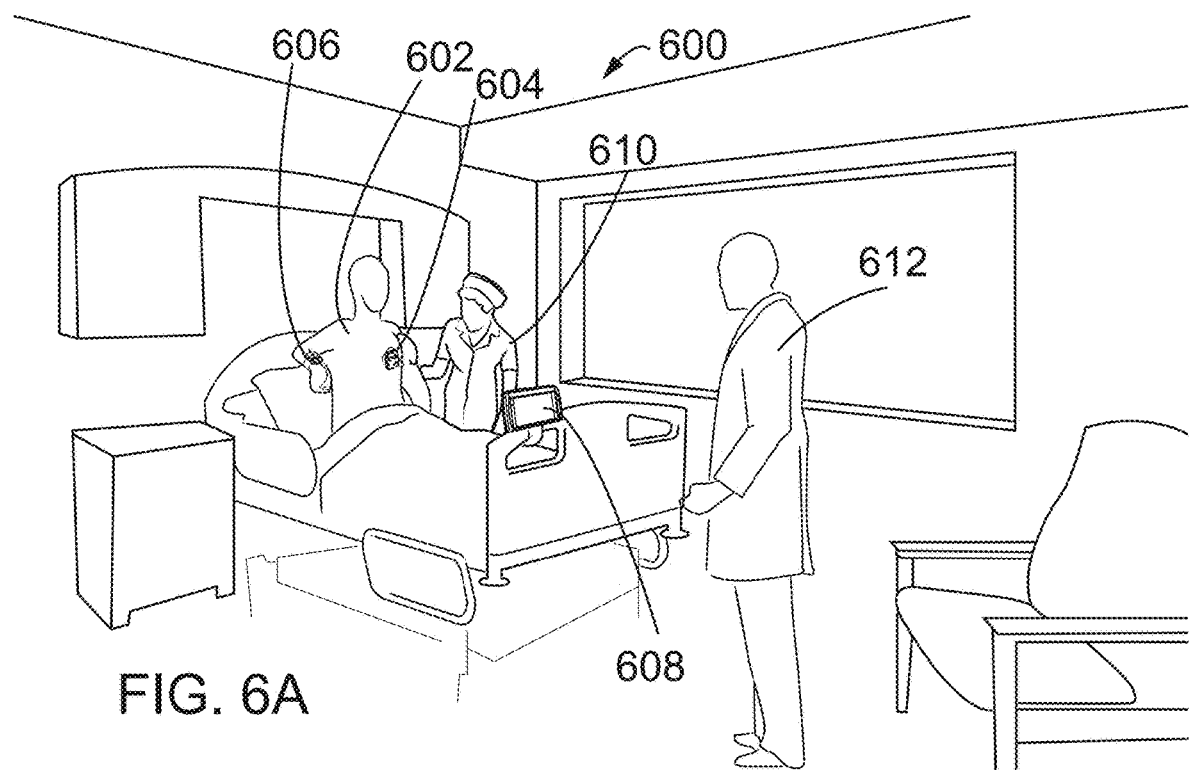
FIGS. 6A-6B show an example system for coordinating patient care and tracking patient movement between healthcare environments.

FIG. 6A shows a patient 602 located in a first healthcare environment 600. For example, the first healthcare environment 600 can be a recovery room that is configured to accommodate patients recovering from emergency surgery. As another example, the first healthcare environment 600 can be a room within a hospital ER that is used to triage incoming patients to identify how to stabilize patients and where to send patients after the ER. The patient 602 is outfitted with a number of patient worn sensors including a chest worn sensor 604 and a wrist sensor 606. The chest worn sensor 604 and wrist sensor 606 can record various vital sign and other information for the patient such as blood pressure, body temperature, respiratory rate, blood oxygenation, heart rhythm (via ECG), heart rate, blood glucose level, and hydration levels as described above. The chest worn sensor 604 and/or wrist sensor 606 can wirelessly communicate with a bedside monitor 608 to allow caregivers to observe vital sign information collected by the chest worn sensor 604 and wrist sensor 606.

In the example shown, the patient 602 is being attended to by caregivers 610 and 612. In addition to the vital sign automatically collected for the patient 602 by the chest worn sensor 604 and wrist sensor 606, the caregivers 610 and 612 can collect additional information for the patient by observing the patient 602 or talking to the patient 602 about the patient 602's symptoms and current condition. The caregivers 610 and 612 can use the bedside monitor 608 or another computing device to enter information about the patient. In some implementations, a patient profile can be created for the patient. Creating a new patient profile for the patient can be as simple as selecting an option to enter a new patient from a menu screen and entering the patient's name. The patient can be automatically assigned a patient ID. The caregiver 610 can then associate the chest worn sensor 604 and wrist sensor 606 with the patient (e.g., by scanning the sensors using a scanner in communication with the bedside monitor 608, or by entering sensor IDs for the sensors into the bedside monitor 608). The caregiver 610 can then attach the chest worn sensor 604 and wrist sensor 606 to the patient to allow the sensors to begin automatically collecting vital sign information for the patient 602 and transmit the information to the bedside monitor 608. The bedside monitor 608 (or another computing device, such as a central server, in communication with the bedside monitor 608) can then record the vital sign information as part of the patient's patient profile. The caregivers 610 and 612 can enter notes (e.g., text notes, images, videos, audio messages, and calendar events) for the patient to aid in diagnosis and patient treatment.

In some implementations, the caregivers 610 and 612 are automatically added to the patient 602's care group. For example, the first healthcare environment 600 can be a room in an ER facility. The caregiver 610 can create a new patient profile for the patient 602 by selecting an "enter new patient" option at the bedside monitor 608 and entering the patient's name and perhaps other identifying information such as a social security number or health insurance ID for the patient. A system that includes the bedside monitor 608 can generate the patient profile and, after the chest worn sensor 604 and wrist sensor 606 have been synced with the bedside monitor 608, begin receiving vital sign information for the patient 602 and associating the vital sign information with the patient profile.

The bedside monitor 608 can be associated with the particular room and bed in which the patient 602 is located and automatically add this room number and bed number information to the patient profile. The system can then identify that the caregiver 610 is a nurse assigned to handle intake and initial triage for patients in the identified room and bed and that the caregiver 612 is a doctor responsible for initial triage and stabilization of patient's in the identified room and bed. The system can automatically add the caregivers 610 and 612 to the patient's care group by linking the caregivers' 610 and 612 caregiver profiles to the patient 602's patient profile. Being added to the patient 602's care group can allow the caregivers 610 and 612 to access information associated with the patient 602 (e.g., by accessing the patient 602's profile). In some implementations, the bedside monitor 608 can require that location information for the patient 602 (room number, bed number, healthcare facility location, etc.) be verified prior to addition of the location information to the patient 602's patient profile. For example, the bedside monitor 608 can display automatically identified location information for the patient 602 and then require that the caregiver 610 or caregiver 612 confirm that the information should be included in the patient 602's patient profile.

Figure 6B:
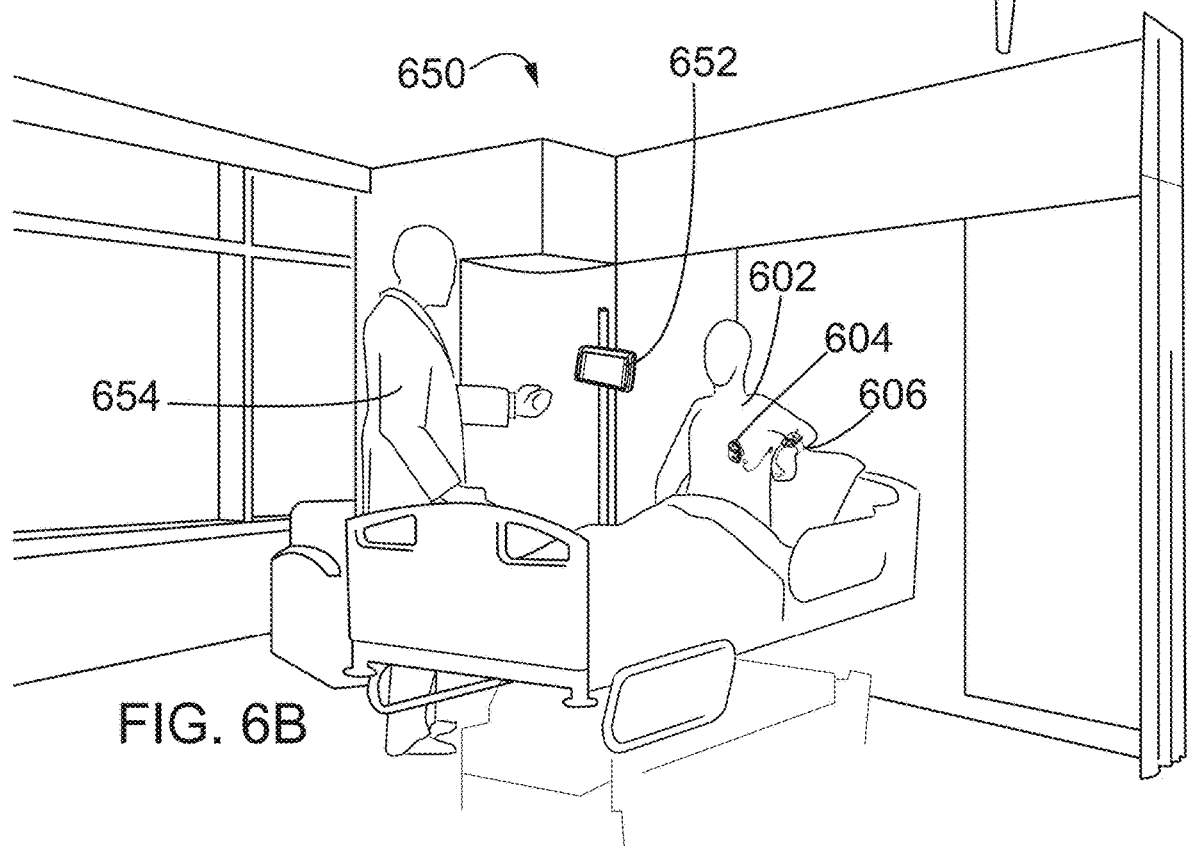

Turning to FIG. 6B, after the patient leaves the first healthcare environment 600, the patient 602 can be transitioned a second healthcare environment 650. For example, if the first healthcare environment 600 is a room within an ER, the patient 602 can be transferred from the first healthcare environment 600 to the second healthcare environment 650 (e.g., a general ward) after the patient 602 has been triaged and the patient 602's initial condition has been stabilized. As another example, if the first healthcare environment 600 is a post-surgery recovery room, the patient 602 can be transitioned to the general ward (second healthcare environment 650) once the patient 602's condition has stabilized or achieved one or more threshold conditions.

As shown in FIG. 6B, the chest worn sensor 604 and wrist sensor 606 can remain associated with the patient 602. The chest worn sensor 604 and/or wrist sensor 606 can sync with a bedside monitor 652 located in the second healthcare environment 650 to transfer vital sign information to the bedside monitor 652. A caregiver 654 located in the second healthcare environment 650 can use the bedside monitor 652 to observe the collected vital sign information and other information for the patient 602 (such as notes entered by the caregiver 610 or the caregiver 612). In some implementations, the chest worn sensor 604 can automatically sync with the bedside monitor 652 upon the chest worn sensor 604 coming within a specified communication range for the bedside monitor 652. In some implementations, the caregiver 654 can sync the chest worn sensor 604 with the bedside monitor 652. Upon syncing with the chest worn sensor 604, the caregiver 654 can automatically access a patient profile for the patient 602 and display information for the patient 602 since the patient 602 (or a patient ID for the patient 602) had previously been associated with the chest worn sensor 604.

The syncing of the chest worn sensor 604 with the bedside monitor 652 can allow the system (which includes the bedside monitor 652) to identify the new location for the patient 602 within the second healthcare environment 650. For example, the bedside monitor 652 can be associated with a specific room and bed number (the bed in which the patient 602 is shown in FIG. 6B). Based on the chest worn sensor 604 syncing with the bedside monitor 652, the system can determine that the patient 602 is now located in the room associated with the bedside monitor 652.

The change in physical location of the patient 602 from the first healthcare environment 600 to the second healthcare environment 650 can, in some implementations, cause the system to automatically take one or more steps with regard to the patient 602 and information associated with the patient 602. For example, the system can determine that the patient 602 has left the ER (the first healthcare environment 600) and is now residing in the general ward (the second healthcare environment 650). The system can automatically change room number and bed number information in the patient 602's patient profile to reflect the new location of the patient 602. Additionally, the system can dynamically update the patient 602's care group by removing the caregivers 610 and 612 (e.g., unlinking caregiver profiles for the caregivers 610 and 612 from the patient 602's patient profile) and by automatically adding the caregiver 654 to the patient 602's care group (e.g., by linking the caregiver 654's caregiver profile to the patient 602's patient profile). The system can automatically identify the caregiver 654 as being associated with the patient based on one or more factors. For example, the system can identify the caregiver 654 as being assigned to monitor the care of all patients located in a specified set of rooms, and that the patient 602 is currently located in one of the rooms for which the caregiver 654 is responsible. As another example, the system can determine that the caregiver 654 is part of the patient 602's care group based on the caregiver 654 using a caregiver ID to log into the bedside monitor 652 and view information for the patient 602 (who is assigned the chest worn sensor 604 that is currently in communication with the bedside monitor 652). In some implementations, additional information associated with the caregiver 654 and/or patient 602 is used to identify that the caregiver 654 should be automatically added to the patient 602's care group.

In some implementations, location for the patient 602 can be determined using methods other than by identifying an assigned location for a bedside monitor or other device that is currently synced with one or more patient worn monitors being worn by the patient 602. For example, the chest worn sensor 604 can include a GPS unit or a location determination module that determines location using other techniques, such as RF signal triangulation. Location information for the patient 602 that is derived using a GPS unit or other location determination module can be used to identify a hospital environment for the patient or a transition from one hospital environment to another for the patient (e.g., transition from the first healthcare environment 600 to the second healthcare environment 650) to automatically update information for the patient, including care group information.

In some implementations, the system does not determine that the patient 602 has transitioned from one healthcare environment to another until a specified period of time has elapsed. For example, the system can identify that the patient 602 is located in the second healthcare environment 650 by identifying that the chest worn sensor 604 has synced with the bedside monitor 652, but can delay permanently associating the patient 602's patient profile with the second healthcare environment 650 (and with caregivers associated with the second healthcare environment 650, such as the caregiver 654) until a specified time period has elapsed. For example, the system can delay associating the patient 602 with the second healthcare environment 650 until the patient 602 is determined to have been located in the second healthcare environment 650 for longer than three hours. Putting temporal constraints on this automatic updating of patient profile information can prevent the patient 602's patient profile from being erroneously updated if the patient 602 is quickly transitioning between several healthcare environments, or if the patient 602 is only briefly staying at the second healthcare environment 650 before returning to the first healthcare environment 600. For example, the second healthcare environment 650 could be an office for a nutrition coach and the patient 602 may only be located there for an hour long consultation before returning to the patient 602's permanently assigned location of the first healthcare environment 600.

In some implementations, rather than being assigned to particular locations, rooms or beds, bedside monitors can be mobile and travel with the patient. For example, the bedside monitor 608 and bedside monitor 652 can be the same bedside monitor in this example rather than different bedside monitors as discussed in the previous examples. The bedside monitor 608/652 can be transferred from the first healthcare environment 600 to the second healthcare environment 650 along with the patient 602. In some implementations, the new location for the bedside monitor 608/652 can be manually input. For example, the caregiver 654 can enter the room number and bed number for the patient 602 in the second healthcare environment 650 and associate the new room number and bed number with the patient 602's patient profile. In some implementations, the new location for the bedside monitor 608/652 can be determined using a location determination unit of the bedside monitor 608/652 or the chest worn sensor 604. For example, a GPS unit included in the chest worn sensor 604 can be used to identify the new location for the patient 602 in the second healthcare environment 650 and the patient 602's patient profile can automatically be updated with the new location information.

In some implementations, prior to the transition for the patient 602 from the first healthcare environment 600 to the second healthcare environment 650, a caregiver can enter information associated with the transition into the system. For example, the caregiver 610 can access a patient profile for the patient 602 using the bedside monitor 608 and indicate that the patient 602 is scheduled to transition to the second healthcare environment 650 at a specified time or on a specified date. For example, the second healthcare environment 650 can be an area designated for surgery preparation. The caregiver 610 can indicate that the patient 602 is to be transitioned to the second healthcare environment 650 two hour prior to a scheduled surgery for the patient 602 to be prepped for the surgery. The system can then automatically add caregivers associated with the second healthcare environment 650 to the patient 602's care group prior to the patient 602 physically transitioning to the second healthcare environment 650. For example, an anesthesiologist scheduled to work in the second healthcare environment 650 during a specified time frame can be automatically added to the patient 602's care group (e.g., by the patient 602 and anesthesiologist's profiles being linked to each other by the system) prior to the patient 602 transitioning to the second healthcare environment 650. This can allow the anesthesiologist to view healthcare information for the patient 602 (for example, such as medication allergies of the patient 602) to properly prepare to anesthetize the patient 602.

In some implementations, caregivers can be automatically added to the patient 602's based on proximity of the caregivers and the patient 602. For example, the caregiver 654 can carry a mobile device. The mobile device can connect to the system (e.g., through a wireless communication protocol such as WiFi) and identify the location of the caregiver 654 to the system as the caregiver 654 moves about a healthcare facility that includes the second healthcare environment 650. In this example, the caregiver 654 may be the only attending physician currently located at the second healthcare environment 650. The system can therefore automatically add the caregiver 654 to the patient 602's care group based on the physical presence of the caregiver 654 in the second healthcare environment 650. As another example, the system can automatically detect that the caregiver 654 and the patient 602 have been within a specified proximity of each other for a specified time duration. The system can use this information to determine that the caregiver 654 is providing care to the patient 602 and automatically add the caregiver 654 to the patient 602's care group.

In some implementations, the system can automatically remove the caregiver 654 from the patient 602's care group (e.g., by removing a link to the caregiver 654's caregiver profile from the patient 602's patient profile). For example, the system can determine that the patient 602 has left the second healthcare environment 650 and has been away from the second healthcare environment 650 for a specified time duration. The system can then identify that the caregiver 654 (who is associated with the second healthcare environment 650) is no longer responsible for care for the patient 602 and remove the caregiver 654 from the patient 602's care group. As another example, the system can determine that the caregiver 654 has not been within a specified proximity of the patient 602 for a specified time period (e.g., 7 days) and therefore determine that the caregiver 654 is no longer associated with the patient 602 and remove the caregiver 654 from the patient 602's care group.

Figure 7:
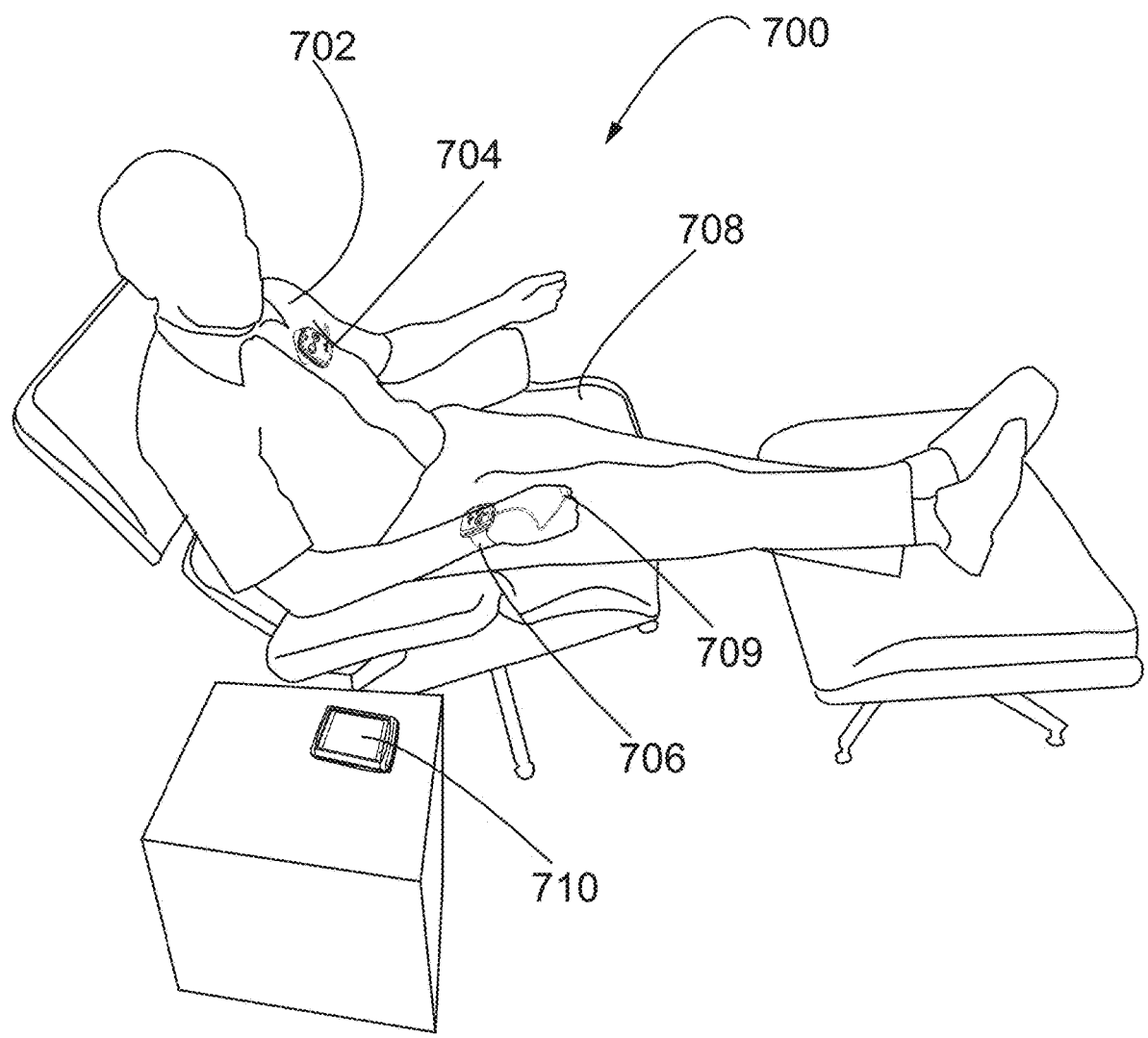
FIG. 7 shows a patient worn sensor utilized in a home environment and an example graphical user interface for providing healthcare information to a patient.

FIG. 7 shows a patient 702 located in a home environment 700. The patient 702 is outfitted with a chest worn sensor 704. Although the chest worn sensor 704 is depicted as being outside of the patient 702's shirt for purposes of illustrating details of the chest worn sensor 704 in the present example, in practice the chest worn sensor 704 would be adhered to the skin of the patient 702 near the patient 702's heart and positioned, for example, so as to pick up 6-lead ECG readings for the patient 702. The chest worn sensor 704 can measure patient vital signs such as respiratory rate, blood oxygenation, heart rhythm (via ECG), heart rate, and patient orientation (for detecting falls or lack of movement). The chest worn sensor 704 can include a temperature sensor component (not shown) positioned under the patient 702's armpit (under the patient 702's shirt so as to contact the patient 702's skin) for measuring body temperature for the patient 702. The patient 702 is additionally outfitted with a wrist sensor 706 and a really comfy chair 708. The wrist sensor 706 can be configured to track patient vital signs such as blood pressure. The wrist sensor 706 can include a finger sensor 709 for engaging one or more fingers of the patient 702 and tracking blood oxygenation (SpO2) for the patient 702 or, in some cases, blood pressure for the patient 702. In some implementations, rather than being located at the wrist of the patient 702, the wrist sensor 706 can take the form of an upper arm sensor that is located at the upper arm (above the elbow) of the patient 702. The upper arm sensor can be used, for example, to measure blood pressure for the patient 702.

The chest worn sensor 704 and wrist sensor 706 can sync with a computing device 710 and wirelessly transmit vital sign information to the computing device 710. The computing device 710 can be, for example, the patient 702's personal mobile phone, a tablet device, a personal computer, or a specialized monitoring device provided by a healthcare provider associated with the patient 702. The patient 702 can use the computing device 710 to view vital sign information collected and transmitted by the chest worn sensor 704 and wrist sensor 706. Additionally, the computing device 710 can communicate to one or more servers of a healthcare system through a network connection (e.g., a WiFi connection in the patient 702's home connecting to an internet connection, or through a cellular connection) and transmit information collected by the computing device 710 to the central server. The collected information can then be associated with the patient 702 at the central server. For example, the information can be added to a patient profile for the patient 702. The computing device 710 can generally allow the patient 702 to view information as if the patient 702 were located within a healthcare facility. Additionally, transmission of vital sign information by the computing device 710 to remote servers of the healthcare system can allow caregivers (e.g., caregivers in the patient 702's caregroup) to monitor the patient 702's progress without having to be physically present in the same location as the patient 702. This functionality can facilitate discharge of the patient 702 from a healthcare facility on a quicker time frame than if remote monitoring of the patient 702 were not available.

The patient 702 can also use the computing device 710 to access other healthcare related information. For example, the patient 702 can use the computing device 710 to access his patient profile and, in some cases, edit information included within his patient profile. The patient 702 can use the computing device 710 to add notes (e.g., text notes, images, videos, audio messages, or calendar events as described above) to his patient profile. This patient provided information can supplement the information recorded by the chest worn sensor 704 and wrist sensor 706 to allow caregivers to better monitor the patient 702's current status and recovery progress, or to identify other potential health issues for the patient 702. For example, the patient 702 can supplement his patient profile by adding a text note indicating that he has experienced a loss of appetite. As another example, the patient 702 can add a video of himself walking to his patient profile to allow a caregiver to better assess the patient 702's progress with improving motor functions. As yet another example, the patient 702 can make an entry to his patient profile every time he takes a prescribed medication. Such updated patient profile information for the patient can be stored by the remote servers.

The computing device 710 can also provide healthcare related alerts and notices to the patient. For example, the patient's profile can include a regularly scheduled event indicating that the patient 702 needs to take medication every day at 3:00 pm. The computing device 710 can remind the patient 702 to take his medication at the designated time every day (e.g., through the use of visual or audible alerts). The patient 702 can also use the computing device 710 to reach out to caregivers to receive advice and guidance as to how to address problems, or to diagnose various occurrences. For example, the patient 702 can access a caregiver profile for a nutrition coach that is part of the patient 702's care group and post a question to the caregiver profile asking about whether or not a particular food is safe to eat given the patient 702's current health state. The nutrition coach can respond to the patient 702's inquiry by posting a note to the patient 702's patient profile. The computing device 710 can indicate that the note has been posted by issuing an alert to the patient 702. The patient 702 can then review the response from the nutrition coach using the computing device 710.

In practice, the computing device 710 can perform many, if not all, of the same functions as the bedside monitor 108 described above with respect to FIG. 1. Additionally, the computing device 710 can provide various user interface screens to the patient 702. The user interfaces provided by the computing device 710 can include user interfaces similar to those discussed with respect to FIGS. 3A-3D and 5A-5F.

In practice, the patient 702 enters the home environment 700 after being discharged from a hospital or other healthcare facility. For example, a healthcare system (such as the system 100 of FIG. 1) can identify information entered by a doctor indicating that the patient 702 is to be discharged from the hospital. The healthcare system can perform a check of the patient 702's vital signs or other information for the patient 702 to verify that the patient 702 is in sufficient condition to be discharged. If the healthcare system determines (e.g., based on vital sign information of the patient 702) that the patient 702 may not be in a stable enough condition to be discharged, the heathcare system can alert one or more caregivers that the entered indication that the patient 702 is to be discharged may have been a mistake.

Assuming that the instructions to discharge the patient 702 were not a mistake and that the patient 702's vital signs are within acceptable ranges, the patient 702 is discharged from the hospital. At the time of discharge, the patient 702 may leave with the chest worn sensor 704 to allow vital signs and other information related to the patient 702 to be tracked. In some cases, the chest worn sensor 704 is the same as a chest worn sensor that is affixed to the patient 702 while the patient 702 was residing at the hospital. In some implementations, the chest worn sensor affixed to the patient as the hospital is removed and replaced by the chest worn sensor 704. For example, chest worn sensors intended for in-hospital use may have a different set of functionality than chest worn sensors intended for in-home use.

After discharge, the patient 702 goes home and the patient's vital signs continue to be monitored by the chest worn sensor 704 as described above. The patient 702 can additionally enter additional information related to the patient 702's recovery progress or health state using the computing device 710. In some implementations, the healthcare system can automatically add and/or remove caregivers to/from the patient 702's care group upon discharge of the patient 702 from the hospital. For example, one or more attending nurses employed at the hospital can be automatically removed from the patient 702's care group upon discharge of the patient 702 from the hospital. Following this example, a doctor in charge of observing the patient 702 while the patient 702 was at the hospital (e.g., while the patient 702 was recovering from surgery) is not automatically removed from the care group at the time that the patient 702, but rather can be automatically removed a set period of time (e.g., two weeks) after the patient 702 is discharged as long as the patient 702's recovery is proceeding normally.

Other caregivers can also be automatically added to the patient 702's care group upon discharge of the patient 702 from the hospital. For example, a home care observation nurse and/or one or more additional home care associated caregivers can be automatically added to the patient 702's care group by the hospital system when the patient 702 is discharged. For example, a home care worker can be automatically selected to be included in the patient 702's care group. The home care worker can be scheduled to make periodic home visits to the home environment 700 to check on the recovery of the patient 702 in person. As another example, a remote caregiver at a location that is geographically distant from both the hospital and the home environment 700 can be automatically added to the patient 702's care group to remotely monitor the patient 702's status. The remote caregiver can receive alerts related to the patient 702's status and other information for the patient 702 related to the patient's care. The remote caregiver can make healthcare decisions for the patient 702 based on the received information. As another example, a specialist who specializes in treating diabetes can be automatically added to the patient 702's care group when the patient 702 is discharged.

The specialist can remotely monitor the patient 702's status, for example, by receiving alerts related to the patient 702, by periodically checking the patient's patient profile, and by receiving updates on the patient 702's status as part of a newsfeed interface of a caregiving network. The specialist can provide guidance and treatment recommendations to the patient 702. The specialist can also communicate with the patient 702 (e.g., using the caregiving network) to address concerns of the patient 702 and advise the patient 702 on how to treat his diabetes or deal with side effects caused by the patient 702's diabetes treatment.

Figure 8:
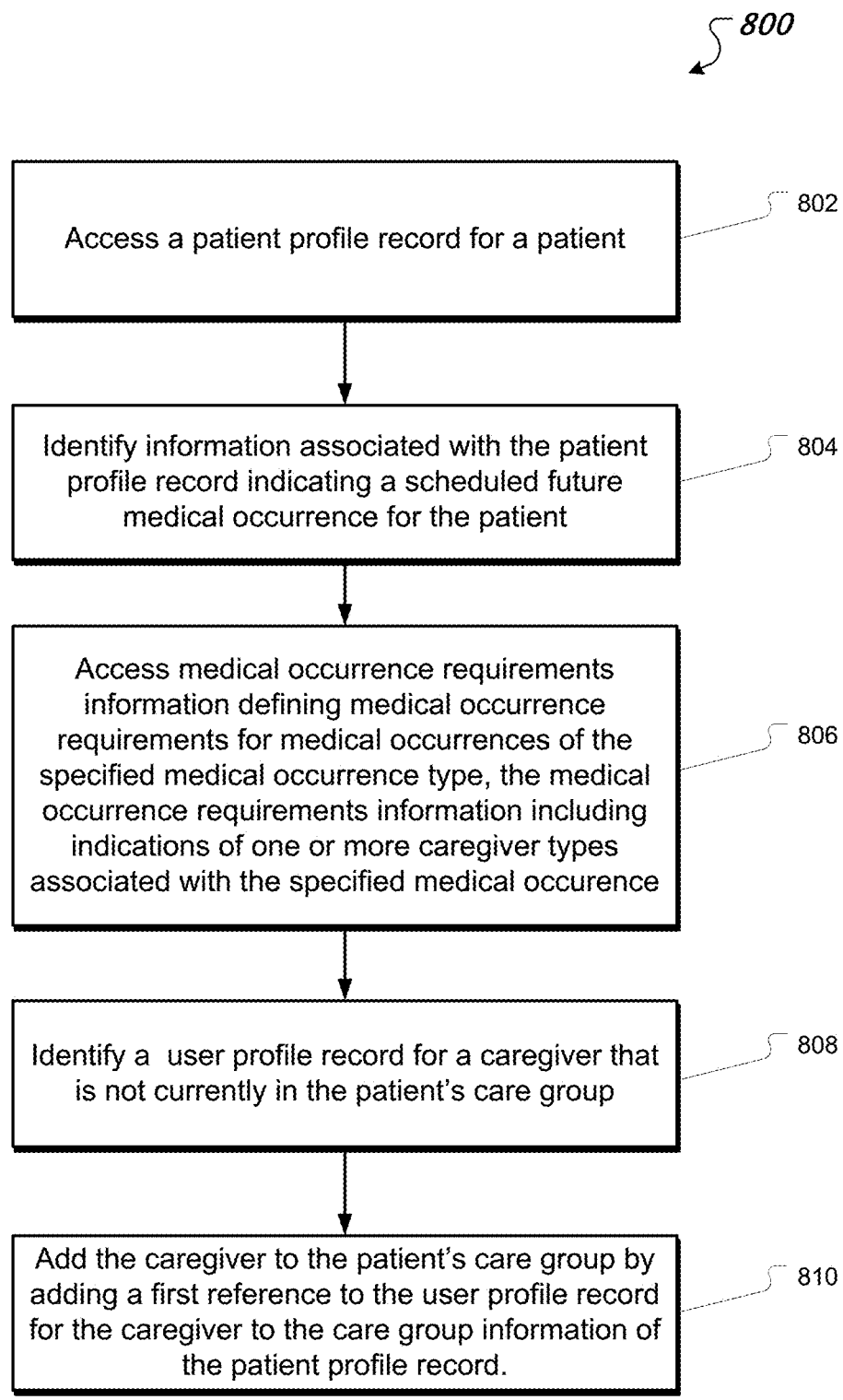
FIG. 8 is a flow chart of an example process for dynamically updating a care group for a patient.

FIG. 8 shows a flow chart for a process 800 that includes accessing a patient profile record for a patient (802). For example, a computer system, such as the central server 103 shown in FIG. 1, can access an electronic storage medium that stores one or more patient profile records. The system can identify a patient profile for the patient by, for example, searching the store of patient profiles using the patient's name or a patient ID for the patient. Each patient profile in the store can include information for a respective patient. Information included in each patient profile can include a patient identifier, patient name, vital sign information received from a patient worn sensor associated with the patient, care information derived from user input received from a first caregiver, and care group information for the patient. The vital sign information can, for example, include: blood pressure, body temperature, respiratory rate, patient orientation, blood oxygenation, heart rhythm (via ECG), and heart rate. The vital sign information can be collected in real time or near real time from a patient worn sensor worn by the patient associated with the patient profile. Care information can included notes and other information entered by caregivers. For example, caregivers can enter notes on patient recovery progress, therapy, treatment, or care. For example, a caregiver can enter in notes regarding medication administration for the patient. As another example, a caregiver can enter information about symptoms described by the patient. In some implementations, care information can include an indication of a medical occurrence associated with the patient. For example, the care information can indicate that the patient was in a car accident. As another example, the care information can indicate that the patient experienced a heart attack and include a date and approximate time that the heart attack occurred. As yet another example, the care information can indicate that the patient experienced a seizure along with a date and approximate time that the seizure occurred.

The care group information for the patient can be included in the patient's profile in the form of a list of names of caregivers responsible for providing or supervising care of the patient, a list of caregiver IDs for caregivers responsible for providing or supervising care of the patient, or links to caregiver profiles for caregivers responsible for providing or supervising care of the patient. In some implementations, caregiver profiles for caregivers in the patient's care group can be accessed by selecting links include in the patient's patient profile.

The process 800 further includes identifying information associated with the patient profile record indicating a scheduled future medical occurrence for the patient (804). For example, the system can identify that the patient is scheduled to undergo a skin graft procedure. As another example, the system can identify that the patient is scheduled to participate in a physical therapy session at a particular date at time. In some implementations, identifying the information indicating the scheduled future medical occurrence includes identifying a specified medical occurrence type for the scheduled future medical occurrence. Examples of medical occurrence type can include specific surgery types (heart surgery, brain surgery, spine surgery, hand surgery, etc.), various physical therapy activities or sessions, administration of medication, a check-up, or any other future scheduled care activity. For example, the specified medical occurrence can have a medical occurrence type of "walk" to indicate that the patient is scheduled to go for a walk at a specific time. As another example, the specified medical occurrence can have a type of "medication administration" to indicate that medication is to be administered to the patient at a specified time.

In some implementations of the process 800, the system can dynamically predict the future medical occurrence for the patient based on the vital sign information and the care information included in the patient profile record for the patient. For example, the care information can include a note entered by an ER nurse indicating that the patient was in a car accident and suffered a broken bone. Vital sign information collected from patient worn sensors issued to the patient in the ER can indicate that the patient is currently in a stable condition sufficient for entering surgery. The system can then automatically schedule an operation to set the patient's broken leg by locating and reserving a room that is suitable for the procedure. In some implementations, the system can also dynamically identify one or more doctors to perform the procedure and other caregivers necessary for the procedure (such as a surgical pharmacist or an anesthesiologist), identify that the doctors and caregivers are available to participate in the procedure, and schedule them to participate in the procedure.

As another example, care information can indicate that the patient has undergone hand surgery. The system can use this information to determine that the patient needs to undergo rehabilitative physical therapy for the hand. The system can further access vital sign information for the patient to identify that the patient has sufficiently recovered from the surgery to be able to safely begin rehabilitative physical surgery. The system can then identify an appropriate physical therapist to administer the physical therapy, and schedule a rehabilitative physical therapy session for the patient with the physical therapist during a free time period in the physical therapists schedule.

In some implementations, predicting a future medical occurrence for the patient can include accessing a plurality of medical occurrence indicators at a stored location, with each medical occurrence indicator being associated with a theoretical medical occurrence. Each possible medical occurrence indicator can further include precursor information indicating one or more prior vital sign states or one or more prior medical occurrences that indicate a possible need for the theoretical medical occurrence associated with the particular medical occurrence indicator. The system can then identify one or more potential future medical occurrences for the patient by comparing the vital sign information and the care information obtained from the patient's patient profile record to the precursor information associated with each of the plurality of medical occurrence indicators.

For example, precursor information for a medical occurrence indicator indicating that a patient requires a leg to be set can include requirements that care information for the patient indicates that the patient's leg is broken and that vital sign information (e.g., as collected in real-time or near real-time) indicates that the patient is in a stable condition and therefore physically ready to undergo surgery. As another example, precursor information for a medical occurrence indicator indicating that a patient requires heart bypass surgery can include a specified required combination of heart rate information, ECG information, and patient or caregiver reported symptoms indicating that the patient requires heart bypass surgery. As yet another example, precursor information for a medical occurrence indicator indicating that a patient is to be administered medication can require that the patient has been prescribed the medication, that the patient has not already received the medication during a specified time period, and that the patient is currently awake.

The process 800 includes accessing medical occurrence requirements information defining medical occurrence requirements for medical occurrences of the specified medical occurrence type (806). The medical occurrence requirements information can include indications of one or more caregiver types associated with the specified medical occurrence. For example, if the medical occurrence type is "hand surgery" the medical occurrence requirements can indicate that caregivers of type "hand surgeon," "surgery attendant nurse," and "anesthesiologist" are associated with the medical occurrence type. As another example, if the medical occurrence type is "walk" the medical occurrence requirements can indicate that caregiver type "orderly" is associated with the medical occurrence type. As yet another example, if the medical occurrence type is "check-up" the medical occurrence requirements can indicate that caregivers of types "registered nurse" or "physician's assistant" are associated with the medical occurrence type.

The process 800 identifies a user profile record for a caregiver that is not currently in the patient's care group (808). In identification of the caregiver can include matching a particular caregiver type that is associated with the medical occurrence type to information included in the user profile record indicating that caregiver is a caregiver of the particular caregiver type and then matching medical occurrence timing criteria associated with the scheduled future medical occurrence to schedule information included in the user profile record for the caregiver indicating that the caregiver is scheduled to work and is available during a time frame indicated by the timing criteria. For example, the medical occurrence requirements information for the future scheduled medical occurrence can indicate that a caregiver of type "heart surgeon" is needed for the future scheduled medical occurrence. The system can access caregiver profiles for a number of caregivers, identify which caregiver profiles are associated with heart surgeons, and then identify one or more heart surgeons that are available to perform operation at the time that the heart operation is scheduled. As another example, the future scheduled medical occurrence can have a medical occurrence type of "turn patient" and requirements information for the medical occurrence type can indicate that a caregiver of type "orderly" is required to perform the turn patient procedure. The system can access caregiver profiles and identify a caregiver profile for a caregiver who is an orderly, is scheduled to work when the turn patient procedure is scheduled, and is not already busy at that time.

The process 800 includes adding the identified caregiver to the patient's care group by adding a first reference to the user profile record (i.e. caregiver profile) for the caregiver to the care group information of the patient profile record for the patient (810). In some implementations, a reference to the patient profile record for the patient can also be added to the identified caregiver's caregiver profile. Adding the identified caregiver to the patient's care group can allow the caregiver to access the patient's patient profile, review some or all of the information included in the patient profile, and receive alerts regarding patient events such as patient alarm states. Additionally, when the caregiver is added to the patient's care group, a customized patient newsfeed for the caregiver can include information for the patient.

Figure 9:
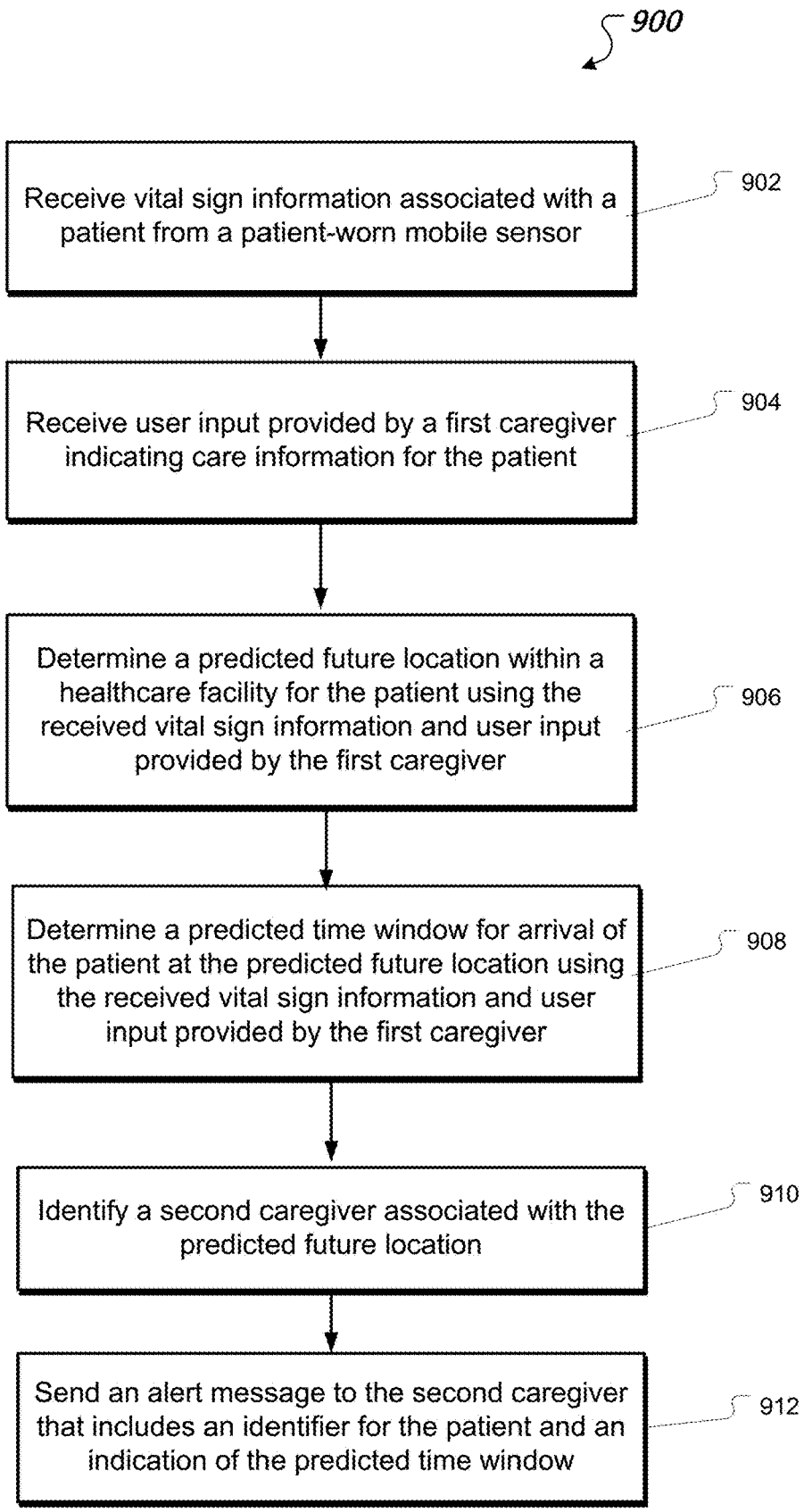
FIG. 9 is a flow chart of an example process for predicting a future location for a patient and issuing an alert to a caregiver associated with the predicted future location.

FIG. 9 shows a flow chart for a process 900 that includes receiving vital sign information associated with a patient from a patient-worn mobile sensor (902). For example, vital sign information can be received from a chest worn sensor such as the chest sensor 102 of FIG. 1 or a wrist worn sensor such as the wrist sensor 106 of FIG. 1. Vital sign information received from the patient-worn mobile sensor can include blood pressure, body temperature, respiratory rate, patient orientation, blood oxygenation, heart rhythm (via ECG), and/or heart rate. The vital sign information can be received by, for example, a bedside monitor, such as the bedside monitor 108 of FIG. 1, or a central server, such as the central server 113 of FIG. 1. As another example, the vital sign information can be received by a computing device such as the computing device 710 of FIG. 7 or the mobile device 500 of FIG. 5A.

The process 900 further includes receiving user input provided by a first caregiver indicating care information for the patient (904). For example, the caregiver can enter notes for the patient using a bedside monitor, mobile device, or other computing device. The notes can include text notes, images, videos, audio messages, or calendar events. The notes can describe symptoms for the patient, treatment administered for the patient, diagnosis suggestions, future recommended treatment for the patient, medication recommendations for the patient, past medical occurrences for the patient, or other care related information associated with the patient. The notes can additionally include snapshots of patient vital signs such as, for example, heart rhythm waveforms or blood oxygenation level readings. In some implementations, the caregiver can make annotations to patient vital sing snapshots or to other images. For example, the caregiver can take a picture of a surgical incision on the patient; make an annotation that abnormal swelling for the incision has been observed; and asking another caregiver for input on the situation. The information can be routed through a network to a central server or other computing device. For example, the central server 113 of FIG. 1 can receive user input indicating care information for the patient from the bedside monitor 108 through the network 112.

The process 900 includes determining a predicted future location within a healthcare facility for the patient using the received vital sign information and user input provided by the first caregiver (906). For example, the system can identify that the patient is experiencing heart failure based on collected vital sign information and care information, and predict that the patient needs to be sent to an operating room for emergency surgery. The system can additionally predict that the patient will be transferred to a recovery room after the surgery, and then to an intensive care unit.

As another example, the care information can include a note entered by an ER nurse indicating that the patient was in a car accident and suffered a broken bone. Vital sign information collected from patient worn sensors issued to the patient in the ER can indicate that the patient is currently in a stable condition sufficient for entering surgery. The system can then predict a future location for the patient as being a surgery room that is properly equipped for a bone setting procedure that is not already scheduled for another procedure in the near future. In some implementations, the system can also dynamically identify one or more doctors to perform the procedure and other caregivers necessary for the procedure (such as a surgical pharmacist or an anesthesiologist), identify that the doctors and caregivers are available to participate in the procedure, and schedule them to participate in the procedure.

As another example, the care information can indicate that the patient has undergone hand surgery. The system can use this information to determine that the patient needs to undergo rehabilitative physical therapy for the hand. The system can further access vital sign information for the patient to identify that the patient has sufficiently recovered from the surgery to be able to safely begin rehabilitative physical surgery. The system can use this information to identify a physical therapy room as the predicted future location for the patient. The system can then identify an appropriate physical therapist to administer the physical therapy, and schedule a rehabilitative physical therapy session for the patient with the physical therapist during a free time period in the physical therapists schedule.

As yet another example, the care information can indicate that the patient has experienced a stroke and is exhibiting slurred speech. The system can use this information to predict a speech therapy center as the predicted future location for the patient.

In some alternative implementations of the process 900, the process 900 can include determining a predicted future location for the patient that is a location other than a location within a particular healthcare facility. The predicted future location for the patient can be predicted using the received vital sign information and user input provided by the first caregiver. Other information for the patient can also be used to determine the predicted future location, such as information stored in a patient profile for the patient.

For example, the system can identify that the patient has undergone knee surgery and as a result was required to undergo a set number of physical therapy sessions prior to being discharged from the hospital and a number of additional physical therapy sessions after having been discharged from the hospital. The system can identify that the patient's knee surgery has already occurred and that the surgery was successful (e.g., no major complications experienced during the surgery). The system can additionally identify that the patient is required to engage in three rehabilitation sessions prior to discharge and that the patient cannot be discharged until at least 72 hours after completion of the surgery. The system can then identify that the patient has participated in the required three rehabilitation sessions and that more than 72 hours have elapsed since the completion of the patient's knee surgery. Based on this information, the system can predict a future location of "home" for the patient and estimate a discharge time, or discharge time frame for the patient. In some implementations, the system also accesses real-time vital sign information for the patient to identify that the patient's vital signs are currently within a "normal" or "acceptable" range prior to predicting a discharge time and a predicted future location of "home" for the patient.

As an alternative example, the system can determine that the patient has only attended two of three required physical therapy sessions and that only 68 hours have elapsed since the completion of the patient's knee surgery. The system can use this information to determine that the patient is not yet ready for discharge from the hospital, but that the patient will be discharged during a time window a set amount of time after the patient attends a third physical therapy session. The system can identify that the patient is scheduled to attend a third physical therapy session at a particular time that is more than 72 hours after completion of the surgery. The third physical therapy session can be, for example, previously have been automatically scheduled by the system (as described above) or manually scheduled by a caregiver and/or the patient. The system can predict a discharge time window for the hospital as occurring a predetermined amount of time after the patient's third physical therapy session. The system can additionally determine a predicted future location of "home" for the patient.

Continuing with the above example, the system can also identify that the patient is required to participate in a set number (e.g., five) of physical therapy sessions after the patient has been discharged from the hospital. The physical therapy sessions may be conducted at the hospital, or possibly at another outpatient facility having specialized equipment for performing such physical therapy appointments. The system can use collected information (e.g., information entered by the first caregiver, vital sign information, and patient information stored as part of the patient's patient profile) to predicted a future location for the patient as being a particular rehabilitation facility located outside of the hospital. In some implementations, the system can automatically schedule one or rehabilitation sessions for the patient based on the predicted future location of the rehabilitation facility. In some implementations, the system can also dynamically identify one or more physical therapists and/or other caregivers necessary for the procedure, identify that the identified physical therapists are available to participate in the rehabilitation session, and schedule them to participate in the rehabilitation session.

As yet another example, the system can identify that a patient is currently located in a general hospital ward while the patient recovers from a recent heart surgery. The system can monitor information entered by one or more caregivers for the patient as well as vital sign information for the patient to predict a time window in which the patient will be discharged from the hospital. The system can further determine that the patient requires assisted living care after discharge from the hospital, and determine a predicted location of a particular assisted living care facility for the patient after discharge.

The process 900 includes determining a predicted time window for arrival of the patient at the predicted future location using the received vital sign information and user input provided by the first caregiver (908). For example, in a situation in which the patient is currently in the ER and needs to be rushed into surgery, the predicted time window for arrival of the patient in surgery can be in the next five to fifteen minutes. The system can then predict that the patient will arrive at a recovery room in two to two and a half hours, and that the patient will arrive in an intensive care unit in six to eight hours.

As another example, if the predicted future location for the patient is a physical therapy area, the predicted time window for arrival of the patient can be at a time when the physical therapist has an available time slot. As another example, if the predicted future location is a surgery room for a future planned surgery, the predicted time window for arrival of the patient can be a time when the surgery room is available and when doctors and other caregivers for performing the operation are available to perform the operation.

The process 900 includes identifying a second caregiver associated with the predicted future location (910). For example, a physical therapist can be associated with a predicted future location of a physical therapy center. As another example, one or more heart surgeons, nurses, pharmacists, physician's assistants, and anesthesiologists can be associated with a cardiac surgery facility. As another example, a number of nurses and other caregivers can be associated with a general ward while a second set of nurses and caregivers is associated with an intensive care unit. In some implementations, these associations can be automatically identified by accessing caregiver profiles for the caregivers that indicate associated locations for the caregivers. In some implementations, each location, department, wing, etc. within a healthcare facility can be associated with a specified list of one or more caregivers.

The process 900 includes sending an alert message to the second caregiver that includes an identifier for the patient and an indication of the predicted time window (912). For example, the predicted future location for the patient can be an intensive care unit. The system can identify a nurse who is associated with the intensive care unit and is scheduled as a supervising nurse during a time frame that overlaps with the predicted time window for arrival of the patient at the intensive care unit. The system can then send an alert message to the nurse (e.g., by adding the alert to a patient news feed accessible by the nurse, by sending an alert to the nurse's mobile device, by sending an email to the nurse, by sending a voice message to the nurse, by sending a text message to the nurse, or by sending an alert to a server station at which the nurse is located). The alert message can indicate the patient (e.g., by name, patient ID, or a link to the patient's patient profile) along with an indication of the predicted time window for when the patient is predicted to arrive at the intensive care unit.

As another example, the system can send an alert to a speech therapist associated with a speech therapy unit who is scheduled to be on duty during the predicted time window. The alert can indicate to the speech therapist that the patient is predicted to arrive at the speech therapy unit during the predicted time window. As yet another example, the system can send an urgent alert to a surgeon on duty in an ER that the patient is experiencing cardiac arrest, is being rushed into surgery, and should be properly prepped for surgery and arrive at a particular surgery room in five to ten minutes.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software or hardware product or packaged into multiple software or hardware products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A computer-implemented method for coordinating patient care, the method comprising:
   receiving, by a computer system and from a patient-worn mobile sensor associated with a patient, vital sign information associated with the patient;
   receiving, by the computer system, user input provided by a first caregiver indicating care information for the patient;
   determining, by the computer system and based on the received vital sign information and received user input, a predicted future medical occurrence for the patient;
   identifying a medical occurrence type for the predicted future medical occurrence;
   accessing, by the computer system, medical occurrence type information for the identified medical occurrence type, wherein the medical occurrence type information includes:
   (1) medical occurrence location requirement information for the identified medical occurrence type, the medical occurrence location requirement information indicating one or more location types that are properly equipped for performing the medical occurrence of the identified medical occurrence type, (2) precursor information indicating one or more prior vital sign states or one or more prior medical occurrences indicative of a possible need for the identified medical occurrence type, and (3) time criteria for the identified medical occurrence type, the time criteria including (i) a time required to perform medical occurrences of the identified medical occurrence type or a time required to perform one or more other related medical occurrences: and (ii) time availability of one or more caregivers necessary for performing medical occurrences of the identified medical occurrence type:
   determining, by the computer system a predicted future location for the patient by determining that the predicted future location has a location type that matches the identified one or more location types;
   determining, by the computer system, a predicted time window for arrival of the patient at the predicted future location, wherein the predicted time window is determined based on the time criteria for the identified medical occurrence type included in the medical occurrence type information for the identified medical occurrence type;
   assigning the patient to the predicted future location during the predicted time window;
   identifying one or more caregiver types associated with the medical occurrence type;
   identifying, by the computer system, a second caregiver based on determining that (1) the second caregiver is of the identified one or more caregiver types, (2) the caregiver is available during the predicted time window; and (3) the caregiver is associated with the predicted future location; and
   sending, by the computer system, an alert message to the second caregiver, the alert message including an identifier for the patient and an indication of the predicted time window.

2. The method of claim 1, wherein the vital sign information and the user input are received by the computer system while the patient is located in a first section of a healthcare facility, wherein the predicted future location is a second section of the healthcare facility different than the first section, and the second caregiver is a clinician scheduled to work in the second section of the healthcare facility during the predicted time window.

3. The method of claim 1, wherein:
   the vital sign information and the user input are received by the computer system while the patient is located in a healthcare facility, wherein the predicted future location is a location outside of the healthcare facility;
   determining the predicted future location for the patient includes determining that the patient is to be discharged from the healthcare facility during the predicted time window; and
   the alert message includes an indication that the patient is to be discharged during the predicted time window.

4. The method of claim 1, wherein identifying the second caregiver includes identifying that the second caregiver is scheduled to work at the predicted future location during the predicted time window.

5. The method of claim 1, wherein determining the predicted future location for the patient is performed in response to determining, using the received vital sign information, that the patient has sufficiently recovered from a previous medical occurrence.

6. The method of claim 1, wherein the predicted future location is an outpatient treatment facility and wherein determining the predicted future location for the patient includes determining that the patient requires outpatient treatment of a type performed at the outpatient treatment facility.

7. The method of claim 1, wherein identifying the second caregiver includes determining that the second caregiver is located within a specified proximity of the predicted future location.

8. A non-transitory computer readable storage medium encoded with a computer program, the program comprising instructions that when executed by one or more data processing apparatus cause the one or more data processing apparatus to perform operations comprising:
   receiving, by a computer system and from a patient-worn mobile sensor associated with a patient, vital sign information associated with the patient;
   receiving, by the computer system, user input provided by a first caregiver indicating care information for the patient;
   determining, by the computer system and based on the received vital sign information and received user input, a predicted future medical occurrence for the patient;
   identifying a medical occurrence type for the predicted future medical occurrence;
   accessing, by the computer system, medical occurrence type information for the identified medical occurrence type, wherein the medical occurrence type information includes:
   (1) medical occurrence location requirement information for the identified medical occurrence type, the medical occurrence location requirement information indicating one or more location types that are properly equipped for performing the medical occurrence of the identified medical occurrence type, (2) precursor information indicating one or more prior vital sign states or one or more prior medical occurrences indicative of a possible need for the identified medical occurrence type, and (3) time criteria for the identified medical occurrence type, the time criteria including (i) a time required to perform medical occurrences of the identified medical occurrence type or a time required to perform one or more other related medical occurrences: and (ii) time availability of one or more caregivers necessary for performing medical occurrences of the identified medical occurrence type;

determining, by the computer system a predicted future location for the patient by determining that the predicted future location has a location type that matches the identified one or more location types;

determining, by the computer system, a predicted time window for arrival of the patient at the predicted future location, wherein the predicted time window is determined based on the time criteria for the identified medical occurrence type included in the medical occurrence type information for the identified medical occurrence type;

assigning the patient to the predicted future location during the predicted time window;

identifying one or more caregiver types associated with the medical occurrence type; identifying, by the computer system, a second caregiver based on determining that (1) the second caregiver is of the identified one or more caregiver types, (2) the caregiver is available during the predicted time window; and (3) the caregiver is associated with the predicted future location; and sending, by the computer system, an alert message to the second caregiver, the alert message including an identifier for the patient and an indication of the predicted time window.

9. The non-transitory computer readable storage medium of claim 8, wherein the vital sign information and the user input are received by the computer system while the patient is located in a first section of a healthcare facility, wherein the predicted future location is a second section of the healthcare facility different than the first section, and the second caregiver is a clinician scheduled to work in the second section of the healthcare facility during the predicted time window.

10. The non-transitory computer readable storage medium of claim 8, wherein:
the vital sign information and the user input are received by the computer system while the patient is located in a healthcare facility, wherein the predicted future location is a location outside of the healthcare facility;
determining the predicted future location for the patient includes determining that the patient is to be discharged from the healthcare facility during the predicted time window; and
the alert message includes an indication that the patient is to be discharged during the predicted time window.

11. The non-transitory computer readable storage medium of claim 8, wherein identifying the second caregiver includes identifying that the second caregiver is scheduled to work at the predicted future location during the predicted time window.

12. The non-transitory computer readable storage medium of claim 8, wherein determining the predicted future location for the patient is performed in response to determining, using the received vital sign information, that the patient has sufficiently recovered from a previous medical occurrence.

13. The non-transitory computer readable storage medium of claim 8, wherein the predicted future location is an outpatient treatment facility and wherein determining the predicted future location for the patient includes determining that the patient requires outpatient treatment of a type performed at the outpatient treatment facility.

14. The non-transitory computer readable storage medium of claim 8, wherein identifying the second caregiver includes determining that the second caregiver is located within a specified proximity of the predicted future location.

15. A system comprising:
a patient-worn mobile sensor configured to contact the skin of a patient and collect vital sign information for the patient;
a user input device for receiving user input;
a database hosted on one or more computing devices storing information about a plurality of caregivers; and
a computer system comprising one or more computers in communication with the patient-worn mobile sensor and the user input device that include one or more computer storage media encoded with a computer program, the program comprising instructions that, when executed, cause the one or more computers to perform operations comprising:
receiving, by the computer system and from the patient-worn mobile sensor, vital sign information associated with the patient;
receiving, by the computer system and via the user input device, user input provided by a first caregiver indicating care information for the patient;
determining, by the computer system and based on the received vital sign information and received user input, a predicted future medical occurrence for the patient;
identifying a medical occurrence type for the predicted future medical occurrence;
accessing, by the computer system, medical occurrence type information for the identified medical occurrence type, wherein the medical occurrence type information includes:
(1) medical occurrence location requirement information for the identified medical occurrence type, the medical occurrence location requirement information indicating one or more location types that are properly equipped for performing the medical occurrence of the identified medical occurrence type, (2) precursor information indicating one or more prior vital sign states or one or more prior medical occurrences indicative of a possible need for the identified medical occurrence type, and (3) time criteria for the identified medical occurrence type, the time criteria including (i) a time required to perform medical occurrences of the identified medical occurrence type or a time required to perform one or more other related medical occurrences; and (ii) time availability of one or more caregivers necessary for performing medical occurrences of the identified medical occurrence type;
determining, by the computer system a predicted future location for the patient by determining that the predicted future location has a location type that matches the identified one or more location types;
determining, by the computer system, a predicted time window for arrival of the patient at the predicted future location, wherein the predicted time window is determined based on the time criteria for the identified medical occurrence type included in the medical occurrence type information for the identified medical occurrence type;

assigning the patient to the predicted future location during the predicted time window;

identifying one or more caregiver types associated with the medical occurrence type;

identifying, by the computer system, a second caregiver based on determining that (1) the second caregiver is of the identified one or more caregiver types, (2) the caregiver is available during the predicted time window; and (3) the caregiver is associated with the predicted future location; and sending, by the computer system, an alert message to the second caregiver, the alert message including an identifier for the patient and an indication of the predicted time window.

16. The system of claim 15, wherein the vital sign information and the user input are received by the computer system while the patient is located in a first section of a healthcare facility, wherein the predicted future location is a second section of the healthcare facility different than the first section, and the second caregiver is a clinician scheduled to work in the second section of the healthcare facility during the predicted time window.

17. The system of claim 15, wherein:
the vital sign information and the user input are received by the computer system while the patient is located in a healthcare facility, wherein the predicted future location is a location outside of the healthcare facility;
determining the predicted future location for the patient includes determining that the patient is to be discharged from the healthcare facility during the predicted time window; and
the alert message includes an indication that the patient is to be discharged during the predicted time window.

18. The system of claim 15, wherein determining the predicted future location for the patient is performed in response to determining, using the received vital sign information, that the patient has sufficiently recovered from a previous medical occurrence.

19. The system of claim 15, wherein the predicted future location is an outpatient treatment facility and wherein determining the predicted future location for the patient includes determining that the patient requires outpatient treatment of a type performed at the outpatient treatment facility.

20. The system of claim 15, wherein identifying the second caregiver includes determining that the second caregiver is located within a specified proximity of the predicted future location.

\* \* \* \* \*

UNITED STATES PATENT AND TRADEMARK OFFICE
CERTIFICATE OF CORRECTION

PATENT NO. : 10,621,686 B2
APPLICATION NO. : 14/681385
DATED : April 14, 2020
INVENTOR(S) : Mazar et al.

Page 1 of 1

It is certified that error appears in the above-identified patent and that said Letters Patent is hereby corrected as shown below:

In the Claims

In Column 67, Line 43, Claim 1, delete "occurences:" and insert -- occurences; --, therefor;

In Column 67, Line 46, Claim 1, delete "type:" and insert -- type; --, therefor;

In Column 69, Line 9, Claim 8, delete "occurences:" and insert -- occurences; --, therefor.

Signed and Sealed this
Sixteenth Day of June, 2020

Andrei Iancu
*Director of the United States Patent and Trademark Office*